(12) United States Patent
Bright et al.

(10) Patent No.: US 7,244,614 B2
(45) Date of Patent: Jul. 17, 2007

(54) FUSION PROTEINS AND ASSAYS FOR MOLECULAR BINDING

(75) Inventors: Gary Bright, Allison Park, PA (US); Daniel Rajadavid Premkumar, Monroeville, PA (US); Yih-Tai Chen, Gibsonia, PA (US)

(73) Assignee: Cellomics, Inc., Pittsburgh, PA (US)

( * ) Notice: Subject to any disclaimer, the term of this patent is extended or adjusted under 35 U.S.C. 154(b) by 485 days.

(21) Appl. No.: 10/211,088

(22) Filed: Aug. 1, 2002

(65) Prior Publication Data

US 2003/0104479 A1 Jun. 5, 2003

Related U.S. Application Data

(60) Provisional application No. 60/341,589, filed on Dec. 13, 2001, provisional application No. 60/309,395, filed on Aug. 1, 2001.

(51) Int. Cl.
| | |
|---|---|
| C12N 15/00 | (2006.01) |
| C12N 1/20 | (2006.01) |
| C12N 9/00 | (2006.01) |
| C07H 21/04 | (2006.01) |
| C12P 21/06 | (2006.01) |

(52) U.S. Cl. ............... 435/320.1; 536/23.1; 435/252.3; 435/69.1; 435/183
(58) Field of Classification Search ............... 536/23.2, 536/23.1; 435/194, 320.1, 252.3, 69.1, 183
See application file for complete search history.

(56) References Cited

U.S. PATENT DOCUMENTS

| | | | |
|---|---|---|---|
| 5,683,888 A | 11/1997 | Campbell | |
| 5,912,137 A | 6/1999 | Tsien et al. | |
| 5,925,558 A | 7/1999 | Tsien et al. | |
| 5,958,713 A | 9/1999 | Thastrup et al. | |
| 5,989,835 A | 11/1999 | Dunlay et al. | |
| 6,197,928 B1 | 3/2001 | Tsien et al. | |
| 6,248,550 B1 | 6/2001 | Tsien et al. | |
| 6,270,964 B1 | 8/2001 | Michnick et al. | |
| 6,416,959 B1 | 7/2002 | Giuliano | |
| 6,518,021 B1 | 2/2003 | Thastrup et al. | |

(Continued)

FOREIGN PATENT DOCUMENTS

WO    WO 96/23898    8/1996

(Continued)

OTHER PUBLICATIONS

Grove te al, Biochemistry, 32, 7727-7738, 1993.*

(Continued)

*Primary Examiner*—Maryam Monshipouri
(74) *Attorney, Agent, or Firm*—McDonnell Boehnen Hulbert & Berghoff, LLP

(57) ABSTRACT

The present invention provides novel recombinant fusion proteins for detecting binding of a molecule of interest containing a detection domain, a first and optionally a second localization domain, and a binding domain. The invention also provides recombinant nucleic acid molecules and recombinant expression vectors encoding these novel fusion proteins, genetically engineered host cells containing these expression vectors, and kits for the use of these fusion proteins, nucleic acid molecules, expression vectors, and host cells. Additionally, the present invention provides methods for identifying compounds that alter the binding of a molecule of interest in a cell.

31 Claims, 30 Drawing Sheets

U.S. PATENT DOCUMENTS

| | | | |
|---|---|---|---|
| 6,566,083 | B1 | 5/2003 | Thastrup et al. |
| 6,573,039 | B1 | 6/2003 | Dunlay et al. |
| 6,620,591 | B1 | 9/2003 | Dunlay |
| 6,671,624 | B1 | 12/2003 | Dunlay et al. |
| 6,716,588 | B2 | 4/2004 | Sammak |
| 6,727,071 | B1 | 4/2004 | Dunlay |
| 6,756,207 | B1 | 6/2004 | Giuliano |
| 6,759,206 | B1 | 7/2004 | Rubin |
| 6,875,578 | B2 | 4/2005 | Giuliano |
| 6,902,883 | B2 | 6/2005 | Dunlay |

FOREIGN PATENT DOCUMENTS

| | | |
|---|---|---|
| WO | WO 98/02571 | 1/1998 |
| WO | WO 98/38490 | 9/1998 |
| WO | WO 98/45704 | 10/1998 |
| WO | WO 00/03246 | 1/2000 |
| WO | WO 00/23615 | 4/2000 |
| WO | WO 00/23621 | 4/2000 |
| WO | WO 00/26408 | 5/2000 |
| WO | WO 00/43780 | 7/2000 |
| WO | WO 00/70342 | 11/2000 |

OTHER PUBLICATIONS

Hino, Shikoku Shigaklai Zasshi, 13(1), 67-89, 2000.*
Murakami et al., Tennen Yuki Kagobutsu Toronkai Koen Yoshisu, 41st, 229-234, 1999.*
Barber et al., (1996), *Neuroscience Letters* 207:17-20.
Bessert, D.A. et al., (1995), *Brain Res Mol Brain Res.*, 33:165-73.
Blauer, M. et al., (1999), *Biol Reprod.*, 60:588-93
Bonifaci, N. et al., (1997), *Proc Natl Acad Sci USA*, 94:5055-60.
Bouvier, D. et al., (1995), *Mol Biol Cell*, 6:1697-705.
Bright et al., (1996), *Cytometry* 24:226-233.
Buckler et al., (1993), *Analyt. Biochem.* 209:20-31.
Carriere, C. et al., (1995), *Cell Growth Differ.*, 6:1531-40.
Chan, C.K. et al., (1998), *Gene Ther.*, 5:1204-12.
Chang, D. et al., (1992), *Virology*, 191:978-83.
Chang, D. et al., (1992), *Virology*, 189:821-7.
Chang, S.C. et al., (1994), *Biochem. Biophys. Res. Commun.*, 205:1284-90.
Dang, C.V. et al., (1989), *J. Biol. Chem.*, 264:18019-23.
Eguchi, H. et al., (1997), *J. Biol. Chem.*, 272:17640-7.
Gao, M. et al., (1992), *Mol. Cell Biol.*, 12:1330-9.
Gilmore, T.D. et al., (1988), *J. Virol.*, 62:703-14.
Giuliano and Taylor (1995), *Curr. Op. Cell Biol.* 7:4-12.
Giuliano et al. (1990) *Optical Microscopy for Biology.* pp. 543-557.
Giuliano et al. (1995) *Ann. Rev. Biophys. Biomol. Struct.* 24:405-434.
Giuliano, et al., (1997) *J. Biomol. Screening*, 2(4):249-259.
Hall, et al., (1984), *Cell*, 36:1057-65.
Hicks, G.R. et al., (1995), *Proc. Natl. Acad. Sci. USA*, 92:734-8.
Hsieh, J.C. et al., (1998), *J. Cell Biochem.*, 70:94-109.
Ide, Y. et al., (1996), *Gene*, 182:203-11.
Irie, Y. et al., (2000), *J. Biol. Chem.*, 275, 2647-53.
Kalderon, D. et al., (1984), *Cell*, 39:499-509.
Kaneko, H. et al., (1997), *Biochem. Biophys. Res. Commun.*, 240:348-53.
Kato, G.J. et al., (1992), *Genes Dev.*, 6:81-92.
Knuehl, C. et al., (1996), *Exp. Cell Res.*, 225:67-74.
Koike, M. et al., (1999), *Exp Cell Res*, 250:401-13.
Kukolj, G. et al., (1998), *Gene*, 223:157-63.
Liang, S.H. et al., (1999), *Oncogene*, 18:2163-6.
Liu, M.T. et al., (1998), *Virology*, 247:62-73.
Lyons, R.H. et al., (1987), *Mol. Cell Biol.*, 7, 2451-6.
Mattaj, I.W. et al., (1998), *Annu. Rev. Biochem*, 67:265-306.
McBride, et al., (2000), *EMBO J*, 19: pp. 6196-6206.
McNeil, (1989), *Methods in Cell Biology* 29:153-173.
Michael, W.M. et al., (1997), *Embo J.*, 16:3587-98.
Miyamoto, Y. et al., (1997), *J. Biol. Chem.*, 272:26375-81.
Mizuno, T. et al., (1996), *Cell Sci.*, 109:2627-36.
Moede, T. et al., (1999), *FEBS. Lett.*, 461:229-34.
Robbins, J. et al., (1991), *Cell*, 64:615-23.
Rubinfeld, et al., (1990), *J. Biol. Chem.*, 274(43): 30349-30352.
Rubtsov, Y.P. et al., (1997), *FEBS Lett*, 413:135-41.
Schmidt-Zachmann, et al., (1993), *J. Cell Sci.*, 105:799-806.
Schreiber, V. et al., (1992), *Embo J.*, 11:3263-9.
Schwemmle, M. et al., (1999), *J. Gen. Virol.*, 80:97-100.
Shoya, Y. et al., (1998), *J. Virol.*, 72:9755-62.
Singer et al., (1997), *Annu. Rev Biochem.* 66:475-509.
Sock, E. et al., (1996), *J. Biol. Chem.*, 271:17512-8.
Somasekaram, A. et al., (1999), *J. Biol. Chem.*, 274:28405-12.
Moreland, R.B. et al. (1987), *Mol. Cell Biol.*, 7:4048-57.
Moreland, R.B. et al., (1985), *Proc. Natl. Acad. Sci. USA*, 82:6561-5.
Nederlof, P.M. et al., (1995), *Proc. Natl. Acad. Sci. USA*, 92:12060-4.
Noren et al., (1989), *Science.* 244:182-188.
Palmeri, D. et al., (1999), *Mol. Cell Biol.*, 19:1218-25.
Perander, et al., (2001), *J. Biol. Chem.*, 276: 13015-24.
Post et al., (1994), *J. Biol. Chem.* 269:12880-12887.
Prieve, M.G. et al., (1998), *Mol. Cell Biol.*, 18:4819-32.
Rhee, S.K. et al., (1989), *Yeast*, 5:149-58.
Richardson, W.D. et al., (1986), *Cell* , 44:77-85.
Sudbeck, P. et al., (1997), *J. Biol. Chem.*, 272:27848-52.
Takashi, (1988), *Biochemistry.* 27:938-943.
Tinland, B. et al., (1992), *Proc. Natl. Acad. Sci. USA*, 89:7442-6.
Truant, R. et al., (1999), *Mol. Cell Biol.*, 19:1210-7.
Truant, R. et al., (1998), *Mol. Cell Biol.*, 18:1449-58.
Underwood, M.R. et al., (1990), *Embo J.*, 9:91-9.
Vandromme, M. et al., (1995), *Proc. Natl. Acad. Sci. USA*, 92:4646-50.
Vihinen-Ranta, M. et al., (1997), *Eur. J. Biochem.*, 250:389-94.
Wang, P. et al., (1997), *J. Virol.*, 71:1850-6.
Wang, Y. et al., (1995), *J. Biol. Chem.*, 270:354-60.
Wang et al., (2000), *J. Biol. Chem.* 275:7466-7469.
Weber, F. et al., (1998), *Virology*, 250:9-18.
Welch, K. et al., (1999), *Mol. Cell Biol.*, 19:8400-11.
Wu, J. et al., (1999), *J. Biol. Chem.*, 274:29202-10.
Wychowski, C. et al., (1986), *Embo. J.*, 5:2569-76.
Wychowski, C. et al., (1987), *J. Virol.*, 61:3862-9.
Xiao, et al., (1998), *FEBS Letters, Elsevier Science Publishers*, 436(3): 313-317.
Youssoufian, H. et al. (1999), *Mol. Dis.*, 25:305-9.
Yu, Z. et al. (1998), *J. Endocrinol*, 159:53-60.
Zacksenhaus, E. et al. (1993), *Mol. Cell Biol.*, 13:4588-99.
Ahn, et al., (2001), Molecules and Cells, "Mapping of the Interaction Domain of the Protein Kinase CKII β Subunit with Target Proteins", vol. 12(2), pp. 158-163.
Hübner, et al., (1997), The Journal of Biological Chemistry, "The Protein Kinase CK2 Site (Ser $^{111/112}$) Enhances Recognition of the Simian Virus 40 Large T-antigen Nuclear Localization Sequence by Importin", vol. 272(27), pp. 17191-17195.
Xiao, et al., (1997), The Journal of Biological Chemistry, "SV40 Large Tumor Antigen Nuclear Import is Regulated by the Double-stranded DNA-dependent Protein Kinase Site (Serine 120) Flanking the Nuclear Localization Sequence", vol. 272(35), pp. 22191-22198.
Xiao, et al., (1996), The Journal of Biological Chemistry, "A Consensus cAMP-dependent Protein Kinase (PK-A) Site in Place of the CcN Motif Casein Kinase II Site of Simian Virus 40 Large T-antigen Confers PK-A-mediated Regulation of Nuclear Import", vol. 271(11), pp. 6451-6457.

* cited by examiner

Figure 2A: Subcellular Compartment Localization Sequences

| Target | Source | Sequence | SEQ ID NO. | Reference |
|---|---|---|---|---|
| Cytoplasm/cytoskeleton | Annexin II | M S T V H E I L C K L S L E G V H S T P P S A | 1 | Eberhard, et al., 1997, Mol. Biol. Cell 8:293a. |
| | | ATGTCTACTGTCCACGAAATC CTGTGCAAGCTCAGCTTGGA GGGTGTTCATTCTACACCCCC AAGTGCC | 2 | |
| Inner surface of plasma membrane | farnesylation | M G C T L S A E D K A A V E R S K M I D R N L R E D G E K A A R | 3 | Ferruccio G, et al., J. Biol. Chem. 274, 5843-5850, 1999 |
| | | AUGGGATCTACATTAAGCGC AGAAGACAAAGCAGCAGTAG AAAGAAGCAAAAUGATAGACA GAAACTTATTAAGAGAAGACG GAGAAAAAGCTGCTAGA | 4 | |
| Nucleus | NFkB p50 | R R K R Q K | 5 | Henkel, T et al., Cell 68, 1121-1133, 1992 |
| | | AGAAGGAAACGACAAAAG | 6 | |
| Nucleolus | NOLP | R K R I R T Y L K S C R R M K R S G F E M S R P I P S H L T | 7 | Ueki, et al., 1998. Biochem Biophys Res Commun. 252:97-102. |
| | | AGAAAACGTATACGTACTTAC CTCAAGTCCTGCAGGCGGAT GAAAAGAAGTGGTTTTGAGAT GTCTCGACCTATTCCTTCCCA CCTTACT | 8 | |
| Mitochondria | cytochrome c oxidase | M S V L T P L L L R G L T G S A R R L P V P R A L I H S L | 9 | Rizzuto, et al., 1989. J Biol Chem. 264:10595-600. |
| | | ATGTCCGTCCTGACGCCGCT GCTGCTGCGGGGCTTGACAG GCTCGGCCCGGCGGCTCCCA GTGCCGCGCGCCAAGATCCA TTCGTTG | 10 | |
| Nuclear Envelope | ODV-E66 & ODV-E25 | MSIVLIIVIVVIFLICFLYLSNSKD PRVPVELM | 11 | Hong, T, et al. PNAS, 94, 4050-4055, 1997 |

Figure 2B

| | | | | |
|---|---|---|---|---|
| | | AUGAGCATTGTTTTAATAATT GTTATTTGGATTTTTTTAATAT GTTTTTTATATTTAAGCAACAG CAAAGATCCCAGAGTACCAG TTGAATTAAUG | 12 | |
| | | | | |
| Golgi | Calreticulin | MRLREPLLSGSAAMPGASLQR ACRLLVAVCALHLGVTLVYYLA GRDLSRLPQLVGVSTPLQGGS NSAAAIGQSSGELRTGGA | 13 | Fliegel, L., et al., J. Biol. Chem. 264, 21522-21528, 1989. |
| | | ATGAGGCTTCGGGAGCCGCT CCTGAGCGGCAGCGCCGCG ATGCCAGGCGCGTCCCTACA GCGGGCCTGCCGCCTGCTCG TGGCCGTCTGCGCTCTGCAC CTTGGCGTCACCCTCGTTTAC TACCTGGCTGGCCGCGACCT GAGCCGCCTGCCCCAACTGG TCGGAGTCTCCACACCGCTG CAGGGCGGCTCGAACAGTGC CGCCGCCATCGGGCAGTCCT CCGGGGAGCTCCGGACCGG AGGGGCC | 14 | |
| | | | | |
| Endoplasmic reticulum | D-AKAP1 | ETIRPIRIRRCSYFTSTDSKMAI QLRSPFPLALPGMLALLGWW WFFSRKK | 15 | Huang, LJ. Et al., J. Cell. Biol. 145, 951-959, 1999 |
| | | GAAACAATAAGACCTATAAGA AGATGTAGTACATTTACATCT ACAGACAGCAAAAUGGCAAT TCAATTAAGATCTCCCTTTCC ATTAGCATTACCAGGAAUGTT AGCTTTATTAGGATGGTGGTG GTTTTTCAGTAGAAAAAAA | 16 | |
| | | | | |
| Nuclear Export | MEK1 | ALQKKLEELELDE | 17 | Fukuda, (1997) J. Biol. Chem 272, 51, 32642-32648 |
| | | GCCTTGCAGAAGAAGCTGGA GGAGCTAGAGCTTGATGAG | 18 | |
| | | | | |
| Size exclusion | nmer of GFP | | | Tsien, R.Y. 1998. Annu Rev Biochem. 67:509-44. |
| | | | | |

Figure 2C

| Size exclusion | PROJ domain of MAP4 | ADLSLVDALTEPPPEIEGEIKRD FMAALEAEPYDDIVGETVEKTE FIPLLDGDEKTGNSESKKKPCL DTSQVEGIPSSKPTLLANGDH GMEGNNTAGSPTDFLEERVDY PDYQSSQNWPEDASFCFQPQ QVLDTDQAEPFNEHRDDGLAD LLFVSSGPTNASAFTERDNPSE DSYGMLPCDSFASTAVVSQE WSVGAPNSPCSESCVSPEVTI ETLQPATELSKAAEVESVKEQL PAKALETMAEQTTDVVHSPST DTTPGPDTEAALAKDIEEITKPD VILANVTQPSTESDMFLAQDM ELLTGTEAAHANNIILPTEPDES STKDVAPPMEEEIVPGNDTTSP KETETTLPIKMDLAPPEDVLLTK ETELAPAKGMVSLSEIEEALAK NDVRSAEIPVAQETVVSETEVV LATEVVLPSDPITTLTKDVTLPL EAERPLVTDMTPSLETEMTLG KETAPPTETNLGMAKDMSPLP ESEVTLGKDVVILPETKVAEFN NVTPLSEEEVTSVKDMSPSAE TEAPLAKNADLHSGTELIVDNS MAPASDLALPLETKVATVPIKD KG | 19 | West, (1991). J Biol Chem 266(32): 21886-96; Olson, K. R. (1995). J Cell Biol 130(3): 639-50. |
|---|---|---|---|---|
| | | GCCGACCTCAGTCTTGTGGA TGCGTTGACAGAACCACCTC CAGAAATTGAGGGAGAAATAA AGCGAGACTTCATGGCTGCG CTGGAGGCAGAGCCCTATGA TGACATCGTGGGAGAAACTG TGGAGAAAACTGAGTTTATTC CTCTCCTGGATGGTGATGAG AAAACCGGGAACTCAGAGTC CAAAAAGAAACCCTGCTTAGA CACTAGCCAGGTTGAAGGTA TCCCATCTTCTAAACCAACAC TCCTAGCCAATGGTGATCATG GAATGGAGGGGAATAACACT GCAGGGTCTCCAACTGACTT CCTTGAAGAGAGAGTGGACT ATCCGGATTATCAGAGCAGC CAGAACTGGCCAGAAGATGC AAGCTTTTGTTTCCAGCCTCA GCAAGTGTTAGATACTGACCA GGCTGAGCCCTTTAACGAGC ACCGTGATGATGGTTTGGCA GATCTGCTCTTTGTCTCCAGT GGACCCACGAACGCTTCTGC ATTTACAGAGCGAGACAATCC TTCAGAAGACAGTTACGGTAT GCTTCCCTGTGACTCATTTGC TTCCACGGCTGTTGTATCTCA GGAGTGGTCTGTGGGAGCCC | 20 | |

Figure 2D

| | | | | |
|---|---|---|---|---|
| | | CAAACTCTCCATGTTCAGAGT<br>CCTGTGTCTCCCCAGAGGTT<br>ACTATAGAAACCCTACAGCCA<br>GCAACAGAGCTCTCCAAGGC<br>AGCAGAAGTGGAATCAGTGA<br>AAGAGCAGCTGCCAGCTAAA<br>GCATTGGAAACGATGGCAGA<br>GCAGACCACTGATGTGGTGC<br>ACTCTCCATCCACAGACACAA<br>CACCAGGCCCAGACACAGAG<br>GCAGCACTGGCTAAAGACAT<br>AGAAGAGATCACCAAGCCAG<br>ATGTGATATTGGCAAATGTCA<br>CGCAGCCATCTACTGAATCG<br>GATATGTTCCTGGCCCAGGA<br>CATGGAACTACTCACAGGAA<br>CAGAGGCAGCCCACGCTAAC<br>AATATCATATTGCCTACAGAA<br>CCAGACGAATCTTCAACCAAG<br>GATGTAGCACCACCTATGGA<br>AGAAGAAATTGTCCCAGGCA<br>ATGATACGACATCCCCCAAAG<br>AAACAGAGACAACACTTCCAA<br>TAAAAATGGACTTGGCACCAC<br>CTGAGGATGTGTTACTTACCA<br>AAGAAACAGAACTAGCCCCA<br>GCCAAGGGCATGGTTTCACT<br>CTCAGAAATAGAAGAGGCTCT<br>GGCAAAGAATGATGTTCGCT<br>CTGCAGAAATACCTGTGGCT<br>CAGGAGACAGTGGTCTCAGA<br>AACAGAGGTGGTCCTGGCAA<br>CAGAAGTGGTACTGCCCTCA<br>GATCCCATAACAACATTGACA<br>AAGGATGTGACACTCCCCTTA<br>GAAGCAGAGAGACCGTTGGT<br>GACGGACATGACTCCATCTCT<br>GGAAACAGAAATGACCCTAG<br>GCAAAGAGACAGCTCCACCC<br>ACAGAAACAAATTTGGGCATG<br>GCCAAAGACATGTCTCCACTC<br>CCAGAATCAGAAGTGACTCT<br>GGGCAAGGACGTGGTTATAC<br>TTCCAGAAACAAAGGTGGCT<br>GAGTTTAACAATGTGACTCCA<br>CTTTCAGAAGAAGAGGTAACC<br>TCAGTCAAGGACATGTCTCC<br>GTCTGCAGAAACAGAGGCTC<br>CCCTGGCTAAGAATGCTGAT<br>CTGCACTCAGGAACAGAGCT<br>GATTGTGGACAACAGCATGG<br>CTCCAGCCTCCGATCTTGCA<br>CTGCCCTTGGAAACAAAAGTA<br>GCAACAGTTCCAATTAAAGAC<br>AAAGGA | | |

Figure 2E

| | | | | |
|---|---|---|---|---|
| Vesicle membrane | Synaptobrevin | MWAIGITVLVIFIIIIIVWVV | 21 | Schiavo et al., (1992) Nature 359, 832-5 |
| | | ATGTGGGCAATCGGGATTAC TGTTCTGGTTATCTTCATCAT CATCATCATCGTGTGGGTTGT C | 22 | |
| | | | | |
| | | MWAIGISVLVIIVIIIIVWC | 23 | |
| Vesicle membrane | Cellubrevin | ATGTGGGCGATAGGGATCAG TGTCCTGGTGATCATTGTCAT CATCATCATCGTGTGGTGTG | 24 | McMahon et al., Nature 364:346-349; Martin et al., J. Cell Biol. In press |

Figure 3A: Examples of Binding Domains

| Source Genbank Accession # | Binding Domain | Molecule of Interest | SEQ ID NO. | Reference |
|---|---|---|---|---|
| MEK1 NM_002755 | M P K K K P T P I Q L N P A P<br>atgcccaagaagaagccgacgcccatccagctga acccggcccc | ERK | 25<br>26 | Tanoue et al (2001) Nature Cell Biology 2:110-116 |
| MEK2 BC018645 | M L A R R K P V L P A L T I N P<br>atgctggcccggaggaagccggtgctgccggcgc tcaccatcaaccct | ERK | 27<br>28 | Tanoue et al (2001) Nature Cell Biology 2:110-116 |
| RSK1 L07597 | S S I L A Q R R V R K L P S T T L<br>tcatccatcctggcccagcggcgagtgaggaagt tgccatccaccacctg | ERK | 29<br>30 | Tanoue et al (2001) Nature Cell Biology 2:110-116 |
| RSK2 NM_004586 | R S T L A Q R R G I K K I T S T A L<br>cgctctactcttgctcagcggagaggtattaaaa aaatcacctcaacagccctg | ERK | 31<br>32 | Tanoue et al (2001) Nature Cell Biology 2:110-116 |
| RSK3 XM_004469 | S S N L A Q R R G M K R L T S T R L<br>tcatccaacctggctcagcgcagaggcatgaaga gactcacgtccacgcggctg | ERK | 33<br>34 | Tanoue et al (2001) Nature Cell Biology 2:110-116 |
| MNK2 AF237775 | Q S K L A Q R R Q R A S L S S A P V<br>cagtccaagctggcgcagcggcggcaaagggcca gtctgtcctcggccccagtg | ERK | 35<br>36 | Tanoue et al (2001) Nature Cell Biology 2:110-116 |
| LIN-1 AH003439 | G M K P N P L N L T A T S N F S<br>ggaatgaagccgaacccgctgaacctgacagcaa cctcgaatttctcc (C. elegans) | ERK | 37<br>38 | Sharrocks, A.D. et al. (2000) TIBS 25: 448-452 |
| Elk-1 NM_005229, Net | FXFP Consensus F Q F P<br>Ttccagttttcca (human ELK 1 NM_005229) | ERK | 39<br>40 | Jacobs et al., (1999) Genes & Dev 13:163-175 |
| MKP3 AB013602 | P G I M L R R L Q K G N L P V R<br>ccgggcatcatgctgcggcgcctgcagaagggta acctgccggtgcgc | ERK | 41<br>42 | Tanoue et al (2001) Nature Cell Biology 2:110-116 |
| Pyst2 XM_037430 | P G L M L R R L R K G N L P I R<br>ccgggcctcatgttgcgccgcctgcgcaagggca acctgcccatccgc | ERK | 43<br>44 | Tanoue et al (2001) Nature Cell Biology 2:110-116 |
| MKP4 Y08302 | L P A L L R R L R R G S L S V R<br>ctgccggcgctcctgctgcgccgcctgcggaggg gcagcctgtcggtgcgc | ERK | 45<br>46 | Tanoue et al (2001) Nature Cell Biology 2:110-116 |
| B23 XM_045322 | L N S V V L R R A R G A V S A<br>ctcaactcggtggtgctgcggcgggcccggggcg gcgcggtgtcggcg | ERK | 47<br>48 | Tanoue et al (2001) Nature Cell Biology 2:110-116 |

Figure 3B

| | | | | |
|---|---|---|---|---|
| EC-PTP<br>X82635 | G L Q E R R G S N V S<br>L T L D M<br>gctctggcagcggggggtgtaggtgtgttgcact<br>acactgaatggaata | ERK | 49<br>50 | Tanoue et al (2001)<br>Nature Cell Biology<br>2:110-116 |
| HePTP<br>BC001746 | R L Q E R R G S N V A<br>L M L D V<br>Cgactgcaggagaggcggggctccaatgtggctc<br>tgatgctggacgtt | ERK | 51<br>52 | Tanoue et al (2001)<br>Nature Cell Biology<br>2:110-116 |
| STEP<br>NM_002849 | G L Q E R R G S N V S<br>L T L D M<br>ggacttcaagagagaagagggtccaacgtatctc<br>ttacattggacatg | ERK | 53<br>54 | Tanoue et al (2001)<br>Nature Cell Biology<br>2:110-116 |
| MAPKAP2<br>X75346 | N P L L L K R R K K A<br>R A K E A A A<br>aaccctctgctgctgaagaggcggaagaaagctc<br>gggccctggaggctgcggct | p38 | 55<br>56 | Tanoue et al (2001)<br>Nature Cell Biology<br>2:110-116; Cobb et al.,<br>(1996) Adv Pharmacol<br>36:49-65 |
| MKK3<br>D87116 | K G K S R K K D L R<br>I<br>aaaggaaaatccaagaggaagaaggatctacgga<br>ta | p38 | 57<br>58 | Tanoue et al (2001)<br>Nature Cell Biology<br>2:110-116; Su & Karin<br>1996 Curr Opin<br>Immunol 8:402-411 |
| MKK6<br>U49732 | S K G K K R N P G L K<br>I P<br>tcgaaaggcaagaagcgaaaccctggccttaaaa<br>ttcca | p38 | 59<br>60 | Tanoue et al (2001)<br>Nature Cell Biology<br>2:110-116; Su & Karin<br>1996 Curr Opin<br>Immunol 8:402-411 |
| MAPKAP3<br>BC010407 | N R L N K R R K K Q<br>A G S S S A S<br>aaccggctcctcaacaagaggagaaaaaagcagg<br>caggcagctcctctgcctca | p38 | 61<br>62 | Tanoue et al (2001)<br>Nature Cell Biology<br>2:110-116; Cobb et al.,<br>(1996) Adv Pharmacol<br>36:49-65 |
| PRAK<br>BC000833 | N N P I L R K R K L L<br>G T K P K D S<br>aacaaccccattctgcggaagaggaagttacttg<br>gcaccaagccaaaggacagt | p38 | 63<br>64 | Tanoue et al (2001)<br>Nature Cell Biology<br>2:110-116; Cobb et al.,<br>(1996) Adv Pharmacol<br>36:49-65 |
| RSKB<br>XM_006538 | N A P L A K R R K Q K<br>L R S A T A S<br>aatgcaccccctggccaagcggcggaagcagaagc<br>tgcggagcgccaccgcctcc | p38 | 65<br>66 | Tanoue et al (2001)<br>Nature Cell Biology<br>2:110-116; Cobb et al.,<br>(1996) Adv Pharmacol<br>36:49-65 |
| MEF2C<br>L08895 | N R K P D L R V L I<br>aaccgtaaaccagatctccgagttcttatt | p38 | 67<br>68 | Sharrocks, A.D. et al.<br>(2000) TIBS 25: 448-<br>452 |
| MEF2A<br>XM_113793 | N S R K P D L R V V I<br>aacagtaggaaaccagatcttcgagttgtcatc | p38 | 69<br>70 | Sharrocks, A.D. et al.<br>(2000) TIBS 25: 448-<br>452 |
| MKK7<br>NM_005043 | E A R R R I D L N L D<br>I S P<br>gaggcccggcggaggatcgacctcaacctggata<br>tcagcccc | JNK | 71<br>72 | Tanoue et al (2001)<br>Nature Cell Biology<br>2:110-116; Ip & Davis<br>(1998) Curr Biol 10:205-<br>219 |

Figure 3C

| | | | | |
|---|---|---|---|---|
| c-Jun<br>J04111 | I L K Q S M T L N L A<br>D P V G S L<br>atcctgaaacagagcatgaccctgaacctggccg<br>acccagtggggagcctg | JNK | 73<br>74 | Sharrocks, A.D. et al.<br>(2000) TIBS 25: 448-452 |
| JunB<br>U20734 | L L K P S L A V N L A<br>D P Y R S L<br>ctcctgaaaccgagcctggcggtcaacctggcg<br>accccctaccggagtctc | JNK | 75<br>76 | Sharrocks, A.D. et al.<br>(2000) TIBS 25: 448-452 |
| NFAT4<br>U85428 | L E R P S R D H L Y L<br>P L E P S Y R<br>ttggaaaggccttctagagatcatctctatcttc<br>ctcttgagccatcctaccgg | JNK | 77<br>78 | Sharrocks, A.D. et al.<br>(2000) TIBS 25: 448-452 |
| ATFa<br>X57197 | V H K H K H E M T L K<br>F G P A R T<br>gttcataaacacaagcatgagatgacattgaaat<br>ttggcccagcccgaact | JNK | 79<br>80 | Sharrocks, A.D. et al.<br>(2000) TIBS 25: 448-452 |
| MNK1<br>AB000409 | K S R L A R R R A L A<br>Q A G R G E D<br>aagtcacgcctggcccggagacgggccctggccc<br>aggcaggccgtggtgaagac | ERK,<br>P38 | 81<br>82 | Tanoue et al (2001)<br>Nature Cell Biology<br>2:110-116; Cobb et al.,<br>(1996) Adv Pharmacol<br>36:49-65 |
| MSK1<br>AF074393 | K A P L A K R R K M K<br>K T S T S T E<br>aaggcccctttggctaagagaagaaaaatgaaaa<br>agactagcaccagtaccgag | ERK,P38 | 83<br>84 | Tanoue et al (2001)<br>Nature Cell Biology<br>2:110-116; Cobb et al.,<br>(1996) Adv Pharmacol<br>36:49-65 |
| SAP-1<br>NM-001973 | R S K K P K G L G L A<br>P T L V I<br>agatccaagaaacccaaaggggttaggactggcac<br>ccacccttgtgatc | ERK,p38 | 85<br>86 | Sharrocks, A.D. et al.<br>(2000) TIBS 25: 448-452 |
| SAP-2<br>XM_006890 | K A K K P K G L E I S<br>A P P L V L<br>aaggccaaaaaacccaaaggcttggaaatctcag<br>cgcccccgctggtgctc | ERK,p38 | 87<br>88 | Sharrocks, A.D. et al.<br>(2000) TIBS 25: 448-452 |
| SEK1/MKK4<br>NM_003010 | Q G K R K A L K L N F<br>cagggtaaacgcaaagcactgaagttgaattttt | p38, JNK | 89<br>90 | Tanoue et al (2001)<br>Nature Cell Biology<br>2:110-116; Ip & Davis<br>(1998) Curr Biol 10:205-219 |
| ATF-2<br>NM_001880 | V H K H K H E M T L K<br>F G P A R N<br>gtccataaacataaacatgagatgacactgaaat<br>ttggtccagcacgtaat | p38, JNK | 91<br>92 | Sharrocks, A.D. et al.<br>(2000) TIBS 25: 448-452 |
| hVH5 | S K L V K R R L Q Q G<br>K V T I<br>agtaaattagttaagagaagattacaacaaggca<br>aagttactatt | p38, JNK | 93<br>94 | Tanoue et al (2001)<br>Nature Cell Biology<br>2:110-116; Chu et al.,<br>(1996) J Biol Chem<br>271:6497-6501 |
| MKP5<br>AF179212 | C A D K I S R R R L Q<br>Q G K I T V<br>tgtgccgataagatcagccggcggagactgcagc<br>agggcaagatcactgtc | p38,JNK | 95<br>96 | Tanoue et al (2001)<br>Nature Cell Biology<br>2:110-116; Chu et al.,<br>(1996) J Biol Chem<br>271:6497-6501 |

Figure 3D

| | | | | |
|---|---|---|---|---|
| Elk-1<br>M25269 | K G R K P R D L E L P<br>L S P S L L<br>aagggccggaagccccgggacctagagcttccac<br>tcagcccgagcctgcta | ERK,<br>JNK | 97<br>98 | Sharrocks, A.D. et al.<br>(2000) TIBS 25: 448-<br>452 |
| CL100/MKP1<br>X68277 | R F S T I V R R R A K<br>G A M<br>cgcttcagcaccatcgtgcggcgccgggccaagg<br>gcgccatg | ERK,JNK<br>,p38 | 99<br>100 | Tanoue et al (2001)<br>Nature Cell Biology<br>2:110-116; Chu et al.,<br>(1996) J Biol Chem<br>271:6497-6501 |
| MKP2<br>NM_001394 | R C N T I V R R R A K<br>G S V S L E<br>cgctgtaacaccatcgtgcggcggcgggctaagg<br>gctccgtgagcctggag | ERK,JNK<br>,p38 | 101<br>102 | Tanoue et al (2001)<br>Nature Cell Biology<br>2:110-116; Chu et al.,<br>(1996) J Biol Chem<br>271:6497-6501 |
| PAC1<br>L11329 | P W N A L L R R R A R<br>G P P<br>ccttggaacgcgctgctgcggcgccgcgcgcg<br>gccctcct | ERK,JNK<br>,p38 | 103<br>104 | Tanoue et al (2001)<br>Nature Cell Biology<br>2:110-116; Chu et al.,<br>(1996) J Biol Chem<br>271:6497-6501 |
| CREB<br>NM_004379 | I A E S E D S Q E S V<br>D S V T D S Q K R R E I<br>L S R R P S Y R K I L N<br>D L S S D A P G V P R I<br>E E E K S E E E T S A<br>attgcagaaagtgaagattcacaggagtcagtgg<br>atagtgtaactgattcccaaaagcgaagggaaat<br>tcttcaaggaggccttcctacaggaaaattttg<br>aatgacttatcttctgatgcaccaggagtgccaa<br>ggattgaagaagagaagtctgaagaggagacttc<br>agca | PKA | 105<br>106 | Montminy M (1997).<br>Annu.Rev. Biochem.<br>66:807-822 |
| ATF-1<br>X55544 | L S E S E E S Q D S S<br>D S I G S S Q Q A H G I<br>L A R R P S Y R K I L K<br>D L S S E D T R G R K G<br>D G E N S G V S A A V<br>ttatcagaaagtgaggagtcccaggactcatccg<br>acagcataggctcctcacagaaagcccacgggat<br>cctagcacggcgcccatcttacagaaaaattttg<br>aaagacttatcttctgaagatacacggggcagaa<br>aaggagacggagaaaattctggagtttctgctgc<br>tgtc | PKA | 107<br>108 | Montminy M (1997).<br>Annu.Rev. Biochem.<br>66:807-822 |
| CREM<br>Z15159 | I A E T D D S A D S E<br>V I D S H K R R E I L S<br>S R R P S Y R K I L N E<br>L S S D V P G I P K I E<br>E E K S E E E G T P<br>attgcagagacagatgaatctgcagaatcagaag<br>gtgtaattgattctcataaacgtagagaaatcct<br>ttcacgaagaccctcttataggaaaatactgaat<br>gaactgtcctctgatgtgcctggtgttcccaaga<br>ttgaagaagagatcagaggaagaaggaacacc<br>a | PKA | 109<br>110 | Montminy M (1997).<br>Annu.Rev. Biochem.<br>66:807-822 |

Figure 3E

| | | | |
|---|---|---|---|
| PKB/Akt, PRK1, PRK2, PKCe, RSK1-4, MSK1-2, p70S6K, SGK | F K T F<br>Tttaaaactttc (Y15056 Human Akt/PKB) | PDK1 | 111<br>112 | Balendran et al., (2000) J Biol Chem 275:20806-20813; Frodin et al., (2000) EMBO J 19:2924-2934 |
| E2F-1<br>NM_005225 | C R P L<br>tgtcgtccttta | cyclinA-cdk2, cyclinE-cdk2 | 113<br>114 | Adams et al., (1996) Mol Cell Biol 16:6623-6633 |
| p73<br>AH006898 | Proline rich motif<br>P P R P<br>cctccccgccct | c-Abl | 115<br>116 | Agami et al., (1999) Nat 399:809-813 |
| p73<br>AH006898 | p73^{311-499}<br>Q Q A L N E S S A K N G A A S K R<br>A F K Q S P P A V P A L G A G V K<br>K R R H G D E D T Y Y L Q V R G R<br>E N F E I L M K L K E S L E L M E<br>L V P Q P L V D S Y R Q Q Q Q L L<br>Q R P S H L Q P P S Y G P V L S P<br>M N K V H G G M N K L P S V N Q L<br>V G Q P P P H S S A A T P N L G P<br>V G P G M L N N H G H A V P A N G<br>E M S S S H S A Q S M V S G S H C<br>T P P P P Y H A D P S L V S<br>cagcaggccctgaacgagagctccgccaagaacg<br>gggccgccagcaagcgtgccttcaagcagagccc<br>ccctgccgtccccgcccttggtgccggtgtgaag<br>aagcggcggcatggagacgaggacacgtactacc<br>ttcaggtgcgaggccgggagaactttgagatcct<br>gatgaagctgaaagagagcctggagctgatggag<br>ttggtgccgcagccactggtggactcctatcggc<br>agcagcagcagctcctacagaggccgagtcacct<br>acagcccccgtcctacgggccggtcctctcgccc<br>atgaacaaggtgcacgggggcatgaacaagctgc<br>cctccgtcaaccagctggtgggccagcctccccc<br>gcacagttcggcagctacacccaacctggggccc<br>gtgggccccgggatgctcaacaaccatggccacg<br>cagtgccagccaacggcgagatgagcagcagcca<br>cagcgcccagtccatggtctcggggtcccactgc<br>actccgccaccccctaccacgccgacccagcc<br>tcgtcagt | c-Abl | 117<br>118 | Yuan et al., (1999) Nat 399:814-817 |
| peptide library | PPPφPPPPφP (φ — hydrophobic) | c-Abl | 119 | Rickles et al., (1994) EMBO J 13:5598-5604 |
| peptide library | R / P L / V P P L / R P<br>aga/cct ctt/gtt cctccc tta/aga cca<br>("/" = or; an alternative a.a./n.a.) | Src | 120<br>121 | Kay et al., (2000) FASEB J 14:231-241 |

Figure 3F

| | | | |
|---|---|---|---|
| v-Abl<br>XM_033355 | v-Abl$^{858-1080}$<br>A L G T P A A A E P V T P T S K A<br>G S G A P G G T S K G P A E E S R<br>V R R H K H S S E S P G R D K G K<br>L S R L K P A P P P P P A A S A G<br>K A G G K P S Q S P S Q E A A G E<br>A V L G A K T K A T S L V D A V N<br>S D A A K P S Q P G E G L K K P V<br>L P A T P K P Q S A K P S G T P I<br>S P A P V P S T L P S A S S A L A<br>G D Q P S S T A F I P L I S T R V<br>S L R K T R Q P P E R I A S G A I<br>T K G V V L D S T E A L C L A I S<br>R N S E Q M A S H S A V L E A G K<br>N L Y T F C V S Y V D S I Q Q M R<br>N K F A F R E A I N K L E N N L R<br>gccttagggacccctgctgcagctgagccagtga<br>cccccaccagcaaagcaggctcaggtgcaccagg<br>gggcaccagcaagggccccgccgaggagtccaga<br>gtgaggaggcacaagcactcctctgagtcgccag<br>ggagggacaaggggaaattgtccaggctcaaacc<br>tgccccgccgccccaccagcagcctctgcaggg<br>aaggctggaggaaagccctcgcagagcccgagcc<br>aggaggcggccggggaggcagtcctgggcgcaaa<br>gacaaaagccacgagtctggttgatgctgtgaac<br>agtgacgctgccaagcccagccagccgggagagg<br>gcctcaaaaagcccgtgctcccggccactccaaa<br>gccacagtccgccaagccgtcggggaccccccatc<br>agcccagcccccgttccctccacgttgccatcag<br>catcctcggccctggcaggggaccagccgtcttc<br>caccgccttcatccctctcatatcaacccgagtg<br>tctcttcggaaaacccgccagcctccagagcgga<br>tcgccagcggcgccatcaccaagggcgtggtcct<br>ggacagcaccgaggcgctgtgcctcgccatctct<br>aggaactccgagcagatggccagccacagcgcag<br>tgctggaggccggcaaaaacctctacacgttctg<br>cgtgagctatgtggattccatccagcaaatgagg<br>aacaagtttgccttccgagaggccatcaacaaac<br>tggagaataatctccgg | JAK1 | 122<br><br><br><br><br><br><br><br><br><br><br><br><br><br><br>123 | Danial et al., (1990) Mol<br>Cell Biol 18:6795-6804 |
| IFNR β2<br>J03143 | IFNR β2$^{300-346}$<br>E S K Y V S L I T S Y Q P F S L E<br>K E V V C E E P L S P A T V P G M<br>H T E D N P G K V E H T<br>gaatcaaaatatgtatcactcatacgtcatacc<br>agccattttccttagaaaaggaggtggtctgtga<br>agagccgttgtctccagcaacagttccaggcatg<br>cataccgaagacaatccaggaaaagtggaacata<br>ca | JAK1 | 124<br><br><br>125 | Domanski et al., (1997)<br>J Biol Chem 272:26388-<br>26393 |
| GH, EPO<br>(NM_00079)<br>gp130 | box-1 motif<br>P A T P E P<br>cccgccactcctgaaccc (human<br>EPO, (NM_00079) | JAK2 | 126<br>127 | Tanner et al., (1995) J<br>Biol Chem 270:6523-<br>6530 |
| AT1<br>M93394 | Y I P P<br>tatattccccca | JAK2 | 128<br>129 | Ali et al., (1997) J Biol<br>Chem 272:23383-<br>23388 |

Figure 3G

| | JAK2 1-393 | | | |
|---|---|---|---|---|
| | M G M A C L T M T E M E G T S T S S I<br>Y Q N G D I S G N A N S M K Q I D P V<br>L Q V Y L Y H S L G K S E A D Y L T F<br>P S G E Y V A E E I C I A A S K A C G<br>I T P V Y H N M F A L M S E T E R I W<br>Y P P N H V F H I D E S T R H N V L Y<br>R I R F Y F P R W Y C S G S N R A Y R<br>H G I S R G A E A P L L D D F V M S Y<br>L F A Q W R H D F V H G W I K V P V T<br>H E T Q E E C L G M A V L D M M R I A<br>K E N D Q T P L A I Y N S I S Y K T F<br>L P K C I R A K I Q D Y H I L T R K R<br>I R Y R F R R F I Q Q F S Q C K A T A<br>R N L K L K Y L I N L E T L Q S A F Y<br>T E K F E V K E P G S G P S G E E I F<br>A T I I I T G N G G I Q W S R G K H K<br>E S E T L T E Q D L Q L Y C D F P N I<br>I D V S I K Q A N Q E G S N E S R V V<br>T I H K Q D G K N L E I E L S S L R E<br>A L S F V S L I D G Y Y R L T A D A H<br>H Y L C K E V A P P A V L | | 130 | |
| JAK2<br>NM_004972 | atgggaatggcctgccttacgatgacagaaatggaggg<br>aacatccacctcttctatatcagaatggtgatattt<br>ctggaaatgccaattctatgaagcaaatagatccagtt<br>cttcaggtgtatctttaccattcccttgggaaatctga<br>ggcagattatctgacctttccatctggggagtatgttg<br>cagaagaaatctgtattgctgcttctaaagcttgtggt<br>atcacacctgtgtatcataatatgtttgctttaatgag<br>tgaaacagaaaggatctggtatccacccaaccatgtct<br>tccatatagatgagtcaaccaggcataatgtactctac<br>agaataagattttacttcctcgttggtattgcagtgg<br>cagcaacagagcctatcggcatggaatatctcgaggtg<br>ctgaagctcctcttcttgatgactttgtcatgtcttac<br>ctctttgctcagtggcggcatgattttgtgcacggatg<br>gataaaagtacctgtgactcatgaaacacaggaagaat<br>gtcttgggatggcagtgttagatatgatgagaatagcc<br>aaagaaaacgatcaaacccactggccatctataactc<br>tatcagctacaagacattcttaccaaaatgtattcgag<br>caaagatccaagactatcatattttgacaaggaagcga<br>ataaggtacagatttcgcagatttattcagcaattcag<br>ccaatgcaaagccactgccagaaacttgaaacttaagt<br>atcttataaatctggaaactctgcagtctgccttctac<br>acagagaaatttgaagtaaaagaacctggaagtggtcc<br>ttcaggtgaggagattttttgcaaccattataataactg<br>gaaacggtggaattcagtggtcaagagggaaacataaa<br>gaaagtgagacactgacagaacaggatttacagttata<br>ttgcgatttcctaatattattgatgtcagtattaagc<br>aagcaaaccaagagggttcaaatgaaagccgagttgta<br>actatccataagcaagatggtaaaaatctggaaattga<br>acttagctcattaagggaagctttgtctttcgtgtcat<br>taattgatggatatatagattaactgcagatgcacat<br>cattacctctgtaaagaagtagcacctccagccgtgct<br>t | SHP-2 | 131 | Yin et al., (1997) J Biol<br>Chem 272:1032-1037 |

Figure 3H

| c-Jun, c-Myb, Stat1α, SREBPs, CREB P16220 | CREB (human P16220)<br>W W V Y D L L F<br>tgatgggtttatgatcttctcttt | CBP | 132<br>133 | Frangioni et al., (2000) Nat Biotech 18:1080-1085 |
|---|---|---|---|---|
| p53 (AH007665), E2F, TFIIB | F F E / D L D Y L<br>ttctttgaa/gatctcgactacctc (human p53 AH007665)<br>("/" = or; an alternative a.a.) | CBP/p300 | 134<br>135 | O'Connor et al., (1999) J Virol 73:3574-3581 |
| E2F1 BC005098 | L D Y H F G L E E G E<br>G I R D L F D C D F G D<br>L T P L D F<br>ctcgactaccacttcggcctcgaggagggcgagg<br>gcatcagagacctcttcgactgtgactttgggga<br>cctcaccccctggatttc | CBP | 136<br>137 | Fry et al., (1999) J Biol Chem 274:15883-15891 |

Figure 3I

| Rb M33647 | Rb^379-928<br>gcacacctgcagaatgagtatgaactcatgagagacaggcat<br>ttggaccaaattatgatgtgttccatgtatggcatatgcaaag<br>tgaagaatatagaccttaaattcaaaatcattgtaacagcata<br>caaggatcttcctcatgctgttcaggagacattcaaacgtgtt<br>ttgatcaaagaagaggagtatgattctattatagtattctata<br>actcggtcttcatgcagagactgaaaacaaatattttgcagta<br>tgcttccaccaggcccctaccttgtcaccaatacctcacatt<br>cctcgaagcccttacaagtttcctagttcacccttacggattc<br>ctggagggaacatctatattN T I Q Q L M M I L N S<br>A S D Q P S E N L I S Y F N N C T V N P K E<br>S I L K R V K D I G Y I F K E K F A K A V G<br>Q G C V E I G S Q R Y K L G V R L Y Y R V M<br>E S M L K S E E E R L S I Q N F S K L L N D<br>N I F H M S L L A C A L E V V M A T Y S R S<br>T S Q N L D S G T D L S F P W I L N V L N L<br>K A F D Y K V I E S F I K A E G N L T R E<br>M I K H L E R C E H R I M E S L A W L S D S<br>P L F D L I K Q S K D R E G P T D H L E S A<br>C P L N L P L Q N N H T A A D M Y L S P V R<br>S P K K G S T T R V N S T A N A E T Q A T<br>S A F Q T Q K P L K S T S L S L F Y K K V Y<br>R L A Y L R L N T L C E R L L S E H P E L E<br>H I I W T L F Q H T L Q N E Y E L M R D R H<br>L D Q I M M C S M Y G I C K V K N I D L K F<br>K I I V T A Y K D L P H A V Q E T F K R V L<br>I K E E E Y D S I I V F Y N S V F M Q R L K<br>T N I L Q Y A S T R P P T L S P I P H I P R<br>S P Y K F P S S P L R I P G G N I Y I S P L<br>K S P Y K I S E G L P T P T K M T P R S R I<br>L V S I G E S F G T S E K F Q K I N Q M V C<br>N S D R V L K R S A E G S N P P K P L K K L<br>R F D I E G S D E A D G S K H L P G E S K F<br>Q Q K L A E M T S T R T R M Q K Q K M N D S<br>M D T S N K E E K<br>aacactatccaacaattaatgatgatttaaattcagcaagtg<br>atcaaccttcagaaaatctgatttcctattttaacaactgcac<br>agtgaatccaaaagaaagtatactgaaaagagtgaaggatata<br>ggatacatctttaaagagaaatttgctaaagctgtgggacagg<br>gttgtgtcgaaattggatcacagcgatacaaacttggagttcg<br>cttgtattaccgagtaatggaatccatgcttaaatcagaagaa<br>gaacgattatccattcaaaattttagcaaacttctgaatgaca<br>acattttcatatgtctttattggcgtgcgctcttgaggttgt<br>aatggccacatatagcagaagtacatctcagaatcttgattct<br>ggaacagatttgtctttcccatggattctgaatgtgcttaatt<br>taaaagcctttgatttttacaaagtgatcgaaagttttatcaa<br>agcagaaggcaacttgacaagagaaatgataaaacatttagaa<br>cgatgtgaacatcgaatcatggaatcccttgcatggctctcag<br>attcacctttatttgatcttattaaacaatcaaaggaccgaga<br>aggaccaactgatcaccttgaatctgcttgtcctcttaatctt<br>cctctccagaataatcacactgcagcagatatgtatctttctc<br>ctgtaagatctccaaagaaaaaaggttcaactacgcgtgtaaa<br>ttctactgcaaatgcagagacacaagcaacctcagccttccag<br>acccagaagccattgaaatctacctctcttttcactgttttata<br>aaaaagtgtatcggctagcctatctccggctaaatacactttg<br>tgaacgccttctgtctgagcacccagaattagaacatatcatc<br>tggaccctttttccatcacccctgaagagtccatataaaatttc<br>agaaggtctgccaacaccaacaaaaatgactccaagatcaaga<br>atcttagtatcaattggtgaatcattcgggacttctgagaagt<br>tccagaaaataaatcagatggtatgtaacagcgaccgtgtgct<br>caaaagaagtgctgaaggaagcaaccctcctaaaccactgaa<br>aaactacgctttgatattgaaggatcagatgaagcagatggaa<br>gtaaacatctcccaggagagtccaaatttcagcagaaactggc<br>agaaatgacttctactcgaacacgaatgcaaaagcagaaaatg<br>aatgatagcatggatacctcaaacaaggaagagaaa | HDAC | 138<br><br><br><br><br><br><br><br><br><br><br><br><br><br><br><br><br><br><br><br><br><br><br><br><br><br><br><br><br><br><br>139 | Brehm et al., (1998)<br>Nature 391:597-600;<br>Magnaghi-Jaulin et al.,<br>(1998) Nature 391:601-605 |

Figure 3J

| | | | | | | | | | | | | | | |
|---|---|---|---|---|---|---|---|---|---|---|---|---|---|---|
| IκBα | DSGφXS (φ – hydrophobic) | | | | | | | | | | β-TrCP | | 140 | Yaron et al., (1997) EMBO J 16:6484-6494 |
| p53 K03199 | P W ccccctctgagtc ggaaactactt | P K | L L | S L | Q | E | T | F | S | D | L agg MDM2 | aaacattttcagacctat | 141 142 | Kussie et al., (1996) Science 174:949-953 |
| MDM2 AF092844 | G V R C P ggtgcacaaaa ttcttttttat acgattatatg aagcaacaaca ttctaggagat tgtgaaagagc | A L L S S agac cttg atga ttgt ttgt acag | Q F Y N F actt ccca tt att ttgg gaaa | K Y D D V atact gtat gtat cgtg atat | D L E L K atg attat cgta ccaa a | T G Q G E aaaga gact ttgta | Y Y Q D H gg aa ag tta | M I H L R ttgt ttca gctt | K M V F K tc ctc | E T Y G I | Y p53 | | 143 144 | Momand (2000) Gene 242:15-29 |

Figure 4: Examples of Nuclear Localization Signals and Nuclear Export Signals

| Parent Protein Name | Sequence | SEQ ID NO. | Reference |
|---|---|---|---|
| Monopartite Nuclear Localization Signals (NLS) | | | |
| SV40 Large T-antigen | PKKKRKV | 145 | Jans et al., 2000 BioEssays 22:532-544 |
| NFkB p50 | QRKRQK | 146 | Jans et al., 2000 BioEssays 22:532-544 |
| NFkB p65 | HRIEEKRKRTYETFDKSI | 147 | Jans et al., 2000 BioEssays 22:532-544 |
| LEF-1 | KKKKRKREK | 148 | Jans et al., 2000 BioEssays 22:532-544 |
| Dorsal | RRKRQK | 5 | Jans et al., 2000 BioEssays 22:532-544 |
| c-Myc | PAAKRVKLD | 149 | Jans et al., 2000 BioEssays 22:532-544 |
| APC NLS1 | GKKKKP | 150 | Zhang et al., 2000 PNAS 97:12577-12582 |
| APC NLS2 | PKKKKP | 151 | Zhang et al., 2000 PNAS 97:12577-12582 |
| Bipartite NLS | | | |
| Rb | KR-11 a a –KKLR | 152 | Jans et al., 2000 BioEssays 22:532-544 |
| DNA helicase Q1 | KK-15 a a –KKRK | 153 | Jans et al., 2000 BioEssays 22:532-544 |
| NES – Nuclear Export Signal | | | |
| IkBa | CIQQQLGQLTLENL | 154 | Jans et al., 2000 BioEssays 22:532-544 |
| PKIa | ELALKLAGLDI | 155 | Jans et al., 2000 BioEssays 22:532-544 |
| HIV Rev | LQLPPLERLTL | 156 | Jans et al., 2000 BioEssays 22:532-544 |
| MAPKK | ALQKKLEELELD | 157 | Jans et al., 2000 BioEssays 22:532-544 |
| hNet | TLWQFLLHLLLD | 158 | Ducret et al., 1999 Mol. Cell Biol. 19:7076-7087 |

Figure 5: Further Nuclear Localization Signals (NLS)

| Protein & Accession # | NLS | SEQ ID NO. | Reference |
|---|---|---|---|
| HCDA AF061655 | K R P A C T L K P E C VQ Q L L V C S Q E A K K | 159 | Somasekaram et al (1999) JBC: 274: 28405-28412 |
| | aagcgtcctgcctgcaccctgaagcctgagtgtgtccagcagc tgctggtttgctcccaggaggccaagaag | 160 | |
| TR2 NM_003297 | K D C I I N K H H R N R CQ Y C R L Q R | 161 | Yu etal (1998) J. Endocrinology, 159: 53-60 |
| | aaggattgtattattaataagcaccaccgaaaccgctgtcaat actgcaggttacagaga | 162 | |
| Hum-KU70 J04611 | K V T K R K H D N E G S G S K R P K | 163 | Koike etal (1999) Exp.Cell Res. 250: 401-413 |
| | aaagttaccaagagaaaacacgataatgaaggttctggaagca aaggcccaag | 164 | |
| Hglu.cort M10901 | R K C L Q A G M N L E A R K T K K | 165 | Kaneko etal (1997) Biochem.Biophys.Re s.Commun. 240: 348-353 |
| | cgaaaatgtcttcaggctggaatgaacctggaagctcgaaaaa caaagaaa | 166 | |
| Human c-Jun J04111 | K R M R N R I A A S K C R K R K L | 167 | Kaneko etal (1997) Biochem.Biophys.Re s.Commun. 240: 348-353 |
| | aagcgcatgaggaaccgcatcgctgcctccaagtgccgaaaaa ggaagctg | 168 | |
| HDNAtopoII NM_001067 | K K Q T T L A F K P I K K G K K R | 169 | Kaneko etal (1997) Biochem.Biophys.Re s.Commun. 240: 348-353 |
| | aagaaacaaactacattggcatttaagccaatcaaaaaggaa agaagaga | 170 | |
| HDNAtopoII NM_001068 | R K E W L T N F M E D R R Q R R L | 171 | Kaneko etal (1997) Biochem.Biophys.Re s.Commun. 240: 348-353 |
| | agaaaagaatggttaacaaatttatggaagaccggagacagc gtaggcta | 172 | |
| HARNT NM_001668 | R A I K R R P G L D F D D D G E G N S K F L R | 173 | Eguchi etal. (1977) JBC 272: 17640-17647 |
| | agggctattaagcggcgaccagggctggattttgatgatgatg gagaagggaacagtaaatttttg agg | 174 | |
| HBLM U39817 | R K R K K M P A S Q R S K R R K T A | 175 | Kaneko etal (1997) Biochem.Biophys.Re s.Commun. 240: 348-353 |
| | aggaagaggaaaaagatgccagcctcccaaaggtctaagagga gaaaaactgct | 176 | |
| Opaque 2 M29411 | M P T E E R V R K R K E S N R E S A R R S R Y R K A A H L K | 177 | Hicks and Raikhel (1995) PNAS 92: 734-738 |
| | atgcctaccgaggaaagagtgaggaaaagaaaggaatccaata gagaatcagccagacgctcgagatacaggaaagccgctcacct gaaa | 178 | |

Figure 6A: Further Experimentally Verified NLS Motifs (see Murat Cokol, Raj Nair & Burkhard Rost 2000 EMBO Reports1:411-415 and Jans, Xiao, & Lam 2000 Bioessays 22:532-544)

| NLS | SEQ ID NO. | Protein | Reference |
|---|---|---|---|
| RRMKWKK | 179 | PDX-1 | Moede et al., 1999 |
| RVHPYQR | 180 | QKI-5 | Wu et al., 1999 |
| KRPACTLKPECVQQLLVCSQEAKK | 181 | HCDA | Somasekaram et al., 1999 |
| PKKKRKV | 182 | SV40 | LrgT Kalderon et al., 1984 |
| GKKRSKA | 183 | H2B | Moreland et al., 1987 |
| KAKRQR | 184 | v-Rel | Gilmore and Temin, 1988 |
| RGRRRRQR | 185 | Amida | Irie et al., 2000 |
| RKRRR | 186 | Amida | Irie et al., 2000 |
| PPVKRERTS | 187 | RanBP3 | Welch et al., 1999 |
| PYLNKRKGKP | 188 | Pho4p | Welch et al., 1999 |
| CYGSKNTGAKKRKIDDA | 189 | DNAhelicaseQ1 | Miyamoto et al., 1997 |
| KKKKRKREK | 190 | LEF-1 | Prieve et al., 1998 |
| KKKRRSREK | 191 | TCF-1 | Prieve et al., 1998 |
| Krx{7,9}PQPKKKP | 192 | p53-NLS1 | Liang and Clarke, 1999 |
| KVTKRKHDNEGSGSKRPK | 193 | Hum-Ku70 | Koike et al., 1999 |
| RLKKLKCSKx{19}KTKR | 194 | GAL4 | Chan et al., 1998 |
| RKRIREDRKx{18}RKRKR | 195 | TCPTP | Chan et al., 1998 |
| RRERx{4}RPRKIPR | 196 | BDV-P | Schwemmle et al., 1999 |
| KKKKKEEEGEGKKK | 197 | act/inh betaA | Blauer et al., 1999 |
| PRPRKIPR | 198 | BDV-P | Shoya et al., 1998 |
| PPRIYPQLPSAPT | 199 | BDV-P | Shoya et al., 1998 |
| KDCVINKHHRNRCQYCRLQR | 200 | TR2 | Yu et al., 1998 |
| Krx{9}KTKK | 201 | THOV NP | Weber et al., 1998 |
| APKRKSGVSKC | 202 | PolyomaVP1 | Chang et al., 1992 |

Figure 6B

| | | | |
|---|---|---|---|
| RKKRRQRRR | 203 | HIV-1 Tat | Truant et al., 1999 |
| RQARRNRRRRWR | 204 | HIV-1 Rev | Truant et al., 1999 |
| MPKTRRRPRRSQRKRPPT | 205 | Rex | Palmeri and Malim, 1999 |
| KRPMNAFIVWSRDQRRK | 206 | SRY | Sudbeck and Scherer, 1997 |
| PRRRK | 207 | SRY | Sudbeck and Scherer, 1997 |
| KRPMNAFMVWAQAARRK | 208 | SOX9 | Sudbeck and Scherer, 1997 |
| PRRRK | 209 | SOX9 | Sudbeck and Scherer, 1997 |
| [KAR]TPIQKHWRPTVLTEGPPVKI RIETGEWE[KA] | 210 | ASVintegrase | Kukolj G. 1998 |
| PPRKKRTVV | 211 | NS5A | Ide et al., 1996 |
| YKRPCKRSFIRFI | 212 | DNAse EBV | Liu et al., 1998 |
| LKDVRKRKLGPGH | 213 | DNAse EBV | Lyons et al., 1987 |
| KRPRP | 214 | AdenovE1a | Bouvier and Baldacci, 1995 |
| RKRKK | 215 | YstDNApolalpha | Hsieh et al., 1998 |
| RRSMKRK | 216 | hVDR | Vihinen-Ranta et al., 1997 |
| PAKRARRGYK | 217 | CPV capsid | Kaneko et al., 1997 |
| RKCLQAGMNLEARKTKK | 218 | hGlu.cort. | Kaneko et al., 1997 |
| RRERNKMAAAKCRNRRR | 219 | CFOS | Kaneko et al., 1997 |
| KRMRNRIAASKCRKRKL | 220 | CJUN | Kaneko et al., 1997 |
| KKSKKGRQEALERLKKA | 221 | HDNApolalpha | Kaneko et al., 1997 |
| RKEWLTNFMEDRRQRKL | 222 | HDNAtopoII | Kaneko et al., 1997 |
| KKQTTLAFKPIKKGKKR | 223 | HDNAtopoII | Kaneko et al., 1997 |
| RKRKKMPASQRSKRRKT | 224 | HBLM | Kaneko et al., 1997 |
| RAIKRRPGLDFDDDGEGNSKFLR | 225 | HARNT | Eguchi et al., 1997 |
| SxGTKRSYx{2}M | 226 | InfluenzaNP | Wang et al., 1997 |
| TKRSx{3}M | 227 | InfluenzaNP | Wang et al., 1997 |
| RIRKKLR | 228 | P54 | Mizuno et al., 1996 |

Figure 6C

| | | | |
|---|---|---|---|
| KRAAEDDEDDDVDTKKQK | 229 | HProTalpha | Rubstov et al., 1997 |
| GRKRKKRT | 230 | Tst1/Oct6 | Sock et al., 1996 |
| KKKQKK | 231 | 20Sproteasome | Knuehl et al., 1996 |
| REKKEKEQKEKCA | 232 | prot.Hsc9 | Nederlof et al., 1995 |
| LEKKVKKKFDWCA | 233 | prot.Hsci | Nederlof et al., 1995 |
| TEKK[QG]KSILYDCA | 234 | prot.Hsc3 | Nederlof et al., 1995 |
| SDKKVRSRLIECATa | 235 | alpha | Nederlof et al., 1995 |
| LKRKLQR | 236 | Pax-QNR | Carriere et al., 1995 |
| RRKGKEK | 237 | Hunt.Dis.prot. | Bessert et al.,1995 |
| CKRKTTNADRRKA | 238 | MyoD | Vandromme et al., 1995 |
| VNEAFETLKRC | 239 | MyoD | Vandromme et al., 1995 |
| MPTEERVRKRKESNRESARRSRYRKAAHLK | 240 | Opaque2 | Hicks and Raikhel, 1995 |
| KVNSRKRRKEVPGPNGATEED | 241 | CTP | Wang et al., 1995 |
| PRRGPR | 242 | HCV | Chang et al., 1994 |
| PRGRRQPIPKARQP | 243 | HCV | Chang et al., 1994 |
| KRSAEGGNPPKPLKKLR | 244 | P110RB1 | Zacksenhaus et al., 1993 |
| KRKx{11}KKKSKK | 245 | hpoly(ADP)poly | Schreiber et al., 1992 |
| EYLSRKGKLEL | 246 | VirD2-Nterm | Tinland et al., 1992 |
| PKRPRDRHDGELGGRKRARG | 247 | VirD2-Cterm | Tinland et al., 1992 |
| KRPAATKKAGQAKKKK KRx{10}KKKL | 248 | Nucloplasmin | Robbins et al., 1991 Moore et al., 1999 JCB 144:213 |
| KRKKEMANKSAPEAKKKK | 249 | Nucleolin | Schmidt-Zachmann & Nigg, 1993 |
| RKRAFHGDDPFGEGPPDKK | 250 | ICP-8 | Gao and Knipe, 1992 |
| GGGx{3}KNRRx{6}RGGRN | 251 | Nab2 | Truant et al., 1998 |

Figure 6D

| | | | |
|---|---|---|---|
| YNNQSSNFGPMKGGN | 252 | M9 | Bonifaci et al., 1997 |
| PAAKRVKLD | 253 | LscMyc | Welch et al. 1999 |
| KRPAEDMEEEQAFKRSR | 254 | HumKprotein | Michael et al., 1997 |
| SxGTKRSYxxM | 255 | FluA | Weber et al., 1998 |
| MNKIPIKDLLNPG | 256 | Mat-alpha | Hall et al., 1984 |
| PKKARED | 257 | polyoma Lrg-T | Richardson et al., 1986 |
| VSRKRPR | 258 | polyoma Lrg-T | Richardson et al., 1986 |
| APTKRKGS | 259 | SV40 VP1 | Wychowski et al., 1986 |
| PNKKKRK | 260 | SV40 VP2 | Wychowski et al., 1987 |
| EEDGPQKKKRRL | 261 | polyoma VP2 | Chang et al., 1992 |
| PLLKKIKQ | 262 | c-myb | Dang and Lee, 1989 |
| PPQKKIKS | 263 | N-myc | Dang and Lee, 1989 |
| PQPKKKP | 264 | P53 | Dang and Lee, 1989 |
| SKRVAKRKL | 265 | c-erb-A | Dang and Lee, 1989 |
| IKYFKKFPKD | 266 | yeast SKI3 | Rhee et al., 1989 |
| KTRKHRG | 267 | L29 | Underwood and Fried, 1990 |
| KHRKHPG | 268 | L29 | Underwood and Fried, 1990 |
| PQSRKKLR | 269 | Max | Kato et al., 1992 |
| HRKYEAPRHx{6}PRKR | 270 | L3 | Moreland et al., 1985 |
| KKEKKKSKK | 271 | Dyskerin | Youssoifan et al., 1999 |
| RRRX{11}KRRK | 272 | CBP80 | Miyamoto et al., 1997 JBC 272:26374 |
| KKx{15}KKRK CYFQKKAANMLQQSGSKNTGAK KRK | 273 | DNA helicase Q1 | Miyamoto et al., 1997 JBC 272:26374 Seki et al., 1997 BBRC 234:48 |
| KRKRRP | 274 | BRCA1 | Chen et al., 1996 JBC 271:32863 Li et al., 1998 JBC 273:6183 |

Figure 6E

| | | | |
|---|---|---|---|
| PKKNRLRRK | 275 | BRCA1 | Chen et al., 1996 JBC 271:32863 Li et al., 1998 JBC 273:6183 |
| KRQRx{19}KKSKK | 276 | Mitosin | Li et al., 1998 JBC 273:6183 |
| PAAKRVKLD | 277 | Myc | Nadler et al., 1997 JBC 272:4310 |
| QRKRQK | 278 | NFkB p50 | Nadler et al., 1997 JBC 272:4310 |
| HRIEEKRKRTYETFKSI | 279 | NFkB p65 | Nadler et al., 1997 JBC 272:4310 |
| KKKYKLK | 280 | HIV1422 | Nadler et al., 1997 JBC 272:4310 |
| KSKKKAQ | 281 | HIV1423 | Nadler et al., 1997 JBC 272:4310 |
| LKRPRSPSS | 282 | EBNA1 | Fischer et al., 1997 JBC 272:3888 |
| KRKx{22}KELQKQITK | 283 | HIV IN | Gallay et al., 1997 PNAS 94:9825 |
| GKKKYKLKH | 284 | HIV MA | Gallay et al., 1996 J Virol 70:1027 |
| RKKRKx{9}KAKKSK | 285 | N1N2 | Hu & Jans 1999 JBC 274:15820 |
| KRx{11}KKLR | 286 | RB | Efthymiadis et al., 1997 JBC 272:22134 |
| RRPSx{22}RRKRQK | 287 | Dorsal + PKA site | Briggs et al., 1998 JBC 273:22745 |

NLS motif: motif found, notation: '[KR]' used as 'K or R', i.e. any of the two amino acids valid at that position, 'x' for 'any amino acid', 'x{9}' for '9 times x', and 'x{7,9}' for 'at least 7, at most 9 times x' ; Protein: names taken from original; Reference: publication of NLS.

Figure 7: Detection Domains

| Signal | Sequence | SEQ ID NO. | Reference |
|---|---|---|---|
| Epitope tags in general | | | Kolodziej and Young. 1991. Methods Enzymol. 194:508-19. |
| FLAG epitope | DYKDDDDK | 288 | Kasir, et al., 1999. J Biol Chem. 274:24873-80. |
| | GACTACAAAGACGACGACGACAAA | 289 | |
| HA epitope | YPYDVPDYA | 290 | Smith, et al., 1999. J Biol Chem. 274:19894-900. |
| | TACCCATACGACGTACCAGACTACGCA | 291 | |
| KT3 epitope | PPEPET | 292 | MacArthur and Walter. 1984. J Virol. 52:483-91. |
| | CCACCAGAACCAGAAACA | 293 | |
| Myc epitope | AEEQKLISEEDL | 294 | Gosney, et al., 1990. Anticancer Res. 10:623-8. |
| | GCAGAAGAACAAAAATTAATAAGCGAAGAAGACTTA | 295 | |
| GFP | | | Tsien, R.Y. 1998. Annu Rev Biochem. 67:509-44. |
| Phycobiliproteins | | | White and Stryer. 1987. Anal Biochem. 161:442-52; Kronick, 1986. J Immunol Methods. 92:1-13 |

Figure 8: Examples of Protein-Derived Transport Peptides

| Parent Protein Name | Sequence | SEQ ID NO. | Reference |
|---|---|---|---|
| Tat 48-60 | GRKKRRQRRRPPQ | 296 | JBC 2001, 276 (5836) |
| Antennapedia | | | |
| Modified from Tat | YARAAARQARA | 297 | Cancer Research 2001, Jan 15, 61 (474) |
| Modified from Tat | L-RRRRRRRR | 298 | PNAS 2000, 97 (13003) |
| Modified from Tat | D-RRRRRRRR | 299 | PNAS 2000, 97 (13003) |
| VP22 | DAATATRGRSAASRPTERPRAPARSASRPRRPVE | 300 | Cell 88 (223) |
| Penetratin | GWTLNSAGYLLGLINLKALAALAKKIL | 301 | JBC 1994, 269 (10444) |
| PreS2 | PLSSIFSRIGDP | 302 | Gene Therapy 2000, 7 (750) |
| SN50 | AAVALLPAVLLALLAP | 303 | JBC 1995, 270 (14255) |
| Grb SH2 | AAVLLPVLLAAP | 304 | Nat Biotechnol. 1998, 16 (370) |
| Integrin | VTVLALGALAGVGVG | 305 | PNAS 1996, 93 (11819) |
| HIV gp41 | GALFLGWLGAAGSTMGAWSQP | 306 | Nucleic Acid Res 1997, 25 (2730) |
| Transportan | GWTLNSAGYLLGLINLKALAALAKKIL | 307 | FASEB 1998, 12 (67) |
| α-helical amphipathic model peptide | KLALKLALKALKAALKLA | 308 | J. Peptide Sci. 1999 5 (185) |
| Pep-1 | KETWWETWWTEWSQPKKKRKV | 309 | Nature Biotechnology, Vol 19, 2001 (1173) |

Figure 9: RNA Binding Domains

| Peptide | RNA Binding Domain Sequence | SEQ ID NO. |
|---|---|---|
| HIV rev (34-50) | TRQARRNRRRRWRERQR | 310 |
| λN (1-22) | (M/L)DAQTRRRERRAEKQAQWK | 311 |
| P22N (14-30) | NAKTRRHERRRKLAIER | 312 |
| HTLV-1 Rex peptide | MPKTRRRPRRSQRKRP | 313 |
| HIV Tat (48-60) | GRKKRRQRRRPPQ | 314 |

Figure 10: Further Nuclear Export Signals

| Source | Sequence | SEQ ID NO. | Reference |
|---|---|---|---|
| MEK1 | ALQKKLEELELDE | 315 | Fukuda, (1997) J. Biol. Chem 272, 51, 32642-32648 |
| MEK2 | DLQKKLEELELDE | 316 | Zheng and Guan, J. Biol. Chem. 268:11435-11439, 1993 |
| MAPKAP2 | DKERWEDVKEEMTSALATMRVDYE | 317 | Engel et al., 1998, EMBO J. 17:3363-3371 |
| STAT1 | WDRTFSLFQQLLQSSFVVE | 318 | Begitt et al., Proc. Natl. Acad. Sci. USA 97:10418-10423 |
| HIV-1 REV | LPPLERLTL | 319 | Mowen et al., 2000, Mol. Cell. Biol. 20:7273-7381 |
| PKI | LALKLAGLDI | 320 | Mowen et al., 2000, Mol. Cell. Biol. 20:7273-7381 |
| I-kappa-B | LQQQLGQLTL | 321 | Mowen et al., 2000, Mol. Cell. Biol. 20:7273-7381 |
| c-Abl | LESNLRELQI | 322 | Mowen et al., 2000, Mol. Cell. Biol. 20:7273-7381 |
| Ahr | LDKLSVLTLS | 323 | Ikuta et al., 1998, J. Biol. Chem. 273:2895-2904 |
| Net | LWQFLLQLLLD | 324 | Ducret, 1999, Mol. Cell. Biol. 19:7076-7087 |
| Cyclin B1 | LCQAFSKVILA | 325 | Ducret, 1999, Mol. Cell. Biol. 19:7076-7087 |

Figure 11A: Examples of Post-Translational Modification Sites

| Enzyme specificity Acc. No. | Enzyme Activity | Substrate Acc. No. | Post-translational Modification Site Sequence | SEQ ID NO. | Reference |
|---|---|---|---|---|---|
| ERK XM_036967 | Ser/Thr Phosphorylation | ELK-1 AB016194 | accctgagtcccattg cgccccgtagcccggc caagct<br>T L S P I A P R S P A K L | 340<br><br>341 | Jacobs et al., (1999) Genes & Dev 13:163-175 |
| JNK3/SAPKbeta U34820 | Ser/Thr Phosphorylation | SCG10 BC026538 | ttgaagccaccatctc ccatctcagaagctcc acgaactctagcttct ccaaag<br>L K P P S P I S E A P R T L A S P K | 342<br><br><br>343 | Neidhart et al., (2001) FEBS Lett 508:259-64 |
| PKA NP_002721 | Ser/Thr Phosphorylation | CREB X55545 | aggaggccttcctac<br>R R P S Y | 344<br>345 | Montminy M (1997). Annu.Rev. Biochem. 66:807-822 |
| PDK1 NM_011062 | Ser/Thr Phosphorylation | Akt/PKB Y15056 | tcattcgtgggaacag cgcagtacgtttctcc agagctgctcacg<br>S F V G T A Q Y V S P E L L T | 346<br><br><br>347 | Balendran et al., (2000) J Biol Chem 275:20806-20813; Frodin et al., (2000) EMBO J 19:2924-2934 |
| c-Abl M14752 | Tyr. Phosphorylation | c-Jun J04111 | gagccgccggtctacg caaacctcagc<br>E P P V Y A N L S | 348<br>349 | Barila et al., (2000) EMBO J 19:273-281 |
| c-Abl M14752 | Tyr. Phosphorylation | Peptide library | IYAXP<br>X = any amino acid | 350 | Till et al., (1999) J Biol Chem 19:4995-5003 |
| Jak1 NM_002227 Jak2 NM_004972 | Tyr. Phosphorylation | STAT1 XM_010893 | ggaactggatatatca agactgag<br>G T G Y I K T E | 351<br><br>352 | Quelle et al., (1995) J Biol Chem 270:207750-200780 |
| p300 U01877 | Acetylation | p53 AF135120 | cgccataaaaaa<br>R H K K | 353<br>354 | Fu et al., (2000) J Biol Chem 275:20853-20860 |
| P/CAF, CBP(U85962), p300 (U01877) | Acetylation | EF-1 NM_007891 | cacccagggaaaggtg tgaaatctccggggga gaagtcacgctat<br>H P G K G V K S P G E K S R Y | 355<br><br><br>356 | Martinez-Balbas et al., (2000) EMBO J 19:662-671; Marzio et al., (2000) J Biol Chem 275:10887-10892 |
| Farnesyl transferase NM_002028 Palmitoyl transferase NM_006415 | Farnesylation, palmitoylation | c-ras (H-ras) E01119 | tgcatgtcctgcaaat gcgttctgtct<br>C M S C K C V L S | 357<br>358 | Prior & Hancock (2001) J Cell Sci 114:1603-1608 |

Figure 11B

| Farnesyl transferase NM_002028 | Farnesylation | c-ras (H-ras) E01119 | tgcgttctgtct C  V  L  S | 359 360 | Prior & Hancock (2001) J Cell Sci 114:1603-1608 |
|---|---|---|---|---|---|
| Farnesyl transferase NM_002028 | Farnesylation | K-ras M54968 | tgtgtaattatg C  V  I  M | 361 362 | Prior & Hancock (2001) J Cell Sci 114:1603-1608 |

Figure 12A: PH (Plekstrin Homology domain) from PLC-beta2
(Wang et al, 2000, JBC 275: 7466-7469)

PLC-beta2[8-48]
BC009009

```
                              ctgcccccaaggtgaaggcc
                              L   P   P   K   V   K   A
    284 tatctgagccaaggggagcgcttcatcaaatgggatgatgaaact
        Y   L   S   Q   G   E   R   F   I   K   W   D   D   E   T
    329 acagttgcctctccagttatcctccgtgtggatcctaagggctac
        T   V   A   S   P   V   I   L   R   V   D   P   K   G   Y
    374 tacttatactggacgtatcaaagtaaggagatg        (SEQ ID NO:363)
        Y   L   Y   W   T   Y   Q   S   K   E   M    (SEQ ID NO:364)
```

Figure 12B: Diacylglycerol Binding Domain from Protein Kinase C
(Knofp et al., 1986, Cell 46: 491-502)

ACCESSION   NM_012628

```
cacaagttcaccgctcgtttcttcaagcag
H   K   F   T   A   R   F   F   K   Q
ccaaccttctgcagtcactgtaccgacttcatctggggcattgga
P   T   F   C   S   H   C   T   D   F   I   W   G   I   G
aagcagggcctgcaatgtcaagtctgcagctttgtggttcaccgc
K   Q   G   L   Q   C   Q   V   C   S   F   V   V   H   R
Cgatgccacgaatttgtgaccttcgagtgt              (SEQ ID NO:365)
R   C   H   E   F   V   T   F   E   C       (SEQ ID NO:366)
```

FUSION PROTEINS AND ASSAYS FOR MOLECULAR BINDING

CROSS REFERENCE

This application claims priority to U.S. Provisional Application Ser. No. 60/309,395 filed Aug. 1, 2001 and to U.S. Provisional Application Ser. No. 60/341,589 filed Dec. 13, 2001.

FIELD OF THE INVENTION

The invention relates to cell and molecular biology, recombinant DNA technology, and recombinant protein technology.

BACKGROUND

Interactions among molecules such as proteins are fundamental to cell biology. Protein binding to a wide variety of cellular components, including proteins, nucleic acids, carbohydrates, and lipids, has been recognized as an important drug target due to its integral nature within signal transduction and biological pathways. Such binding can be correlated to a variety of intracellular events, including protein expression, the availability of an active state of a protein, and, directly or indirectly, to protein catalytic activity. For instance, in the cytoplasm the protein kinase MAPK, when complexed with MEK1, is inactive. Upon activation, MEK1 and MAPK dissociate, leading to free, activated MAPK. Detection of the activated MAPK by virtue of its ability to bind to a binding domain in a target substrate indicates the presence of the active enzyme, and is indirectly related to the MAPK activity of phosphorylating substrates.

Current methods for analyzing cellular molecular binding events, such as two-hybrid systems and variants thereof, substrate complementation systems, immunoprecipitation assays, in vivo incorporation of radiolabeled moieties, and the use of antibodies specific for a given modification (such as phosphorylation), suffer from numerous drawbacks. Such drawbacks include the need to construct two or more chimeric proteins; the inability to monitor biochemical events in live, intact cells or in fixed cells; the requirement for considerable time to conduct the assays; and the need for specialized and expensive equipment. Thus, improved reagents and methods for detecting and measuring specific binding events are needed.

A very significant improvement would be a flexible design for reagents and assays that can be used to detect molecular binding events that occur within living cells. Such reagents would preferably comprise a single chimeric protein, and would be applicable to monitoring molecular binding events in live and fixed end point cell preparations as well as to making kinetic measurements of the binding events in cells. Such reagents would preferably possess detectable signals that permit easy detection of molecular binding events of interest, and also provide the ability to combine the molecular binding event assay with other cell-based assays.

SUMMARY OF THE INVENTION

The present invention fulfills the need in the art for novel reagents, and assays using such reagents, for detecting molecular binding events that do not suffer from the drawbacks of previous reagents and assays for the detection of molecular binding.

In one aspect, the present invention provides a recombinant fusion protein comprising a detection domain; a first localization domain; and a binding domain for the molecule of interest; wherein the detection domain, the first localization domain, and the binding domain for the molecule of interest are operably linked; wherein the binding domain for the molecule of interest is separated from the first localization domain by 0–20 amino acid residues; and wherein the first localization domain and the binding domain for the molecule of interest do not all occur in a single non-recombinant protein, or do not all occur in a single non-recombinant protein with the same spacing as in the recombinant fusion protein for detecting binding of a molecule of interest.

In a preferred embodiment, the recombinant fusion protein further comprises a second localization domain, wherein the binding domain for the molecule of interest is separated from the second localization domain by more than 20 amino acid residues; wherein the first localization domain and the second localization domain do not target the recombinant fusion protein to an identical subcellular compartment; and wherein the first localization domain, the second localization domain, and the binding domain for the molecule of interest do not all occur in a single non-recombinant protein, or do not all occur in a single non-recombinant protein with the same spacing as in the recombinant fusion protein.

In a further preferred embodiment, the binding site for the molecule of interest does not contain a "cleavage site," wherein "cleavage site" is defined as an amino acid sequence within the binding domain that is targeted for cleavage by a proteolytic enzyme.

In another aspect the invention provides recombinant nucleic acid molecules encoding a recombinant fusion protein for detecting binding of a molecule of interest, comprising the following operably linked regions in frame relative to each other: a first nucleic acid sequence encoding a detection domain; a second nucleic acid sequence encoding a first localization domain; and a third nucleic acid sequence encoding a binding domain for the molecule of interest; wherein the third nucleic acid sequence is separated from the second nucleic acid sequence by 0–60 nucleotides, and wherein the second nucleic acid sequence and the third nucleic acid sequence do not all occur in a single non-recombinant nucleic acid molecule, or do not all occur in a single non-recombinant nucleic acid molecule with the same spacing as in the recombinant nucleic acid molecule encoding a recombinant fusion protein for detecting binding of a molecule of interest.

In a preferred embodiment, the recombinant nucleic acid molecules further comprise a fourth nucleic acid sequence encoding a second localization domain, wherein the fourth nucleic acid sequence is separated from the third nucleic acid sequence by more than 60 nucleotides; wherein the first localization domain and the second localization domain do not target the recombinant fusion protein to an identical subcellular compartment; and wherein the second nucleic acid sequence, the third nucleic acid sequence, and the fourth nucleic acid sequence do not all occur in a single non-recombinant nucleic acid molecule, or do not all occur in a single non-recombinant nucleic acid molecule with the same spacing as in the recombinant nucleic acid molecule encoding the recombinant fusion protein.

In another aspect, the present invention provides recombinant nucleic acid molecules comprising the following operably linked regions in frame relative to each other: a first nucleic acid sequence encoding a detection domain; a second nucleic acid sequence encoding a first localization domain; and a third nucleic acid sequence that comprises one or more restriction enzyme recognition sites that are not present elsewhere in the recombinant nucleic acid molecule; wherein the third nucleic acid sequence is separated from the second nucleic acid sequence by 0–60 nucleotides; and wherein the second nucleic acid sequence and the third nucleic acid sequence do not both occur in a single non-recombinant nucleic acid molecule, or do not both occur in a single non-recombinant nucleic acid molecule with the same spacing as in the recombinant nucleic acid molecule.

In a preferred embodiment, the recombinant nucleic acid molecules further comprise a fourth nucleic acid sequence encoding a second localization domain, wherein the fourth nucleic acid sequence is separated from the third nucleic acid sequence by more than 60 nucleotides; wherein the first and second localization domains do not target the recombinant fusion protein to an identical subcellular compartment; and wherein the second nucleic acid sequence, the third nucleic acid sequence, and the fourth nucleic acid sequence do not all occur in a single non-recombinant nucleic acid molecule, or do not all occur in a single non-recombinant nucleic acid molecule with the same spacing as in the recombinant nucleic acid molecule.

In another aspect the invention provides recombinant expression vectors comprising the nucleic acid molecules of the invention, and cells transfected with such expression vectors.

In another aspect the invention provides kits containing the fusion proteins, the nucleic acid molecules, the expression vectors and/or the host cells of the invention, and instructions for their use in detecting the binding of a molecule of interest to the fusion protein in a cell.

In another aspect the invention provides methods for identifying compounds that alter the binding of a molecule of interest in a cell comprising providing cells that contain the recombinant fusion proteins of the invention, obtaining optically detectable signals from the detection domain, comparing the subcellular distribution of the recombinant fusion protein in the presence and absence of one or more test compounds, and identifying one or more compounds that alter the subcellular distribution of the recombinant fusion protein, wherein such altering of the subcellular distribution of the recombinant fusion protein indicates that the one or more test compounds have altered the binding of the molecule of interest to the recombinant fusion protein in the cells, and/or have altered the expression of the molecule of interest in the cells.

DESCRIPTION OF THE FIGURES

FIG. 2 is a table of subcellular compartment localization sequences.

FIG. 3 is a table of binding domains.

FIG. 4 is a table of nuclear localization signals and nuclear export signals.

FIG. 5 is a table of further nuclear localization signals.

FIG. 6 is a table of further experimentally verified nuclear localization signals.

FIG. 7 is a table of detection domains.

FIG. 8 is a table of protein-derived transport peptides.

FIG. 9 is a table of RNA binding domains.

FIG. 10 is a table of further nuclear export signals.

FIG. 11 is a table of post-translational modification sites.

FIG. 12A shows the sequence of the Plekstrin Homology (PH) domain from PLC-beta2.

FIG. 12B shows the sequence of the diacylglycerol binding domain (DBD) from protein kinase C.

DETAILED DESCRIPTION OF THE INVENTION

Figure 1:
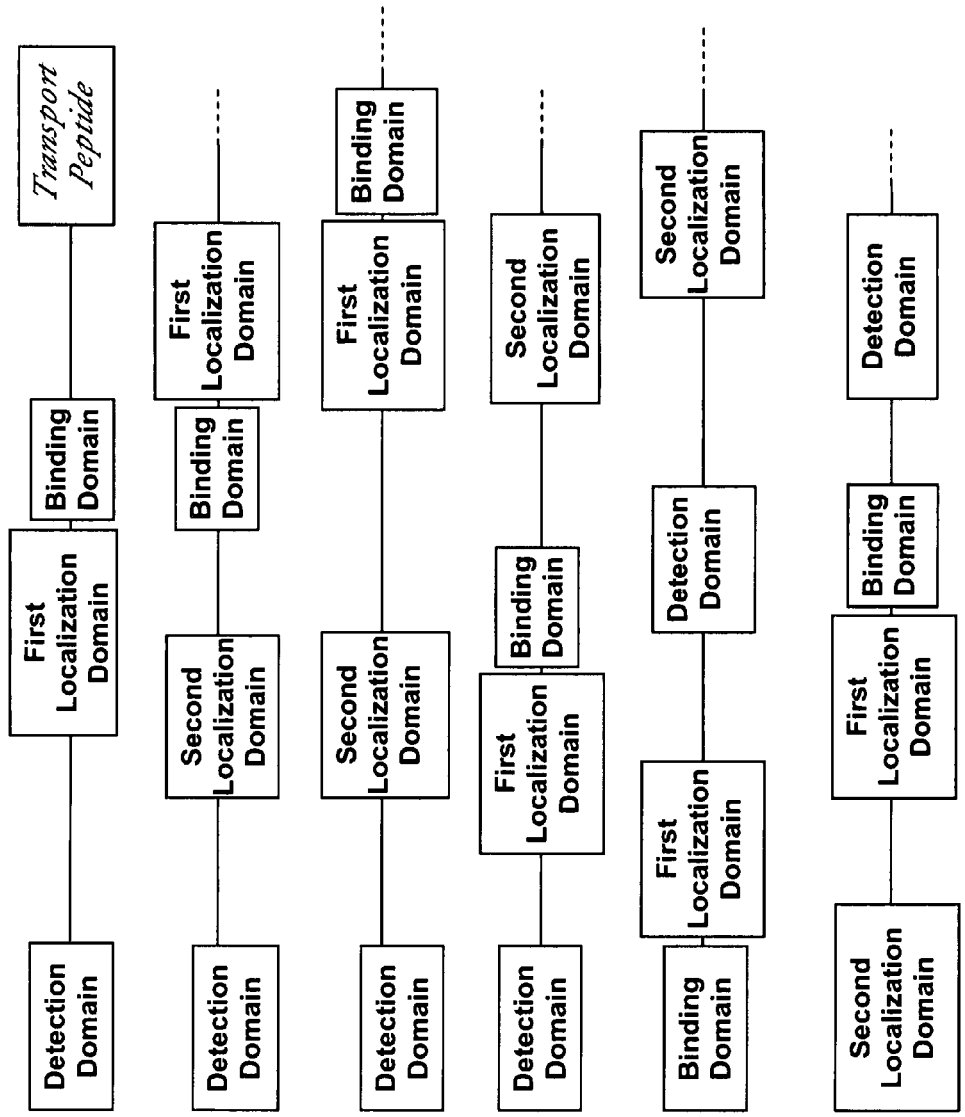
FIG. 1 is a pictoral depiction of various possible fusion protein arrangements.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols* (pp. 109–128, ed. E. J. Murray, The Humana Press Inc., Clifton, N.J.), and the Ambion 1998 Catalog (Ambion, Austin, Tex.).

In one aspect, the present invention provides fusion proteins for detecting binding of a protein of interest, comprising
 a) a detection domain;
 b) a first localization domain; and
 c) a binding domain for the molecule of interest;
 wherein the detection domain, the first localization domain, and the binding domain for the molecule of interest are operably linked;
 wherein the binding domain for the molecule of interest is separated from the first localization domain by 0–20 amino acid residues; and
 wherein the first localization domain and the binding domain for the molecule of interest do not both occur in a single non-recombinant protein, or do not both occur in a single non-recombinant protein with the same spacing as in the recombinant fusion protein for detecting binding of a molecule of interest.

In a preferred embodiment, the fusion protein further comprises a second localization domain, wherein the detection domain, the first localization domain, the second localization domain, and the binding domain for the molecule of interest are operably linked; wherein the binding domain for the molecule of interest is separated from the second localization domain by more than 20 amino acid residues; wherein the first localization domain and the second localization domain do not target the recombinant fusion protein to an identical subcellular compartment; and wherein the first localization domain, the second localization domain, and the binding domain for the molecule of interest do not all occur in a single non-recombinant protein, or do not all occur in a single non-recombinant protein with the same spacing as in the recombinant fusion protein for detecting binding of a molecule of interest.

As used herein, "separated by" means that the recited number of residues must be present between the domains, thus separating the domains.

As used herein, "binding of a molecule of interest" means binding of the molecule of interest to the binding domain. Binding may be by covalent or non-covalent interaction. Detection of such binding demonstrates that the molecule of interest has been expressed by the cells, and demonstrates that the molecule of interest is in a state capable of binding to the binding domain. Such binding may indicate that the molecule of interest has undergone a post-translational modification, such as a conformational change or phosphorylation, allowing such binding. Such binding may also indicate that the molecule of interest is active. Furthermore, such binding may indicate that the binding domain has undergone a covalent modification via an enzymatic reaction.

The molecule of interest can be any chemical or biological molecule capable of binding to the binding domain and thus inhibiting the activity of the first localization domain via steric hindrance. In a preferred embodiment, the binding domain comprises a binding domain for a molecule of interest selected from the group consisting of nucleic acid, protein, and lipid. In a most preferred embodiment, the binding domain comprises a binding domain for a protein of interest.

As used herein, "fusion protein" means a non-naturally occurring protein product, wherein the domains of the fusion protein are derived from one or more other proteins or artificially derived sequences. For example, each domain can be derived from a different naturally occurring protein sequence, or mutant/variant thereof, that possesses the desired properties. Alternatively, the domains can all be derived from a naturally occurring protein, wherein the spacing of the binding domain relative to the first and (if present) the second localization domains has been modified with respect to their spacing in the naturally occurring protein. Many other variations on this theme will be apparent to one of skill in the art.

The fusion protein may be constructed by a variety of mechanisms including, but not limited to, standard DNA manipulation techniques and chemical assembly via subunit parts of the fusion protein. The chemical assembly may lead to an equivalent form as the molecular genetic form or alternative associations with equivalent function. In a preferred embodiment, the fusion protein is produced by standard recombinant DNA techniques.

The basic principle of the fusion proteins of the present invention is that the distribution of the fusion protein changes upon being bound by the molecule of interest. The unbound fusion protein is distributed based on the subcellular distribution directed by the first localization domain (in the embodiment with only one localization domain), or based on the subcellular distribution between two subcellular compartments as directed by the first and second localization domains, respectively, in a ratio based upon the relative strengths of the first and the second localization domains. Thus, in the two localization domain embodiment, in the unbound state, there may be an equilibrium in the distribution of the fusion protein between the two targeted subcellular compartments, or either one or the other localization domain may bias the distribution of the fusion protein.

Upon binding of the molecule of interest to the binding domain of the fusion protein, the ability of the first localization domain to direct the fusion protein to the subcellular compartment normally targeted by the first localization domain is inhibited, due to steric hindrance caused by the proximity of the bound molecule of interest. Thus, the distribution of the fusion protein within the cell will be either without bias within the cell in the embodiment with only the first localization domain, or will be determined mainly by the second localization domain in the embodiment with both a first and second localization domain, reflecting in both cases a change in the distribution of the bound fusion protein within a cell, which can be detected by a change in the distribution of the detectable signal from the detection domain of the fusion protein within the cell.

The exact order of the domains in the fusion protein, as well as the presence and/or length of any other sequences located between the domains, is not generally critical, as long as: (a) the required spacing between the binding domain and the first localization domain and second localization domain (if present) are maintained; (b) the first and second localization domains function independently; and (c) the function of each domain is retained. Generally, this requires that the two-dimensional and three-dimensional structure of any intervening protein sequence does not preclude the binding or interaction requirements of the domains of the fusion protein, except as contemplated herein. One of skill in the art will readily be able to optimize the fusion protein for these parameters using the teachings herein. Examples of fusion protein arrangements may be found in FIG. 1.

As recited herein, for each domain it will be understood that more than one copy of the sequence that imparts the required function may be present. For example, as used herein, "localization domain" means an amino acid sequence that imparts a restriction on the cellular distribution of the fusion protein to a particular subcellular compartment of the cell. Thus, the first localization domain and the second localization domain may each individually comprise 1, 2, or more such amino acid sequences that impart a restriction on the cellular distribution of the fusion protein.

The first and second localization domains do not target the recombinant fusion protein to the identical subcellular compartment. In the unbound state, the fusion protein will distribute between the two subcellular compartments targeted by the first and second localization domains as described above. For example, where the first localization domain comprises a nuclear localization signal (NLS) with an adjacent binding domain, and the second localization domain comprises a nuclear export signal (NES), the unbound fusion protein will distribute between the nucleus and the cytoplasm in a ratio based upon the relative strengths of the first and the second localization domains. Upon binding of the molecule of interest to the binding domain, the NLS will be inhibited, NES targeting will then predominate over NLS targeting, and the fusion protein will be primarily localized in the cytoplasm.

As used herein, "subcellular compartment" refers to any sub-structural macromolecular component of the cell whether it is made of protein, lipid, carbohydrate, or nucleic acid. It could be a macromolecular assembly or an organelle (a membrane delimited cellular component). Subcellular compartments include, but are not limited to, cytoplasm, nucleus, nucleolus, inner and outer surface of the nuclear envelope, regions within the nucleus with localized activities, such as transcription, cytoskeleton, inner leaflet of the plasma membrane, outer leaflet of the plasma membrane, outer leaflet of the mitochondrial membrane, inner leaflet of the mitochondrial membrane, inner or outer leaflet of the inner mitochondrial membrane, Golgi, endoplasmic reticulum, and extracellular space.

In a preferred embodiment, the first localization domain is selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NOS:145–287, and SEQ ID NOS:315–325 (See FIGS. 2, 4, 5, 6, and 10). In a further preferred embodiment, either the first or the second localization domain is a nuclear localization signal, while the other localization domain is a nuclear export signal, resulting in a fusion protein that is distributed between the nucleus and the cytoplasm. Selection of the most appropriate localization domains can be accomplished by one of skill in the art using the teachings herein.

It is possible to maximize the signal-to-noise ratio from the fusion protein by using localization domains that bias distribution of the fusion protein to the subcellular compartment where the binding event is most likely to occur (i.e. where the molecule of interest is most likely to be present). For example, deacetylases, such as histone deacetylases, are often found in the nucleus, where they are involved in chromatin reorganization. Using a fusion protein with a binding domain for a histone deacetylase, a strong NLS as the first localization sequence, such as the SV40 NLS (SEQ ID NO:145), with a relatively weak NES as the second localization sequence, such as the MAPKAP-2 NES (SEQ ID NO:317), will result in an equilibrium bias distribution of the unbound fusion protein favoring nuclear distribution. Optically detectable signals from the fusion protein in the cytoplasm will be relatively low in intensity. Upon binding of the deacetylase to the fusion protein binding domain proximal to the NLS, nuclear import will be blocked, resulting in accumulation of the fusion protein in the cytoplasm. Since the cytoplasm starts out with a relatively low intensity of detectable signal, relatively small increases in intensity are more readily detected than if the intensity of the unbound fusion protein in the cytoplasm were higher.

In another example, for a protein generally limited to the cytoplasm, such as ras, a fusion protein composed of a binding domain for ras (example, from c-raf), a relatively strong NES, such as from MEK 1 (SEQ ID NO:17) as a first localization sequence, and a weaker NLS, such as from NFkB (SEQ ID NO:5) as a second localization sequence results in an equilibrium bias distribution of the unbound fusion protein favoring the cytoplasm. Optically detectable signals from the fusion protein in the nucleus will be relatively low in intensity. Upon ras binding to the fusion protein in the cytoplasm, nuclear export is blocked, and the nuclear intensity of the optically detectable signals from the fusion protein will increase. Since the nucleus starts out with a relatively low intensity of detectable signal, relatively small increases in intensity are more readily detected than if the intensity of the unbound fusion protein in the nucleus were higher. When the compartment where the binding event of the molecule of interest is unknown, or when the molecule of interest is relatively evenly distributed between compartments, using an NES and NLS combination where the equilibrium bias is a fairly equal distribution between the two subcellular compartments avoids the need for any prior knowledge of the compartmentalization of the target protein. One of skill in the art will readily be able to optimize the design of the localization domains using the teachings herein.

As used herein, "binding domain" refers to one or more amino acid sequences to which the molecule of interest binds. The binding domain may be a naturally occurring binding domain, a mutant, variant, or fragment thereof, or an artificial domain. It is to be understood that the binding domain can comprise a binding site for any molecule of interest. Thus, the fusion protein of the present invention can detect binding of any type of molecule that binds to a binding domain comprising an amino acid sequence. In a preferred embodiment, the binding domain is a binding domain for a molecule of interest selected from the group consisting of nucleic acid, protein, and lipid. In a most preferred embodiment, the binding domain is a binding domain for a protein of interest. (For examples, see FIG. 3.)

In one embodiment, such proteins are those involved in post-translational modifications, including, but not limited to, protein kinases, protein phosphatases, and proteins promoting protein glycosylation, acetylation, and ubiquitination, fatty acid acylation, and ADP-ribosylation.

The binding domain can comprise (a): an amino acid sequence for non-covalent binding (such as protein-protein interaction sites), referred to as a "non-covalent binding site"; (b) an amino acid sequence for covalent binding, defined as the amino acid or amino acid sequence at which the molecule of interest effects an enzymatic reaction (ie: covalent binding), and referred to as a "covalent binding site"; or (c) a combination of one or more covalent binding sites and one or more non-covalent binding sites. An example of a covalent binding site is an amino acid(s) that is/are phosphorylated by a kinase.

In a most preferred embodiment, the binding domain does not contain a "cleavage site", wherein "cleavage site" is defined as an amino acid sequence within the binding domain that is targeted for cleavage by a proteolytic enzyme. Since the recombinant fusion proteins of the invention are used to detect binding of the molecule of interest to the binding domain, and since such detection relies on steric hindrance of the first localization domain by the bound molecule of interest, it is highly preferred that the recombinant fusion proteins remain intact, and that binding of the molecule of interest does not result in cleavage of the fusion protein. Furthermore, the recombinant fusion proteins of the present invention are capable of permitting reversible detection of binding. The non-covalent binding is generally reversible due to equilibrium considerations, while the covalent binding can be reversible by action of enzymes that reverse a given post-translational modification, such as phosphatases, deacetylases, etc. The presence of a cleavage site within the binding domain would eliminate such reversible measurements.

In one embodiment, the binding domain consists of a binding domain for a nucleic acid of interest. In a more preferred embodiment, the nucleic acid of interest is an RNA of interest. In a further preferred embodiment, the binding domain for the RNA of interest has an amino acid sequence selected from the group consisting of SEQ ID NOS:310–314 (see FIG. 9). In a further preferred embodiment, the nucleic acid of interest is a DNA. In a preferred embodiment, the binding domain for the DNA of interest has an amino acid sequence selected from the group consisting of SEQ ID NO:338 and SEQ ID NO:339.

In a further embodiment, the binding domain consists of a binding domain for a lipid of interest. For example, the pleckstrin homology (PH) (SEQ ID NO:364, encoded by SEQ ID NO:363) domain from phospholipases that binds PIP2 phospholipids (Wang et al., 2000, J. Biol. Chem. 275:7466–7469; Singer et al., 1997, Annu. Rev Biochem 66:475–509), or the diacylglycerol binding domain (DBD) from protein kinase C (SEQ ID NO:366, encoded by SEQ ID NO:365), can be used to detect generation of PIP2 phospholipids or diacyglycerol, respectively, at the plasma membrane. Insertion into the fusion protein of the PH domain or DBD as the binding domain wherein the first localization sequence comprises an NLS would lead to blockage of nuclear import of the fusion protein upon the generation of PIP2 phospholipids at the plasma membrane. The bound fusion protein would not translocate from the cytoplasm to the nucleus, but would accumulate at the plasma membrane. Thus, analysis could entail measurements at the cytoplasm, nucleus, and plasma membrane.

In a further preferred embodiment, the binding domain is not a binding domain for a protease, and the molecule of interest is not a protease.

In embodiments wherein the binding domain consists of a non-covalent binding site but does not include a covalent binding site, the fusion protein serves to detect binding events only, without detection of subsequent enzymatic reactions. Thus, for example, the fusion protein can be used to detect expression and appropriate secondary and tertiary structure of a protein kinase, but is not biased by other post-translational modifications that counteract the enzymatic activity of the protein kinase (for example, protein phosphatase activity). In one such embodiment, the binding domain is a binding domain for a protein, and has an amino acid sequence selected from the group consisting of SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, and SEQ ID NO:115, SEQ ID NO:117, SEQ ID NO:119, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:141, SEQ ID NO:143, SEQ ID NO:341, SEQ ID NO:343, SEQ ID NO:345, SEQ ID NO:347, SEQ ID NO:349, SEQ ID NO:350, SEQ ID NO:352, SEQ ID NO:354, SEQ ID NO:356, SEQ ID NO:358, SEQ ID NO:360, SEQ ID NO:362, SEQ ID NO:364, and SEQ ID NO:366 (see FIGS. 3 and 11).

In a further embodiment wherein the binding domain consists of a non-covalent binding site but does not include a covalent binding site, the binding domain is a binding domain for a protein kinase. In a further embodiment, the binding domain for the protein kinase has an amino acid sequence selected from the group consisting of SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:120, SEQ ID NO:122, SEQ ID NO:124, SEQ ID NO:126, SEQ ID NO:128, SEQ ID NO:341, SEQ ID NO:343, SEQ ID NO:345, SEQ ID NO:347, SEQ ID NO:349, SEQ ID NO:350, SEQ ID NO:352.

In a further embodiment wherein the binding domain consists of a non-covalent binding site but does not include a covalent binding site, the binding domain is a binding domain for an acetyl transferase. In a preferred embodiment, the binding domain for a histone acetyl transferase has an amino acid sequence selected from the group consisting of SEQ ID NO:132, SEQ ID NO:134, SEQ ID NO:136, SEQ ID NO:354, and SEQ ID NO:356.

In a further preferred embodiment wherein the binding domain consists of a non-covalent binding site but does not include a covalent binding site, the binding domain is a binding domain for a histone deacetylase. In a preferred embodiment, the binding domain for the histone deacetylase has an amino acid sequence of SEQ ID NO:138.

In a further preferred embodiment wherein the binding domain consists of a non-covalent binding site but does not include a covalent binding site, the binding domain is a binding domain for an ubiquitin ligase. In a further preferred embodiment, the binding domain for the ubiquitin ligase has an amino acid sequence selected from the group consisting of SEQ ID NO:140 and SEQ ID NO:141.

In embodiments wherein the binding domain is a non-covalent binding site but does not include a covalent binding site, the binding domain for the molecule of interest is separated from the first localization domain by 0–20 amino acid residues, and the binding domain for the molecule of interest is separated from the second localization domain (if present) by more than 20 amino acid residues. In preferred embodiments, the binding domain for the molecule of interest is separated from the first localization domain by 0–15 amino acids, and more preferably by 0–10 amino acids. This spacing dictates that the molecule of interest can act to sterically hinder the effect of the first localization domain, while minimizing any potential steric hindrance on the second localization domain. Thus, for example, the binding domain can partially or completely overlap with the first localization domain. The same is true for embodiments of the binding domain with only the covalent binding site, which can also overlap with the first localization domain, or with both the covalent binding site and the non-covalent binding site.

Thus, according to these various embodiments wherein the binding domain comprises a non-covalent binding site, but does not include a covalent binding site, the non-covalent binding site is preferably separated from the first localization domain by 0, 1, 2, 3, 4, 5, 6, 7, 8, 9, 10, 11, 12, 13, 14, 15, 16, 17, 18, 19, or 20 amino acid-residues.

In embodiments wherein the binding domain is a covalent binding site but does not include a non-covalent binding site, the covalent binding site is preferably separated from the first localization domain by 0, 1, 2, 3, 4, 5, or 6 amino acid residues. In a preferred embodiment, the binding domain is preferably separated from the first localization domain by 0–4, and more preferably by 0–2 amino acid residues. Preferred embodiments of such binding domains include amino acid sequences selected from the group consisting of SEQ ID NOS:341, 343, 345, 347, 349, 350, 352 (all of which are binding domains for kinases), 354, 356 (both of which are binding domains for acetylases), 358, 360, and 362 (all of which are binding domains for farnesylases).

In these embodiments, the covalent binding resulting from the enzymatic reaction, including but not limited to phosphorylation, acetylation, ubiquitination, or farnesylation, inhibits activity of the first localization domain via steric hindrance, leading to a change in the distribution of the fusion protein, as described above. In these embodiment, the change in distribution of the recombinant fusion protein provides direct evidence for post-translational modification of the binding domain by the molecule of interest, and thus provides a different functionality from the embodiment wherein the binding domain does not include the covalent binding site. In these embodiments, wherein the fusion protein further comprises a second localization domain, the covalent binding site is preferably separated from the second localization domain by more than 6 amino acid residues; preferably by at least 10 amino acid residues, and more preferably by at least 20 amino acid residues.

In embodiments wherein the binding domain is both a covalent binding site and a non-covalent binding site, either or both of the above spacing requirements are satisfactory. Thus, the covalent binding site in the binding domain is preferably separated from the first localization domain by 0, 1, 2, 3, 4, 5, or 6 amino acid residues. In a preferred embodiment, the binding domain is preferably separated from the first localization domain by 0–4, and more preferably by 0–2 amino acid residues. Alternatively, or in addition, the non-covalent binding site for the molecule of interest is separated from the first localization domain by 0–20 amino acid residues, preferably 0–15 amino acid residues, and more preferably by 0–10 amino acid residues. It is to be understood that in this embodiment, the covalent binding site and the non-covalent binding site do not have to be contiguous, although they may be contiguous. Thus, there may be amino acid residues present between the covalent binding site and the non-covalent binding site. The length of such intervening sequences is variable, and may be determined readily by one of skill in the art. This embodiment provides added functionality to the fusion proteins of the invention, as the presence of the non-covalent binding site adds specificity to the enzymatic reaction occurring at the covalent binding site. For example, a covalent binding site for a kinase may be common to multiple kinases. Thus, including a non-covalent binding site for a specific kinase increases specificity and efficiency of the enzyme at the covalent binding site.

In all of these embodiments, it is most preferred that the binding domain does not include a cleavage site, that the binding domain is not a binding domain for a protease, and that the molecule of interest is not a protease.

As used herein, "detection domain" means one or more amino acid sequence that can be detected. This includes, but is not limited to, inherently fluorescent proteins (e.g. Green Fluorescent Proteins and fluorescent proteins from nonbioluminescent Anthozoa species), cofactor-requiring fluorescent or luminescent proteins (e.g. phycobiliproteins or luciferases), and epitopes recognizable by specific antibodies or other specific natural or unnatural binding probes, including, but not limited to, dyes, enzyme cofactors and engineered binding molecules, which are fluorescently or luminescently labeled. Such detection domains include, but are not limited to, amino acid sequences selected from the group consisting of SEQ ID NOS:288–295 (see FIG. 7). Also included are site-specifically labeled proteins that contain a luminescent dye. Methodology for site-specific labeling of proteins includes, but is not limited to, engineered dye-reactive amino acids (Post, et al., *J. Biol. Chem.* 269:12880–12887 (1994)), enzyme-based incorporation of luminescent substrates into proteins (Buckler, et al., *Analyt. Biochem.* 209:20–31 (1993); Takashi, *Biochemistry.* 27:938–943 (1988)), and the incorporation of unnatural labeled amino acids into proteins (Noren, et al., *Science.* 244:182–188 (1989)).

As used herein, the term "operably linked" refers to an arrangement of elements wherein the components so described are configured so that they function as a unit for their intended purpose.

As used herein, "target" or "targeted" means to direct the fusion protein to a particular subcellular compartment.

In a preferred embodiment, the fusion protein further comprises a transport peptide domain for delivery into the cell. As used herein, "transport peptide domain" means one or more amino acid sequences that drive transport of the fusion protein into a cell. Examples of such transport peptide domains include, but are not limited to SEQ ID NOS: 291–304 (see FIG. 8).

In another aspect, the present invention provides a recombinant nucleic acid molecule encoding a recombinant fusion protein for detecting binding of a molecule of interest, as described above. In a preferred embodiment, the recombinant nucleic acid molecule comprises the following operably linked regions in frame relative to each other:
  a) a first nucleic acid sequence encoding a detection domain;
  b) a second nucleic acid sequence encoding a first localization domain; and
  c) a third nucleic acid sequence encoding a binding domain for the molecule of interest;
wherein the third nucleic acid sequence is separated from the second nucleic acid sequence by 0–60 nucleotides, and wherein the second nucleic acid sequence and the third nucleic acid sequence do not all occur in a single non-recombinant nucleic acid molecule, or do not all occur in a single non-recombinant nucleic acid molecule with the same spacing as in the recombinant nucleic acid molecule encoding a recombinant fusion protein for detecting binding of a molecule of interest.

In a preferred embodiment the third nucleic acid sequence is separated from the second nucleic acid sequence by 0–45 nucleotides, and more preferably by 0–30 nucleotides. Thus, in these various preferred embodiments, the third nucleic acid sequence is separated from the second nucleic acid sequence by 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In a preferred embodiment, the recombinant nucleic acid molecule further comprises a fourth nucleic acid sequence encoding a second localization domain, wherein the fourth nucleic acid sequence is operably linked to the first, second, and third nucleic acid sequences, wherein the fourth nucleic acid sequence is separated from the third nucleic acid sequence by more than 60 nucleotides; wherein the first localization domain and the second localization domain do not target the recombinant fusion protein to an identical subcellular compartment; and wherein the second nucleic acid sequence, the third nucleic acid sequence, and the fourth nucleic acid sequence do not all occur in a single non-recombinant nucleic acid molecule, or do not all occur in a single non-recombinant nucleic acid molecule with the same spacing as in the recombinant nucleic acid molecule encoding a recombinant fusion protein for detecting binding of a molecule of interest.

In embodiments wherein the third nucleic acid sequence encodes a binding domain that is a non-covalent binding site but does not include a covalent binding site, the third nucleic acid sequence is separated from the second nucleic acid sequence encoding the first localization domain by 0–60 nucleotides, preferably 0–45 nucleotides, and more preferably 0–30 nucleotides, and the third nucleic acid sequence is separated from the fourth nucleic acid sequence encoding the second localization domain (if present) by more than 60 nucleotides.

In embodiments wherein the third nucleic acid sequence encodes a binding domain comprising a covalent binding site but no non-covalent binding site, the nucleic acid sequence encoding the covalent binding site is preferably separated from the nucleic acid sequence encoding the first localization domain by 0–18 nucleotides, more preferably by 0–12 nucleotides, and even more preferably by 0–6 nucleotides. Preferred embodiments of such nucleic acid sequences encode an amino acid sequence selected from the group consisting of SEQ ID NOS:341, 343, 345, 347, 349, 350, 352, 354, 356, 358, 360, and 362. In a further preferred embodiment, the third nucleic acid sequence is selected from the group consisting of SEQ ID NOS:340, 342, 344, 346, 348, 351, 353, 355, 357, 359, and 361. In these embodiments, wherein the recombinant nucleic acid molecule further comprises a fourth nucleic acid sequence encoding a second localization domain, the third nucleic acid sequence is preferably separated from the fourth nucleic acid sequence by more than 18 nucleotides, preferably by at least 30 nucleotides, and more preferably by at least 60 nucleotides.

In embodiments wherein the third nucleic acid encodes a binding domain with a covalent binding site and a non-covalent binding site, either or both of the above spacing requirements are satisfactory. Thus, the nucleic acid sequence encoding the covalent binding site in the binding domain is preferably separated from the second nucleic acid sequence encoding the first localization domain by 0–18, preferably 0–12, and more preferably 0–6 nucleotides. Alternatively, or in addition, the nucleic acid sequence encoding the non-covalent binding site for the molecule of interest is separated from the second nucleic acid sequence encoding the first localization domain by 0–60 nucleotides, preferably 0–45 nucleotides, and more preferably by 0–30 nucleotides. It is to be understood that in this embodiment, the nucleic acid sequences encoding the covalent binding site and the non-covalent binding site do not have to be contiguous within the third nucleic acid sequence.

In all of these embodiments, it is most preferred that the third nucleic acid sequence does not encode a binding domain with a cleavage site, and that the molecule of interest is not a protease.

A nucleic acid sequence is operably linked to another nucleic acid coding sequence when the coding regions of both nucleic acid sequences are capable of expression in the same reading frame. The nucleic acid sequences need not be contiguous, so long as they are capable of expression in the same reading frame. Thus, for example, intervening coding regions can be present between the specified nucleic acid coding sequences, and the specified nucleic acid coding regions can still be considered "operably linked"

The nucleic acid molecule of the invention can comprise DNA or RNA, and can be single stranded or double stranded.

In a preferred embodiment, the third nucleic acid sequence encodes a binding domain for a molecule of interest selected from the group consisting of nucleic acid, protein, and lipid.

Thus, the third nucleic acid sequence may encode an amino acid sequence comprising a sequence selected from the group consisting of SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, and SEQ ID NO:115, SEQ ID NO:117, SEQ ID NO:119, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:141, SEQ ID NO:143, SEQ ID NO:341, SEQ ID NO:343, SEQ ID NO:345, SEQ ID NO:347, SEQ ID NO:349, SEQ ID NO:350, SEQ ID NO:352, SEQ ID NO:354, SEQ ID NO:356, SEQ ID NO:358, SEQ ID NO:360, SEQ ID NO:362, SEQ ID NO:364, and SEQ ID NO:366.

In a further preferred embodiment, the third nucleic acid sequence encodes a binding domain for a protein kinase with an amino acid sequence selected from the group consisting of SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:120, SEQ ID NO:122, SEQ ID NO:124, SEQ ID NO:126, SEQ ID NO:128, SEQ ID NO:341, SEQ ID NO:343, SEQ ID NO:345, SEQ ID NO:347, SEQ ID NO:349, SEQ ID NO:350, SEQ ID NO:352.

In a further preferred embodiment, the third nucleic acid sequence is selected from the group consisting of SEQ ID NO:26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 121, 123, 125, 127, 129, 131, 133, 135, 137, 139, 142, 144, 340, 342, 344, 346, 348, 351, 353, 355, 357, 359, and 361.

In another embodiment, the third nucleic acid sequence encodes a binding domain for an acetyl transferase. In this embodiment, it is preferred that the third nucleic acid sequence encodes an amino acid sequence selected from the group consisting of SEQ ID NO:132, SEQ ID NO:134, SEQ ID NO:136, SEQ ID NO:354, and SEQ ID NO:356.

In another embodiment, the third nucleic acid sequence encodes a binding domain for a histone deacetylase. In this embodiment, it is preferred that the third nucleic acid sequence encodes an amino acid sequence selected from the group consisting of SEQ ID NO:138.

In another embodiment, the third nucleic acid sequence encodes a binding domain for an ubiquitin ligase. In this embodiment, it is preferred that the third nucleic acid sequence encodes an amino acid sequence selected from the group consisting of SEQ ID NO:140 and SEQ ID NO:141.

In another embodiment, the third nucleic acid sequence encodes a binding domain for a nucleic acid of interest. In a preferred embodiment, the nucleic acid of interest is an RNA of interest. In this embodiment, it is preferred that the third nucleic acid sequence encodes an amino acid sequence selected from the group consisting of SEQ ID NOS:310–314.

In any of these embodiments, the second nucleic acid sequence preferably encodes a first localization domain selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NOS:145–287, and SEQ ID NOS:315–325. Selection of nucleic acid sequences encoding the most appropriate localization domains to be used in conjunction with a given nucleic acid sequence encoding a binding domain can be readily accomplished by one of skill in the art using the teachings herein.

In a further preferred embodiment, the second and fourth nucleic acid sequences encode amino acid sequences selected from the group consisting of SEQ ID NO:1, 3, 5, 7, 9, 11, 13, 15, 17, 19, 21, 23, and 145–287.

In each of these embodiments, the first nucleic acid sequence encodes a detection domain as described above. In any of the above embodiments, the recombinant nucleic acid molecule can also further comprise nucleic acid sequence that encodes a transport peptide domain, as described above.

In another aspect, the present invention provides a recombinant nucleic acid molecule comprising the following operably linked regions in frame relative to each other:

a) a first nucleic acid sequence encoding a detection domain;

b) a second nucleic acid sequence encoding a first localization domain; and c) a third nucleic acid sequence that comprises one or more restriction enzyme recognition sites that are not present elsewhere in the recombinant nucleic acid molecule;

wherein the third nucleic acid sequence is separated from the second nucleic acid sequence by 0–60 nucleotides; and wherein the second nucleic acid sequence and the third nucleic acid sequence do not both occur in a single non-recombinant nucleic acid molecule, or do not both occur in a single non-recombinant nucleic acid molecule with the same spacing as in the recombinant nucleic acid molecule.

In various preferred embodiments, the third nucleic acid sequence is separated from the second nucleic acid sequence by 0–45 and 0–30 nucleotides. Thus, in these various preferred embodiments, the restriction enzyme recognition site in the third nucleic acid sequence that is closest to the second nucleic acid sequence is separated from the second nucleic acid sequence by 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In a preferred embodiment, the recombinant nucleic acid molecule further comprises a fourth nucleic acid sequence encoding a second localization domain that is operably linked to the first, second, and third nucleic acid sequences, wherein the fourth nucleic acid sequence is separated from the third nucleic acid sequence by more than 60 nucleotides; wherein the first and second localization domains do not target the recombinant fusion protein to an identical subcellular compartment; and wherein the second nucleic acid sequence, the third nucleic acid sequence, and the fourth nucleic acid sequence do not all occur in a single non-recombinant nucleic acid molecule, or do not all occur in a single non-recombinant nucleic acid molecule with the same spacing as in the recombinant nucleic acid molecule.

In this aspect of the invention, the preferred embodiments for the first, second, and fourth nucleic acid sequences are as described above.

This aspect of the invention permits the custom design of a fusion protein for detecting binding of any molecule of interest, and the above embodiments are particularly appropriate for designing fusion proteins wherein the binding domain consists of a non-covalent binding site, or both a covalent binding site and a non-covalent binding site.

In a further embodiment, the recombinant nucleic acid molecule of this aspect of the invention is as described above, with the exception that the third nucleic acid sequence is separated from the second nucleic acid sequence by 0–18 nucleotides, and wherein the third nucleic acid sequence is separated from the fourth nucleic acid sequence (if present) by more than 18 nucleotides. This embodiment is particularly appropriate for designing fusion proteins wherein the binding domain consists of a covalent binding site, or both a covalent binding site and a non-covalent binding site.

The third nucleic acid sequence may consist of a single restriction enzyme site, may comprise multiple restriction enzyme sites (i.e.: a "polynucleotide linker") or variations thereof. The third nucleic acid may comprise more than one copy of a given restriction enzyme recognition site, as long as the restriction enzyme recognition site is not present elsewhere in the recombinant nucleic acid molecule.

As used herein, the phrase "one or more restriction enzyme recognition sites that are not present elsewhere in the recombinant nucleic acid molecule" refers to the presence of restriction enzyme recognition sites within the third nucleic acid sequence that can be cleaved by restriction enzymes using standard techniques, to provide a suitable ligation site for one of skill in the art to use for cloning of a binding domain of a molecule of interest within a given distance from the second nucleic acid sequence encoding the first localization domain. As used herein, the limitation that the "third nucleic acid sequence is separated from the second nucleic acid sequence by 0–60 nucleotides" means that the restriction enzyme recognition site in the third nucleic acid sequence closest to the second nucleic acid sequence and not present elsewhere in the recombinant nucleic acid molecule must be within 0–60 nucleotides of the second nucleic acid sequence. Thus, other restriction enzyme recognition sites in the third nucleic acid sequence and not present elsewhere in the recombinant nucleic acid molecule may be more than 60 nucleotides from the second nucleic acid sequence. For example, if the third nucleic acid sequence comprises a polynucleotide linker containing 7 restriction enzyme recognition sites that are not present elsewhere in the recombinant nucleic acid molecule, only the restriction enzyme recognition site in the polynucleotide linker that is closest to the second nucleic acid sequence is required to be 60 nucleotides or fewer from the second nucleic acid sequence. Alternatively, all, or more than one, of the restriction enzyme recognition sites may be within 60 nucleotides of the second nucleic acid sequence.

In this embodiment, the location of the restriction enzyme recognition sites in the third nucleic acid sequence that are not present elsewhere in the recombinant nucleic acid molecule permit the cloning of a sequence encoding a binding domain of the molecule of interest within 60 nucleotides or less of the second nucleic acid sequence encoding the first localization domain into the recombinant nucleic acid molecule. This can be accomplished by cloning directly into a single restriction enzyme recognition site that is within 60 nucleotides of the second nucleic acid, or may, by way of a non-limiting example, involve restriction enzyme digestion at two or more of the restriction sites in the third nucleic acid sequence and removal of a portion of the third nucleic acid sequence in order to clone in a nucleic acid encoding a binding domain to be within 60 nucleotides of the second nucleic acid sequence. Such cloning strategies and implementation are well known in the art.

In another aspect the invention provides recombinant expression vectors comprising DNA control sequences operably linked to the recombinant nucleic acid molecules of the present invention, as disclosed above. "Control sequences" operably linked to the nucleic acid sequences of the invention are nucleic acid sequences capable of effecting the expression of the recombinant nucleic acid molecules. The control sequences need not be contiguous with the individual nucleic acid sequences, as long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, and termination signals.

In another aspect the invention provides genetically engineered host cells that have been transfected with the recombinant expression vectors of the invention. Such host cells can be prokaryotic, for example, to produce large quantities of the recombinant nucleic acid molecules or proteins of the invention. Alternatively, such host cells can be eukaryotic cells, particularly for use in the methods of the invention described below.

In another aspect the invention provides kits containing the fusion proteins, the nucleic acid molecules, the expression vectors or the host cells of the invention and instructions for their use in the detection of binding of a molecule of interest to the fusion protein in a cell.

In another aspect, the invention provides methods for detecting binding of a molecule of interest to a fusion protein in a cell, comprising providing host cells that contain one or more of the fusion proteins of the invention, obtaining optically detectable signals from the detection domain of the fusion protein, and determining the subcellular distribution of the optically detectable signals, wherein the subcellular distribution of the optically detectable signals correlates with the subcellular distribution of the fusion protein. Changes in the subcellular distribution of the fusion protein indicate a change in the binding of the molecule of interest to the binding domain in the fusion protein, or may indicate direct binding of a test compound of interest to the binding domain. For example, the binding of a test compound to the recombinant fusion protein of the invention can be used to identify those compounds that mimic binding of the molecule of interest to the binding domain. Preferably, such an assay would be conducted using cells that do not express the molecule of interest, including but not limited to knock out cell lines and cells that have otherwise been manipulated to not express the molecule of interest.

As discussed above, the unbound fusion protein is distributed based on the subcellular distribution directed by the first localization domain (in the embodiment with only one localization domain), or based on the subcellular distribution between two subcellular compartments as directed by the first and the second localization domains, in a ratio based upon the relative strengths of the first and the second localization domains. Thus, in the two localization domain embodiment, in the unbound state, there may be an equilibrium in the distribution of the fusion protein between the two targeted domains, or either one or the other localization domain may bias the distribution of the fusion protein.

Upon binding of the molecule of interest (or, possibly, a test compound) to the binding domain of the fusion protein, the ability of the first localization domain to direct the fusion protein to the subcellular compartment normally targeted by the first localization domain is inhibited, due to steric hindrance caused by the proximity of the bound molecule of interest. Thus, the distribution of the fusion protein in the cell will be without bias in the embodiment with only the first localization domain, or will be determined mainly by the second localization domain in the embodiment with both a first and second localization domain, causing a change in the distribution of the bound fusion protein within a cell, which can be detected by a change in the distribution of detectable signal from the detection domain of the fusion protein within the cell.

In a further preferred embodiment, the method further comprises contacting the host cells with one or more test compounds, comparing the subcellular distribution of the fusion protein in the presence and absence of one or more test compounds, and identifying those compounds that alter the subcellular distribution of the fusion protein, wherein such altering of the subcellular distribution of the fusion protein indicates that one or more of the test compounds have altered the binding of the molecule of interest to the fusion protein in the cells, either directly or indirectly, or that the test compound itself has bound to the binding domain of the fusion protein. The one or more test compounds can be of any nature, including, but not limited to, chemical and biological compounds, environmental samples, and cultured cell media. The one or more test compounds may also comprise a plurality of compounds, including, but not limited to, combinatorial chemical libraries and natural compound libraries. Contacting of the cells with the one or more test compounds can occur before, after, and/or simultaneously with obtaining optically detectable signals from the detection domain, depending on the assay design. For example, in order to carry out kinetic screening, it is necessary to obtain optically detectable signals from the detection domain at multiple time points, and the user may obtain such signals before, at the time of, and after contacting of the cells with the test compound.

In a preferred embodiment, the binding domain comprises a binding domain for a molecule of interest selected from the group consisting of nucleic acid, protein, and lipid. In a most preferred embodiment, the binding domain comprises a binding domain for a protein of interest.

The fusion protein may be expressed by transfected cells or added to the cells via non-mechanical modes including, but not limited to, diffusion, facilitated or active transport, signal-sequence-mediated transport, and endocytotic or pinocytotic uptake; or combinations thereof, at any time during the screening assay. Mechanical bulk loading methods, which are well known in the art, can also be used to the fusion proteins into living cells (Barber et al. (1996), *Neuroscience Letters* 207:17–20; Bright et al. (1996), *Cytometry* 24:226–233; McNeil (1989) in *Methods in Cell Biology*, Vol. 29, Taylor and Wang (eds.), pp. 153–173). These methods include, but are not limited to, electroporation and other mechanical methods such as scrape-loading, bead-loading, impact-loading, syringe-loading, hypertonic and hypotonic loading.

Optically detectable signals from the detection domain may be obtained by any method able to resolve the distribution of the detectable signals in cells. Such detection involves recording one or more of the presence, position, and amount of the signal, and is accomplished via any means for so recording the presence, position, and/or amount of the signal. The approach may be direct, if the signal is inherently fluorescent, or indirect, if, for example, the signal is an epitope that must be subsequently detected with a labeled antibody. Modes of detection include, but are not limited to: (1) intensity; (2) polarization; (3) lifetime; (4) wavelength; (5) energy transfer; and (6) recovery after photobleaching.

In a preferred embodiment, obtaining optically detectable signals from the detection domain comprises obtaining images of fluorescent signals at subcellular resolution, wherein the cellular localization of the fluorescent signals is determined. Such "high content" images comprise a digital representation of the fluorescent signals from the detection domain, and do not require a specific arrangement or display of the digital representation. In preferred embodiments, well known formats for such "images" are employed, including, but not limited to, .dib, tiff, jpg, and .bmp. In further preferred embodiments, the images are analyzed algorithmically, and/or displayed to provide a visual representation of the image.

In another preferred embodiment, changes in the distribution of the fusion protein between the cytoplasm and nucleus are detected. Such changes include, but are not limited to, increase or decrease of signal, changes in the difference of signal in the two compartments, changes in the ratio of signal between the two compartments, and changes in the ratio of signal relative to the same cell at different time points. In a preferred embodiment, the cells also possess a nuclear stain, such as Hoechst 33342, to identify the nuclei of individual cells. A nuclear image is acquired and preferably thresholded to create a nuclear mask. A cytoplasmic image is created using either the nuclear image (for example, by dilation), or the fluorescent signals from the detection domain of the fusion protein. Redistribution of the fluorescent signal between the nucleus and the cytoplasm can then be determined by detecting fluorescent signals from the detection domain in the nuclear mask and cytoplasmic mask in the presence and absence of one or more test compounds. One of skill in the art will understand that various such assays can be employed to measure the distribution of the fusion protein in the cell, depending on the subcellular domains targeted by the first and the second localization domains. Such other assays are disclosed, for example, in WO 98/38490, WO 00/03246, and WO00/70342.

In a preferred embodiment, the optically detectable signals are obtained on a high content screening (HCS) system. As used herein, "high content screening system" means a device capable of automatically acquiring and analyzing optically detectable signals at a subcellular level, such as that disclosed in U.S. Pat. No. 5,989,835.

Benefits of the fusion proteins and associated methods of the present invention include, but are not limited to: 1) the ability to concentrate the signal in order to achieve a high signal to noise ratio (the target compartment, such as the nucleolus, may be very small in order to concentrate the signal into a very small area); 2) the ability to assay either living or fixed cells without changing the assay format; 3) the need for only a single fluorescent signal, thus limiting the range of spectrum required for measuring one activity, particularly for multiparameter assays; 4) the arrangement of the domains of the fusion protein is flexible and applicable to the development of fusion proteins for many different assays; 5) the ability, with the use of different localization domains, to monitor multiple binding events using the same detection signal wavelength, wherein the color would be the same but the spatial position of the different fusion proteins would provide discrimination; and 6) the ability to alter the sensitivity of the assay by adjusting the relative strengths of the first localization domain and the second localization domain.

The present invention may be better understood in light of the following examples.

EXAMPLES

The following abbreviations may be found throughout this section:

| | |
|---|---|
| CREB | cAMP-Response Element Binding Protein |
| GFP | Green Fluorescent Protein |
| JNK/SAPK | c-Jun N-terminal Kinase/Stress Activated Protein Kinase |
| MAPK | Mitogen Activated Protein Kinase |
| MAPKAP2/MK2 | Mitogen Activated Protein Kinase-Activated Protein Kinase 2 |
| MEK1/2 | MAP Kinase Kinase 1/2 |
| NES | Nuclear Export Signal |
| NLS | Nuclear Localization Signal |
| PKA | cAMP-dependent Protein Kinase |
| PKI | Protein Kinase A Inhibitor |
| PMA | Phorbol-12-Myristate-13-Acetate |
| RSK1/2 | Ribosomal S Kinase 1/2 |
| SV40 | Simian Virus 40 |

Example 1 cAMP-Dependent Protein Kinase Interaction Fusion Protein

Introduction

In this example, a fusion protein for detecting the availability for specific binding of the catalytic domain of cAMP-dependent protein kinase (cPKA), the protein of interest, is based on the distribution of the fusion protein between the cytoplasm and nucleus. It is constructed such that the detection domain is a GFP, the first localization domain is the NLS from SV40 large T-antigen, the second localization domain is the NES from MAPKAP2, and the binding domain is from CREB. The NLS and the binding domain are separated by 2 amino acids. The fusion protein is introduced into cells via DNA transfection or retrovirus infection. The catalytic domain cPKA binds to the regulatory domain of PKA (rPKA) in the absence of cAMP. With an increase in the concentration of cAMP, cPKA dissociates from rPKA, enabling cPKA to bind to the fusion protein. Operationally, the binding of cPKA to the binding domain blocks the localization of this fusion protein into the nucleus. Thus, the GFP fluorescence intensity of the nucleus will decrease upon binding cPKA with a comparable increase in the cytoplasmic GFP fluorescence. The ratio of these intensities can be readily measured. This fusion protein can detect cPKA binding in either the nucleus or cytoplasm. Contacting the cell with a compound that causes a separation of cPKA from rPKA, such as forskolin, via an increase cAMP, will shift the distribution of the fusion protein from the nucleus to the cytoplasm.

In an alternative to genetic introduction, the fusion protein may be introduced into the cells by external delivery. The fusion protein is produced using, for example, a baculovirus-insect cell system. The fusion protein can be labeled with a sulfhydryl-specific reactive fluorescent dye, such as Alexa 568-maleimide, to provide the detectable signal of the detection domain. In this situation, the fusion protein contains a protein transport peptide sequence that facilitates the incorporation of the fusion protein into living cells. The purified labeled fusion protein is then delivered into cells by mixing with cells. After incubation and washing, the fusion protein will reach an equilibrium distribution within the cells.

Construction of Fusion Protein

As shown below, this fusion protein was constructed using a GFP, a nuclear localization signal from the SV 40 large T antigen (SEQ ID NO:145), the sequence from Proline 315 to Serine 362 of MAPKAP2 (Genbank accession number X76850), which includes a nuclear export signal (between $D^{328}$ to $E^{351}$), and the sequence from $I^{104}$ to $A^{164}$ of CREB (SEQ ID NO:105, accession number X55545).

| GFP | | | | MK2 (from Proline 315 to Serine 362 includes NES) | | | | | | | | | | |
|---|---|---|---|---|---|---|---|---|---|---|---|---|---|---|
| +1 | P | Q | T | P | L | H | T | S | R | V | L | K | E | D | K | (SEQ ID NO:326) |
| 1 | CCT | CAG | ACT | CCA | CTG | CAC | ACC | AGC | CGT | GTC | CTG | AAG | GAG | GAC | AAG | (SEQ ID NO:327) |

| | MK2 | | | | | | | | | | | |
|---|---|---|---|---|---|---|---|---|---|---|---|---|
| +1 | E | R | W | E | D | V | K | E | E | M | T | S | A | L | A |
| 46 | GAA | CGA | TGG | GAG | GAT | GTC | AAG | GAG | GAG | ATG | ACC | AGT | GCC | TTG | GCC |

| | MK2 | | | | | | | | | | | |
|---|---|---|---|---|---|---|---|---|---|---|---|---|
| +1 | T | M | C | V | D | Y | E | Q | I | K | I | K | K | I | E |
| 91 | ACG | ATG | TGT | GTT | GAC | TAT | GAG | CAG | ATC | AAG | ATA | AAG | AAG | ATA | GAA |

| | MK2(S$^{362}$) | | NLS SV40 Large T antigen | | | | | | I$^{104}$ CREB | | | | | |
|---|---|---|---|---|---|---|---|---|---|---|---|---|---|---|
| +1 | D | A | S | P | K | K | K | R | K | V | L | E | I | A | E |
| 136 | GAC | GCA | TCC | CCA | AAG | AAG | AAG | CGA | AAG | GTG | CTC | GAG | ATT | GCA | GAA |

| | | | | CREB | | | | | | | | |
|---|---|---|---|---|---|---|---|---|---|---|---|---|
| +1 | S | E | D | S | Q | E | S | V | D | S | V | T | D | S | Q |
| 181 | AGT | GAA | GAT | TCA | CAG | GAG | TCA | GTG | GAT | AGT | GTA | ACT | GAT | TCC | CAA |

| | | | | CREB | | | | | | | | |
|---|---|---|---|---|---|---|---|---|---|---|---|---|
| +1 | K | R | R | E | I | L | S | R | R | P | S | Y | R | K | I |
| 226 | AAG | CGA | AGG | GAA | ATT | CTT | TCA | AGG | AGG | CCT | TCC | TAC | AGG | AAA | ATT |

| | | | | CREB | | | | | | | | |
|---|---|---|---|---|---|---|---|---|---|---|---|---|
| +1 | L | N | D | L | S | S | D | A | P | G | V | P | R | I | E |
| 271 | TTG | AAT | GAC | TTA | TCT | TCT | GAT | GCA | CCA | GGA | GTG | CCA | AGG | ATT | GAA |

| | | | | CREB | | A$^{164}$ | | | |
|---|---|---|---|---|---|---|---|---|---|
| +1 | E | E | K | S | E | E | E | T | S | A |
| 316 | GAA | GAG | AAG | TCT | GAA | GAG | GAG | ACT | TCA | GCA |

Response to Test Compounds

Protocol: HeLa cells were transiently transfected with recombinant nucleic acid expression vectors expressing the fusion protein. Cells were serum starved for 24 h prior to treatment. Cells were exposed to forskolin for 2 h or PMA for 1 h. Cells were then treated with 3.7% formaldehyde & Hoechst for 20 min. to fix and stain the nuclei, and then washed. Data was collected on ArrayScan II® (Cellomics, Inc. Pittsburgh, Pa.)

Results: The baseline distribution of the fusion protein was biased to the nucleus due to the strong NLS used. Activation by serum or PMA, both growth stimulants, or forskolin, a stimulator of cAMP production, led to a change in localization of the fusion protein to the cytoplasm. Most if not all of the fusion protein was affected. The change in distribution is inhibitable by a 2 hour pretreatment of the cells with 10 uM PKI, a specific inhibitor of both the regulatory domain binding and the catalytic activity of PKA.

Variation in Separation Distance Between the First Localization Domain and the Binding Domain Three variants of the cAMP-dependent protein kinase interaction fusion protein were created wherein the first localization domain and the binding domain were separated by 6, by 8, and by 10 amino acids. In all cases, the distribution of the fusion protein between the nucleus and the cytoplasm changed upon test compound-induced activation in a manner similar to that of the original fusion protein (NLS and binding domain separated by 2 amino acids), although with increasing separation distance between the first localization domain and the binding domain, the magnitude of the change decreased.

Example 2

MAPK Binding Fusion Protein

Introduction

In this example, a fusion protein for detecting the availability for specific binding of MAPK, the protein of interest, is based on the distribution of the fusion protein between the cytoplasm and nucleus. It is constructed such that the detection domain is a GFP, the first localization sequence is a mutated NLS from n-myc, the second localization sequence is an NES from MAPKAP2, and the binding domain is the MAPK binding domain from RSK-1. The NLS and MAPK binding domain are separated by 2 amino acids. Operationally, the binding of MAPK to the binding domain blocks the localization of this fusion protein into the nucleus. Thus, the GFP fluorescence intensity of the nucleus will decrease upon binding MAPK with a comparable increase in cytoplasmic GFP fluorescence. Contacting the cell with a compound that activates MAPK, such as PMA or serum, will activate MAPK by inducing a dissociation of MAPK from MEK1, thus making MAPK available for binding to the RSK-1 binding domain in the fusion protein, and will shift the distribution of the fusion protein from the nucleus to the cytoplasm.

Construction of Fusion Protein

As shown below, this fusion protein was constructed using a GFP, a mutated nuclear localization signal from n-myc, based on human n-myc (Genbank accession number Y00664), the sequence from Proline 315 to Alanine 361 of MAPKAP2 (Genbank accession number X76850), which includes a nuclear export signal (between $D^{328}$ to $E^{351}$, SEQ ID NO:317), and the MAPK binding domain from RSK1 spanning from $S^{718}$ to $T^{733}$ (Genbank accession number L07597).

```
                              GFP    P315  MK2
                                     P   Q   T   P   L   H   T    (SEQ ID NO:328)
                                 1   CCT CAG ACT CCA CTG CAC ACC  (SEQ ID NO:329)

MK2
   +1    S   R   V   L   K   E   D   K   E   R   W   E   D   V   K
   46   AGC CGT GTC CTG AAG GAG GAC AAG GAG CGA TGG GAG GAT GTC AAG

MK2
   +1    E   E   M   T   S   A   L   A   T   M   R   V   D   Y   E
   91   GAG GAG ATG ACC AGT GCC TTG GCC ACG ATG CGT GTT GAC TAT GAG

Mutated n-myc NLS
                MK2
   +1    Q   I   K   I   K   K   I   E   D   A   Q   K   K   R   K
   136  CAG ATC AAG ATA AAG AAG ATA GAA GAC GCA CAG AAG AAG CGT AAG RSK 1 sequence between S718 T733
   +1    S   S   I   L   A   Q   R   R   V   R   K   L   P   S   T
   181  AGT AGT ATC TTG GCC CAG CGT CGA GTC CGA AAG CTG CCT TCC ACT

RSK1
   +1    T   L   A   H   *
   226  ACT TTG GCC CAC TGA
```

A variant of this MAPK binding fusion protein was also prepared. This fusion protein was constructed using a GFP, a nuclear localization signal from the SV 40 large T antigen (SEQ ID NO:145, Genbank accession number J02400), specifically $P^{126}$ to $V^{132}$, the sequence from Glutamic Acid 327 to Isoleucine 353 of MAPKAP2 (Genbank accession number X76850), which includes a nuclear export signal (between $D^{328}$ to $E^{351}$, SEQ ID NO:317), and the MAPK binding domain from RSK1, spanning from $S^{718}$ to $T^{733}$ (Genbank accession number L07597).

cells. Cells were then treated with 3.7% formaldehyde & Hoechst 33342 for 20 minutes to fix and stain the nuclei, and then washed. Data was collected on ArrayScan II® (Cellomics, Inc. Pittsburgh, Pa.).

Results: The baseline distribution of the fusion protein was somewhat biased to the nucleus, due to the relatively strong NLS used. Activation by serum, PMA, or forskolin led to a change in localization of the fusion protein to the cytoplasm. Stimulation by sorbitol, a stress kinase activator, did not

```
                                       MK2 sequence E327-I353
   +1    E   F   G   A   G   D   E   D   K   E   R   W   E   D   V    (SEQ ID NO:330)
    1   GAA TTC GGA GCT GGC GAC GAG GAC AAG GAG CGG TGG GAG GAC GTG   (SEQ ID NO:331)

MK2
   +1    K   E   E   M   T   S   A   L   A   T   M   R   V   D   Y
   46   AAG GAG GAG ATG ACC AGC GCC CTG GCC ACC ATG CGG GTG GAC TAC

MK2
   +1    E   Q   I   L   A   G   Q   P   K   A   N   P   G   A   G
   91   GAG CAG ATT CTA GCC GGA CAG CCA AAG GCC AAC CCC GGC GCC GGA

+1    D   G   Q   P   K   A   N   P   K   R   V   D   P   L   E
   136  GAT GGT CAA CCT AAA GCT AAT CCT AAA CGC GTG GAT CCT CTC GAG

SV40 NLS                              RSK1
   +1    P   K   K   K   R   K   V   K   D   L   S   S   I   L   A
   181  CCA AAG AAG AAG CGG AAG GTG AAA GAT CTA TCA TCC ATC CTG GCC

RSK1 sequence S718-T733
   +1    Q   R   R   V   R   K   L   P   S   T   T   L   V   D   L
   226  CAG CGG CGA GTG AGG AAG TTG CCA TCC ACC ACC CTG GTC GAC CTG

+1    A   H   *
   271  GCC CAC TAA AGC GGC CGC
```

Response to Test Compounds

First Variant

Protocol: HeLa cells were transiently transfected with the fusion protein. Cells were serum starved for 24 hours prior to treatment. Cells were then exposed to PMA (1.5 nM) or sorbitol (200 mM) for 1 hour. For inhibitor treatment, cells were pretreated for 2 hours with 10 uM inhibitor, and then treated with PMA, in parallel with non-inhibitor-treated induce a change in the localization of the fusion protein. Most, if not all, of the fusion protein was affected. The change in distribution was inhibitable by pretreatment of 10 uM PD98059, a specific inhibitor of MAPK activation, but not by SB203580, a specific inhibitor of p38 MAPK activation.

Second Variant

Protocol: HeLa cells were transiently transfected with the fusion protein. Cells were serum starved for 24 hours prior to treatment. Cells were exposed to serum (20%) or PMA (200 nM) for 2 hours. Cells were then treated with 3.7% formaldehyde & Hoechst 33342 for 20 minutes to fix and stain the nuclei, and then washed. Data was collected on ArrayScan II® (Cellomics, Inc. Pittsburgh, Pa.).

Results: The baseline distribution of the fusion protein was biased to the nucleus due to the strong NLS used. Activation by serum or PMA led to a change in localization of the fusion protein to the cytoplasm.

Example 3 c-Jun N-terminal Protein Kinase Fusion Protein

Introduction

In this example, a fusion protein for detecting the availability of specific binding of c-Jun N-terminal kinase (JNK), the protein of interest, is based on the distribution of the fusion protein between the cytoplasm and nucleus. It is constructed such that the detection domain is a GFP, the first localization domain is a modified SV40 T antigen NLS, the second localization domain is an NES from MAPKAP2, and the binding domain is the JNK binding domain from c-jun. Operationally, the binding of JNK blocks the localization of this fusion protein into the nucleus. Thus, the fluorescence intensity of the nucleus will decrease upon binding JNK with a comparable increase in cytoplasmic fluorescence. Contacting the cell with a compound that activates JNK-related stress pathways will shift the distribution of the fusion protein from the nucleus to the cytoplasm. This example illustrates the detection and monitoring of a binding event induced to occur within the cell.

Construction of Fusion Protein

As shown below, this fusion protein was constructed using GFP, a modified nuclear localization signal from SV40 T antigen, the sequence from Proline 315 to Serine 362 of MAPKAP2 (Genbank accession number X76850), which includes a nuclear export signal (between $D^{328}$ to $E^{351}$, SEQ ID NO:317), and the sequence from $P^{30}$ to $L^{60}$ of c-Jun, (accession number J04111), which serves as the JNK binding domain.

Response to Test Compounds

Protocol: HeLa cells were transiently transfected with the fusion protein. Cells were serum starved for 24 hours prior to treatment. Cells were exposed to test compounds known to induce cell stress, including anisomycin (500 nM), sorbitol (300 mM), TNF (tumor necrosis factor, 100 ng/ml), or staurosporine (1 uM), for 1 hour. For inhibitor treatment, cells were pretreated for 2 hours with 10 uM inhibitor then treated with anisomycin, in parallel with non-inhibitor-treated cells. Cells were then treated with 3.7% formaldehyde & Hoechst 33342 for 20 minutes to fix and stain the nuclei, and then washed. Data was collected on ArrayScan II® (Cellomics, Inc. Pittsburgh, Pa.).

Results: The baseline distribution of the fusion protein was balanced between the nucleus and cytoplasm due to the relatively equal strengths of the NLS and NES used. Activation by anisomycin, staurosporine, sorbitol, and to some extent TNF led to a change in localization of the fusion protein to the cytoplasm. Exposure to sorbitol, a stress kinase activator, did not induce a change in localization of the fusion protein. The change in distribution was not affected by pretreatment with 10 uM SB203580, a specific inhibitor of p38 MAPK activation.

Example 4

Fusion Proteins for the Detection of the Availability of a Specific Sequence on DNA In this example, a fusion protein for indicating structural changes in chromatin is prepared. It is constructed such that the detection domain is a GFP, the first localization domain is a nuclear localization signal (NLS) from NFKB (SEQ ID NO:336, Genbank accession # M58603, amino acids $Q^{360}-K^{365}$), the second localization domain is a nuclear export signal (NES) from MEK1 (SEQ ID NO:337, Genbank accession # L11284, amino acids $L^{33}-L^{42}$), and the binding domain is the DNA binding domain from Sp1 (SEQ ID NO:338, Genbank accession # AF252284; amino acids $K^{619}-K^{710}$). (See table below.) The fluorescence intensity within the nucleus relative to that of the cytoplasm will change with the availability of the DNA binding sequence

```
GFP               MK2 (P³¹⁵ to S³⁶²) includes MK2 NES (D³²⁸ to E³⁵¹)
     +1       P    Q    T    P    L    H    T    S    R    V    L    K    E   (SEQ ID NO:332)
      1      CCT  CAG  ACT  CCA  CTG  CAC  ACC  AGC  CGT  GTC  CTG  AAG  GAG  (SEQ ID NO:333)

+1       D    K    E    R    W    E    D    V    K    E    E    M    T    S    A
     46      GAC  AAG  GAA  CGA  TGG  GAG  GAT  GTC  AAG  GAG  GAG  ATG  ACC  AGT  GCC

+1       L    A    T    M    R    V    D    Y    E    Q    I    K    I    K    K
     91      TTG  GCC  ACG  ATG  CGT  GTT  GAC  TAT  GAG  CAG  ATC  AAG  ATA  AAG  AAG c-Jun (P³⁰ to L⁶⁰)
     +1       I    E    D    A    S    N    P    S    R    P    K    I    L    K    Q
     136     ATA  GAA  GAC  GCA  TCC  AAC  CCT  TCT  AGA  CCC  AAG  ATC  CTG  AAA  CAG

+1       S    M    T    Q    N    L    A    V    P    V    G    S    L    K    P
     181     AGC  ATG  ACC  CAG  AAC  CTG  GCC  GTC  CCA  GTG  GGG  AGC  CTG  AAG  CCG

Modified SV40 T-antigen NLS
     +1       H    L    C    A    K    N    S    D    L    K    R    R    K    K    A
     226     CAC  CTC  TGC  GCC  AAG  AAC  TCG  GAC  CTC  AAG  CGT  CGT  AAG  AAG  GCC

+1       H    *
     271     CAC  TGA
```

5'-GGG-GCG-GGG-C-3' (SEQ ID NO:334) in the chromatin in response to various treatments.

In another variation, a similar fusion protein is constructed, with the difference that the binding domain is the DNA binding domain from Zif268 (SEQ ID NO:339, Genbank accession # NM_007913, amino acids $Y^{346}$–$H^{16}$). The changes in the fluorescence intensity within the nucleus relative to that of the cytoplasm will report changes of the availability of the sequence 5'-GCG-TGG-GCG-3' (SEQ ID NO:335) in the nucleus in response various treatments.

protein. An expression reporter gene analogous to those expressing luciferase or b-lactamase could be constructed by placing, for example, a single-chain antibody, specific to a particular epitope, under the control of a promoter. A fusion protein for detecting increased expression driven by the chosen promoter would have as its binding domain the epitope specific for the antibody. Thus, as the gene is translated and new antibody molecules are expressed, they would bind to the fusion protein, thereby inducing redistribution of the fusion protein.

| Name | Genbank Accession Number | Sequence | SEQ ID NO. | Notes |
|---|---|---|---|---|
| NFkB | M58603 | QRKRQK | 336 | $Q^{360}$-$K^{365}$; NLS |
| MEK1 | L11284 | LQKKLEELEL | 337 | $L^{33}$-$L^{42}$; NES |
| Sp1 | AF252284 | KKKQHICHIQGCGKVYGKTSHLRAH LRWHTGERPFMCTWSYCGKRFTRSD ELQRHKRTHTGEKKFACPECPKRFM RSDHLSKHIKTHQNKK | 338 | $K^{619}$-$K^{710}$; DNA binding domain |
| Zif268 | NM_007913 | YACPVESCDRRFSRSDELTRHIRIHTG QKPFQCRICMRNFSRSDHLTTHIRTH TGEKPFACDICGRKFARSDERKRHTK IH | 339 | $Y^{346}$-$H^{416}$; DNA binding domain |

Example 5

Fusion Proteins for the Screening of an Exogenous Library

For screening libraries for potential binders to specific binding domains, cells may be transfected with a cDNA library of interest. The resulting cell library is then loaded with an externally deliverable fusion protein containing the appropriate binding domain. The cells are then screened for relative distribution of fusion protein. Those cells that show a distribution of the fusion protein different from cells that do not express the cDNA represent candidates of proteins that interact with the chosen binding domain. Alternatively, a cell line could be developed that stably expresses a fusion protein comprising the selected binding domain. That cell line could be used as the basis for transfecting, for example, transiently, the cDNA library. Analysis of the distribution of the detectable signal would identify binding partners. No specific modifications of the cDNA library are required in this example of the invention.

Example 6

Fusion Proteins for Monitoring Protein and RNA Expression

Fusion proteins based on the invention can be used to detect and measure the expression of either a protein of interest or the mRNA encoding the protein of interest. To detect expression of a protein of interest, the fusion protein would contain a binding domain for the protein of interest such that upon expression of the protein of interest, the protein of interest would bind to the fusion protein and induce a change in the subcellular distribution of the fusion protein. An expression reporter gene analogous to those expressing luciferase or b-lactamase could be constructed by placing, for example, a single-chain antibody, specific to a particular epitope, under the control of a promoter. A fusion protein for detecting increased expression driven by the chosen promoter would have as its binding domain the epitope specific for the antibody. Thus, as the gene is translated and new antibody molecules are expressed, they would bind to the fusion protein, thereby inducing redistribution of the fusion protein.

To detect the MRNA of interest, the fusion protein would contain a domain capable of binding a specific sequence of RNA, and the specific RNA would bind to the fusion protein and induce a change in the subcellular distribution of the fusion protein. An expression reporter gene analogous to using luciferase or b-lactamase could be constructed by utilizing the specific DNA sequence that, when transcribed would be expressed in the resultant MRNA, as the sequence specific for the binding domain of the fusion protein. Thus, as the gene is transcribed and the mRNA molecules are expressed, they would bind to the fusion protein, thereby inducing redistribution of the fusion protein.

Example 7

Fusion Proteins for Monitoring Concentrations of Cofactors and Metabolites

In another example, this invention could be used to detect metabolites, such as cAMP, within living cells. By exploiting the dependence of particular binding interactions on the availability of a metabolite, the amount of binding is an indirect measure of the amount of metabolite. For example, the catalytic domain of PKA (cPKA) binds to the regulatory domain of PKA (rPKA) in the absence of cAMP. With an increase in the concentration of cAMP, cPKA dissociates from rPKA. A fusion protein could be designed wherein the binding domain is the rPKA-binding domain from cPKA and is located proximal to an NLS, such that upon binding rPKA localization of the fusion protein into the nucleus is blocked. This would provide a means by which to measure the relative changes in the concentration of cAMP by monitoring the relative distribution of the fusion protein. Since cAMP binds to rPKA preventing it from binding to the rPKA-binding domain in the fusion protein, the degree of binding reflects the relative concentration of cAMP within the cell requiring only a single detection domain. One of skill in the art would understand that other fusion proteins based on systems of interacting proteins that are dependent on the amount of specific metabolites present can be constructed.

Example 8

Fusion Proteins for Monitoring Post-Translational Modifications

In an example analogous to the previous example, the invention can be used to monitor post-translational modifications. A post-translational event, such as phosphorylation, can be monitored indirectly by monitoring any protein binding interaction dependent on the post-translational modification. Thus, for example, when binding of a protein can only occur if the binding domain is phosphorylated, then the relative distribution of a fusion protein comprising the binding domain reflects the level of phosphorylation activity.

In another variant for monitoring post-translational modification, a fusion protein is constructed such that the detection domain is a GFP, the first localization domain is a nuclear localization signal (NLS), the second localization domain is a nuclear export signal (NES), and the binding domain is the phosphorylation site from Elk-1 specific for MAPK mediated phosphorylation. The covalent attachment of a phosphate proximal to the NLS sterically blocks the nuclear localization. The fluorescence intensity within the nucleus relative to that of the cytoplasm will change upon phosphorylation by MAPK in response to various treatments.

In yet another variant of a fusion protein for monitoring post-translational modification, a fusion protein is constructed such that the detection domain is a GFP, the first localization domain is an NLS, the second localization domain is an NES, and the binding domain includes a covalent binding site, the phosphorylation site from Elk-1 specific for MAPK mediated phosphorylation, and a non-covalent binding site, the binding domain of RSK-1, separated from the NLS and NES. The fluorescence intensity within the nucleus relative to that of the cytoplasm will change upon phosphorylation of the fusion protein by MAPK in response to various treatments. The benefit of this variant is the non-covalent binding of MAPK to the fusion protein, placing it in close proximity to the covalent binding domain.

REFERENCES CITED

Bessert, D. A., Gutridge, K. L., Dunbar, J. C. and Carlock, L. R. (1995) The identification of a functional nuclear localization signal in the Huntington disease protein. *Brain Res Mol Brain Res*, 33, 165–73.

Blauer, M., Husgafvel, S., Syvala, H., Tuohimaa, P. and Ylikomi, T. (1999) Identification of a nuclear localization signal in activin/inhibin betaA subunit; intranuclear betaA in rat spermatogenic cells. *Biol Reprod*, 60, 588–93.

Bonifaci, N., Moroianu, J., Radu, A. and Blobel, G. (1997) Karyopherin beta2 mediates nuclear import of a mRNA binding protein. *Proc Natl Acad Sci USA*, 94, 5055–60.

Bouvier, D. and Baldacci, G. (1995) The N-terminus of fission yeast DNA polymerase alpha contains a basic pentapeptide that acts in vivo as a nuclear localization signal. *Mol Biol Cell*, 6, 1697–705.

Carriere, C., Plaza, S., Caboche, J., Dozier, C., Bailly, M., Martin, P. and Saule, S. (1995) Nuclear localization signals, DNA binding, and transactivation properties of quail Pax-6 (Pax-QNR) isoforms. *Cell Growth Differ*, 6, 1531–40.

Chan, C. K., Hubner, S., Hu, W. and Jans, D. A. (1998) Mutual exclusivity of DNA binding and nuclear localization signal recognition by the yeast transcription factor GAL4: implications for nonviral DNA delivery. *Gene Ther*, 5, 1204–12.

Chang, D., Haynes, J. I. d., Brady, J. N. and Consigli, R. A. (1992a) Identification of a nuclear localization sequence in the polyomavirus capsid protein VP2. *Virology*, 191, 978–83.

Chang, D., Haynes, J.I.d., Brady, J. N. and Consigli, R. A. (1992b) The use of additive and subtractive approaches to examine the nuclear localization sequence of the polyomavirus major capsid protein VP1. *Virology*, 189, 821–7.

Chang, S. C., Yen, J. H., Kang, H. Y., Jang, M. H. and Chang, M. F. (1994) Nuclear localization signals in the core protein of hepatitis C virus. *Biochem Biophys Res Commun*, 205, 1284–90.

Dang, C. V. and Lee, W. M. (1989) Nuclear and nucleolar targeting sequences of c-erb-A, c-myb, N-myc, p53, HSP70, and HIV tat proteins. *J Biol Chem*, 264, 18019–23.

Eguchi, H., Ikuta, T., Tachibana, T., Yoneda, Y. and Kawajiri, K. (1997) A nuclear localization signal of human aryl hydrocarbon receptor nuclear translocator/hypoxia-inducible factor 1 beta is a novel bipartite type recognized by the two components of nuclear pore-targeting complex. *J Biol Chem*, 272, 17640–7.

Gao, M. and Knipe, D. M. (1992) Distal protein sequences can affect the function of a nuclear localization signal. *Mol Cell Biol*, 12, 1330–9.

Gilmore, T. D. and Temin, H. M. (1988) v-rel oncoproteins in the nucleus and in the cytoplasm transform chicken spleen cells. *J Virol*, 62, 703–14.

Hall, M. N., Hereford, L. and Herskowitz, I. (1984) Targeting of *E. coli* beta-galactosidase to the nucleus in yeast. *Cell*, 36, 1057–65.

Hicks, G. R. and Raikhel, N. V. (1995) Nuclear localization signal binding proteins in higher plant nuclei. *Proc Natl Acad Sci U S A*, 92, 734–8.

Hsieh, J. C., Shimizu, Y., Minoshima, S., Shimizu, N., Haussler, C. A., Jurutka, P. W. and Haussler, M. R. (1998) Novel nuclear localization signal between the two DNA-binding zinc fingers in the human vitamin D receptor. *J Cell Biochem*, 70, 94–109.

Ide, Y., Zhang, L., Chen, M., Inchauspe, G., Bahl, C., Sasaguri, Y. and Padmanabhan, R. (1996) Characterization of the nuclear localization signal and subcellular distribution of hepatitis C virus nonstructural protein NS5A. *Gene*, 182, 203–11.

Irie, Y., Yamagata, K., Gan, Y., Miyamoto, K., Do, E., Kuo, C. H., Taira, E. and Miki, N. (2000) Molecular cloning and characterization of Amida, a novel protein which interacts with a neuron-specific immediate early gene product arc, contains novel nuclear localization signals, and causes cell death in cultured cells. *J Biol Chem*, 275, 2647–53.

Kalderon, D., Roberts, B. L., Richardson, W. D. and Smith, A. E. (1984) A short amino acid sequence able to specify nuclear location. *Cell*, 39, 499–509.

Kaneko, H., Orii, K. O., Matsui, E., Shimozawa, N., Fukao, T., Matsumoto, T., Shimamoto, A., Furuichi, Y., Hayakawa, S., Kasahara, K. and Kondo, N. (1997) BLM (the causative gene of Bloom syndrome) protein translocation into the nucleus by a nuclear localization signal. *Biochem Biophys Res Commun*, 240, 348–53.

Kato, G. J., Lee, W. M., Chen, L. L. and Dang, C. V. (1992) Max: functional domains and interaction with c-Myc. *Genes Dev*, 6, 81–92.

Knuehl, C., Seelig, A., Brecht, B., Henklein, P. and Kloetzel, P. M. (1996) Functional analysis of eukaryotic 20S proteasome nuclear localization signal. *Exp Cell Res*, 225, 67–74.

Koike, M., Ikuta, T., Miyasaka, T. and Shiomi, T. (1999) The nuclear localization signal of the human Ku70 is a variant bipartite type recognized by the two components of nuclear pore-targeting complex [published erratum appears in Exp Cell Res 1999 Nov 25;253(1):280]. *Exp Cell Res*, 250, 401–13.

Kukolj, G., Katz, R. A. and Skalka, A. M. (1998) Characterization of the nuclear localization signal in the avian sarcoma virus integrase. *Gene*, 223, 157–63.

Liang, S. H. and Clarke, M. F. (1999) The nuclear import of p53 is determined by the presence of a basic domain and its relative position to the nuclear localization signal. *Oncogene*, 18, 2163–6.

Liu, M. T., Hsu, T. Y., Chen, J. Y. and Yang, C. S. (1998) Epstein-Barr virus DNase contains two nuclear localization signals, which are different in sensitivity to the hydrophobic regions. *Virology*, 247, 62–73.

Lyons, R. H., Ferguson, B. Q. and Rosenberg, M. (1987) Pentapeptide nuclear localization signal in adenovirus Ela. *Mol Cell Biol*, 7, 2451–6.

Mattaj, I. W. and Englmeier, L. (1998) Nucleocytoplasmic transport: the soluble phase. *Annu Rev Biochem*, 67, 265–306.

Michael, W. M., Eder, P. S. and Dreyfuss, G. (1997) The K nuclear shuttling domain: a novel signal for nuclear import and nuclear export in the hnRNP K protein. *Embo J*, 16, 3587–98.

Miyamoto, Y., Imamoto, N., Sekimoto, T., Tachibana, T., Seki, T., Tada, S., Enomoto, T. and Yoneda, Y. (1997) Differential modes of nuclear localization signal (NLS) recognition by three distinct classes of NLS receptors. *J Biol Chem*, 272, 26375–81.

Mizuno, T., Okamoto, T., Yokoi, M., Izumi, M., Kobayashi, A., Hachiya, T., Tamai, K., Inoue, T. and Hanaoka, F. (1996) Identification of the nuclear localization signal of mouse DNA primase: nuclear transport of p46 subunit is facilitated by interaction with p54 subunit. *J Cell Sci*, 109, 2627–36.

Moede, T., Leibiger, B., Pour, H. G., Berggren, P. and Leibiger, I. B. (1999) Identification of a nuclear localization signal, RRMKWKK, in the homeodomain transcription factor PDX-1. *FEBS Lett*, 461, 229–34.

Moreland, R. B., Langevin, G. L., Singer, R. H., Garcea, R. L. and Hereford, L. M. (1987) Amino acid sequences that determine the nuclear localization of yeast histone 2B. *Mol Cell Biol*, 7, 4048–57.

Moreland, R. B., Nam, H. G., Hereford, L. M. and Fried, H. M. (1985) Identification of a nuclear localization signal of a yeast ribosomal protein. *Proc Natl Acad Sci U S A*, 82, 6561–5.

Nederlof, P. M., Wang, H. R. and Baumeister, W. (1995) Nuclear localization signals of human and Thermoplasma proteasomal alpha subunits are functional in vitro. *Proc Natl Acad Sci U S A*, 92, 12060–4.

Palmeri, D. and Malim, M. H. (1999) Importin beta can mediate the nuclear import of an arginine-rich nuclear localization signal in the absence of importin alpha. *Mol Cell Biol*, 19, 1218–25.

Prieve, M. G., Guttridge, K. L., Munguia, J. and Waterman, M. L. (1998) Differential importin-alpha recognition and nuclear transport by nuclear localization signals within the high-mobility-group DNA binding domains of lymphoid enhancer factor 1 and T-cell factor 1. *Mol Cell Biol*, 18, 4819–32.

Rhee, S. K., Icho, T. and Wickner, R. B. (1989) Structure and nuclear localization signal of the SKI3 antiviral protein of *Saccharomyces cerevisiae*. *Yeast*, 5, 149–58.

Richardson, W. D., Roberts, B. L. and Smith, A. E. (1986) Nuclear location signals in polyoma virus large-T. *Cell*, 44, 77–85.

Robbins, J., Dilworth, S. M., Laskey, R. A. and Dingwall, C. (1991) Two interdependent basic domains in nucleoplasmin nuclear targeting sequence: identification of a class of bipartite nuclear targeting sequence. *Cell*, 64, 615–23.

Rubtsov, Y. P., Zolotukhin, A. S., Vorobjev, I. A., Chichkova, N. V., Pavlov, N. A., Karger, E. M., Evstafieva, A. G., Felber, B. K. and Vartapetian, A. B. (1997) Mutational analysis of human prothymosin alpha reveals a bipartite nuclear localization signal. *FEBS Lett*, 413, 135–41.

Schmidt-Zachmann, M. S. and Nigg, E. A. (1993) Protein localization to the nucleolus: a search for targeting domains in nucleolin. *J Cell Sci*, 105, 799–806.

Schreiber, V., Molinete, M., Boeuf, H., de Murcia, G. and Menissier-de Murcia, J. (1992) The human poly(ADP-ribose) polymerase nuclear localization signal is a bipartite element functionally separate from DNA binding and catalytic activity. *Embo J*, 11, 3263–9.

Schwemmle, M., Jehle, C., Shoemaker, T. and Lipkin, W. I. (1999) Characterization of the major nuclear localization signal of the Borna disease virus phosphoprotein. *J Gen Virol*, 80, 97–100.

Shoya, Y., Kobayashi, T., Koda, T., Ikuta, K., Kakinuma, M. and Kishi, M. (1998) Two proline-rich nuclear localization signals in the amino- and carboxyl-terminal regions of the Boma disease virus phosphoprotein. *J Virol*, 72, 9755–62.

Sock, E., Enderich, J., Rosenfeld, M. G. and Wegner, M. (1996) Identification of the nuclear localization signal of the POU domain protein Tst-1/Oct 6. *J Biol Chem*, 271, 17512–8.

Somasekaram, A., Jarmuz, A., How, A., Scott, J. and Navaratnam, N. (1999) Intracellular localization of human cytidine deaminase. Identification of a functional nuclear localization signal. *J Biol Chem*, 274, 28405–12.

Sudbeck, P. and Scherer, G. (1997) Two independent nuclear localization signals are present in the DNA-binding high-mobility group domains of SRY and SOX9. *J Biol Chem*, 272, 27848–52.

Tinland, B., Koukolikova-Nicola, Z., Hall, M. N. and Hohn, B. (1992) The T-DNA-linked VirD2 protein contains two distinct functional nuclear localization signals. *Proc Natl Acad Sci USA*, 89, 7442–6.

Truant, R. and Cullen, B. R. (1999) The arginine-rich domains present in human immunodeficiency virus type 1 Tat and Rev function as direct importin beta-dependent nuclear localization signals. *Mol Cell Biol*, 19, 1210–7.

Truant, R., Fridell, R. A., Benson, R. E., Bogerd, H. and Cullen, B. R. (1998) Identification and functional characterization of a novel nuclear localization signal present in the yeast Nab2 poly(A)+RNA binding protein. *Mol Cell Biol*, 18, 1449–58.

Underwood, M. R. and Fried, H. M. (1990) Characterization of nuclear localizing sequences derived from yeast ribosomal protein L29. *Embo J*, 9, 91–9.

Vandromme, M., Cavadore, J. C., Bonnieu, A., Froeschle, A., Lamb, N. and Fernandez, A. (1995) Two nuclear localization signals present in the basic-helix 1 domains of MyoD promote its active nuclear translocation and can function independently. *Proc Natl Acad Sci USA,* 92, 4646–50.

Vihinen-Ranta, M., Kakkola, L., Kalela, A., Vilja, P. and Vuento, M. (1997) Characterization of a nuclear localization signal of canine parvovirus capsid proteins. *Eur J Biochem,* 250, 389–94.

Wang, P., Palese, P. and O'Neill, R. E. (1997) The NPI-1/NPI-3 (karyopherin alpha) binding site on the influenza a virus nucleoprotein NP is a nonconventional nuclear localization signal. *J Virol,* 71, 1850–6.

Wang, Y., MacDonald, J. I. and Kent, C. (1995) Identification of the nuclear localization signal of rat liver CTP:phosphocholine cytidylyltransferase. *J Biol Chem,* 270, 354–60.

Weber, F., Kochs, G., Gruber, S. and Haller, O. (1998) A classical bipartite nuclear localization signal on Thogoto and influenza A virus nucleoproteins. *Virology,* 250, 9–18.

Welch, K., Franke, J., Kohler, M. and Macara, I. G. (1999) RanBP3 contains an unusual nuclear localization signal that is imported preferentially by importin-alpha3. *Mol Cell Biol,* 19, 8400–11.

Wu, J., Zhou, L., Tonissen, K., Tee, R. and Artzt, K. (1999) The quaking I-5 protein (QKI-5) has a novel nuclear localization signal and shuttles between the nucleus and the cytoplasm. *J Biol Chem,* 274, 29202–10.

Wychowski, C., Benichou, D. and Girard, M. (1986) A domain of SV40 capsid polypeptide VP1 that specifies migration into the cell nucleus. *Embo J,* 5, 2569–76.

Wychowski, C., Benichou, D. and Girard, M. (1987) The intranuclear location of simian virus 40 polypeptides VP2 and VP3 depends on a specific amino acid sequence. *J Virol,* 61, 3862–9.

Youssoufian, H., Gharibyan, V. and Qatanani, M. (1999) Analysis of epitope-tagged forms of the dyskeratosis congenital protein (dyskerin): identification of a nuclear localization signal. *Blood Cells Mol Dis,* 25, 305–9.

Yu, Z., Lee, C. H., Chinpaisal, C. and Wei, L. N. (1998) A constitutive nuclear localization signal from the second zinc-finger of orphan nuclear receptor TR2. *J Endocrinol,* 159, 53–60.

Zacksenhaus, E., Bremner, R., Phillips, R. A. and Gallie, B. L. (1993) A bipartite nuclear localization signal in the retinoblastoma gene product and its importance for biological activity. *Mol Cell Biol,* 13, 4588–99.

We claim:

1. A recombinant nucleic acid molecule encoding a recombinant fusion protein for detecting binding of a molecule of interest, comprising the following operably linked regions in frame relative to each other:
   a) a first nucleic acid sequence encoding a detection domain;
   b) a second nucleic acid sequence encoding a first localization domain; and
   c) a third nucleic acid sequence encoding a binding domain for the molecule of interest, wherein the binding domain is one or both of a covalent binding domain and a non-covalent binding domain;
   wherein the third nucleic acid sequence encoding the non-covalent binding domain, when present, is separated from the second nucleic acid sequence by 0–60 nucleotides, and wherein the third nucleic acid sequence encoding the covalent binding domain, when present, is separated from the second nucleic acid sequence by 0–12 nucleotides,
   wherein the third nucleic acid sequence encodes a binding domain consisting of an amino acid sequence selected from the group consisting of SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, and SEQ ID NO:115, SEQ ID NO:117, SEQ ID NO:119, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:141, SEQ ID NO:143, SEQ ID NO:310, SEQ ID NO:311, SEQ ID NO:312, SEQ ID NO:313, SEQ ID NO:314, SEQ ID NO:336, SEQ ID NO:337, SEQ ID NO:338, SEQ ID NO:339, SEQ ID NO:341, SEQ ID NO:343, SEQ ID NO:345, SEQ ID NO:347, SEQ ID NO:349, SEQ ID NO:350, SEQ ID NO:352, SEQ ID NO:354, SEQ ID NO:356, SEQ ID NO:358, SEQ ID NO:360, SEQ ID NO:362, SEQ ID NO:364, and SEQ ID NO:366; and
   wherein the second nucleic acid sequence and the third nucleic acid sequence do not both occur in a single non-recombinant nucleic acid molecule, or do not both occur in a single non-recombinant nucleic acid molecule with the same spacing as in the recombinant nucleic acid molecule encoding a recombinant fusion protein for detecting binding of a molecule of interest.

2. A recombinant nucleic acid molecule encoding a recombinant fusion protein for detecting binding of a molecule of interest, comprising the following operably linked regions in frame relative to each other:
   a) a first nucleic acid sequence encoding a detection domain;
   b) a second nucleic acid sequence encoding a first localization domain;
   c) a third nucleic acid sequence encoding a binding domain for the molecule of interest, wherein the binding domain is one or both of a covalent binding domain and a non-covalent binding domain; and
   d) a fourth nucleic acid sequence encoding a second localization domain
   wherein the third nucleic acid sequence encoding the non-covalent binding domain, when present, is separated from the second nucleic acid sequence by 0–60 nucleotides, and wherein the third nucleic acid sequence encoding the covalent binding domain, when present, is separated from the second nucleic acid sequence by 0–12 nucleotides
   wherein the fourth nucleic acid sequence is separated from the third nucleic acid sequence by more than 60 nucleotides;
   wherein the first localization domain and the second localization domain do not target the recombinant fusion protein to an identical subcellular compartment; and
   wherein the second nucleic acid sequence, the third nucleic acid sequence, and the fourth nucleic acid sequence do not all occur in a single non-recombinant nucleic acid molecule, or do not all occur in a single non-recombinant nucleic acid molecule with the same spacing as in the recombinant nucleic acid molecule encoding a recombinant fusion protein for detecting binding of a molecule of interest.

3. The recombinant nucleic acid molecule of claim 1 wherein the third nucleic acid sequence encodes a binding domain for a molecule of interest selected from the group consisting of nucleic acid, protein, and lipid.

4. The recombinant nucleic acid molecule of claim 1 wherein the third nucleic acid sequence encodes a binding domain for a protein of interest.

5. The recombinant nucleic acid molecule of claim 1 wherein the binding domain does not contain a cleavage site.

6. The recombinant nucleic acid molecule of claim 2 wherein the third nucleic acid sequence encodes a binding domain consisting of an amino acid sequence selected from the group consisting of SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, and SEQ ID NO:115, SEQ ID NO:117, SEQ ID NO:119, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:141, SEQ ID NO:143, SEQ ID NO:310, SEQ ID NO:311, SEQ ID NO:312, SEQ ID NO:313, SEQ ID NO:314, SEQ ID NO:336, SEQ ID NO:337, SEQ ID NO:338, SEQ ID NO:339, SEQ ID NO:341, SEQ ID NO:343, SEQ ID NO:345, SEQ ID NO:347, SEQ ID NO:349, SEQ ID NO:350, SEQ ID NO:352, SEQ ID NO:354, SEQ ID NO:356, SEQ ID NO:358, SEQ ID NO:360, SEQ ID NO:362, SEQ ID NO:364, and SEQ ID NO:366.

7. A recombinant nucleic acid molecule comprising the following operably linked regions in frame relative to each other:
   a) a first nucleic acid sequence encoding a detection domain;
   b) a second nucleic acid sequence encoding a first localization domain; and
   c) a third nucleic acid sequence that comprises one or more restriction enzyme recognition sites that are unique to the recombinant nucleic acid molecule;
   wherein the third nucleic acid sequence is separated from the second nucleic acid sequence by 0–60 nucleotides; and
   wherein the second nucleic acid sequence and the third nucleic acid sequence do not both occur in a single non-recombinant nucleic acid molecule, or do not both occur in a single non-recombinant nucleic acid molecule with the same spacing as in the recombinant nucleic acid molecule.

8. The recombinant nucleic acid molecule of claim 7 further comprising a fourth nucleic acid sequence encoding a second localization domain,
   wherein the first nucleic acid sequence, the second nucleic acid sequence, the third nucleic acid sequence, and the fourth nucleic acid sequence are operably linked;
   and wherein the fourth nucleic acid sequence is separated from the third nucleic acid sequence by more than 60 nucleotides;
   wherein the first and second localization domains do not target the recombinant fusion protein to an identical subcellular compartment; and
   wherein the second nucleic acid sequence, the third nucleic acid sequence, and the fourth nucleic acid sequence do not all occur in a single non-recombinant nucleic acid molecule, or do not all occur in a single non-recombinant nucleic acid molecule with the same spacing as in the recombinant nucleic acid molecule.

9. A recombinant expression vector comprising nucleic acid control sequences operatively linked to the recombinant nucleic acid molecule of claim 1.

10. A recombinant expression vector comprising nucleic acid control sequences operatively linked to the recombinant nucleic acid molecule of claim 7.

11. A genetically engineered host cell that has been transfected with the recombinant expression vector of claim 9.

12. A genetically engineered host cell that has been transfected with the recombinant expression vector of claim 10.

13. The recombinant nucleic acid molecule of claim 1, wherein the binding domain comprises a protein kinase binding domain.

14. The recombinant nucleic acid molecule of claim 1, wherein the first localization domain comprises a nuclear localization domain.

15. The recombinant nucleic acid molecule of claim 13, wherein the first localization domain comprises a nuclear localization domain.

16. The recombinant nucleic acid molecule of claim 2, wherein the binding domain comprises a protein kinase binding domain.

17. The recombinant nucleic acid molecule of claim 2, wherein either the first localization domain or the second localization domain comprises a nuclear localization domain.

18. The recombinant nucleic acid molecule of claim 16, wherein either the first localization domain or the second localization domain comprises a nuclear localization domain.

19. The recombinant nucleic acid molecule of claim 2, wherein either the first localization domain or the second localization domain comprises a nuclear localization domain, and the other localization domain comprises a nuclear export domain.

20. The recombinant nucleic acid molecule of claim 16, wherein either the first localization domain or the second localization domain comprises a nuclear localization domain, and the other localization domain comprises a nuclear export domain.

21. The recombinant nucleic acid molecule of claim 7, wherein the first localization domain comprises a nuclear localization domain.

22. The recombinant nucleic acid molecule of claim 8, wherein either the first localization domain or the second localization domain comprises a nuclear localization domain, and the other localization domain comprises a nuclear export domain.

23. The recombinant nucleic acid molecule of claim 1, wherein the binding domain comprises a non-covalent binding domain.

24. The recombinant nucleic acid molecule of claim 1, wherein the binding domain comprises a covalent binding domain.

25. The recombinant nucleic acid molecule of claim 2 wherein the third nucleic acid sequence encodes a binding domain for a molecule of interest selected from the group consisting of nucleic acid, protein, and lipid.

26. The recombinant nucleic acid molecule of claim 2 wherein the third nucleic acid sequence encodes a binding domain for a protein of interest.

27. The recombinant nucleic acid molecule of claim 2 wherein the binding domain does not contain a cleavage site.

28. A recombinant expression vector comprising nucleic acid control sequences operatively linked to the recombinant nucleic acid molecule of claim 2.

29. A genetically engineered host cell that has been transfected with the recombinant expression vector of claim 28.

30. The recombinant nucleic acid molecule of claim 2, wherein the binding domain comprises a non-covalent binding domain.

31. The recombinant nucleic acid molecule of claim 2, wherein the binding domain comprises a covalent binding domain.

* * * * *

SEQUENCE LISTING

```
<160> NUMBER OF SEQ ID NOS: 366

<210> SEQ ID NO 1
<211> LENGTH: 23
<212> TYPE: PRT
<213> ORGANISM: Artificial Sequence
<220> FEATURE:
<223> OTHER INFORMATION: Organelle targeting sequence

<400> SEQUENCE: 1

Met Ser Thr Val His Glu Ile Leu Cys Lys Leu Ser Leu Glu Gly Val
1               5                   10                  15

His Ser Thr Pro Pro Ser Ala
            20

<210> SEQ ID NO 2
<211> LENGTH: 69
<212> TYPE: DNA
<213> ORGANISM: Artificial Sequence
<220> FEATURE:
<223> OTHER INFORMATION: Sequence encoding for organelle targeting
      sequence

<400> SEQUENCE: 2
atgtctactg tccacgaaat cctgtgcaag ctcagcttgg agggtgttca ttctacaccc        60
ccaagtgcc                                                                69

<210> SEQ ID NO 3
<211> LENGTH: 32
<212> TYPE: PRT
<213> ORGANISM: Artificial Sequence
<220> FEATURE:
<223> OTHER INFORMATION: organelle targeting sequence

<400> SEQUENCE: 3

Met Gly Cys Thr Leu Ser Ala Glu Asp Lys Ala Ala Val Glu Arg Ser
1               5                   10                  15
```

Lys Met Ile Asp Arg Asn Leu Arg Glu Asp Gly Glu Lys Ala Ala Arg
            20                  25                  30

<210> SEQ ID NO 4
<211> LENGTH: 99
<212> TYPE: DNA
<213> ORGANISM: Artificial Sequence
<220> FEATURE:
<223> OTHER INFORMATION: Sequence encoding for organelle targeting
      sequence

<400> SEQUENCE: 4
atgggatcta cattaagcgc agaagacaaa gcagcagtag aaagaagcaa aatgatagac      60
agaaacttat taagagaaga cggagaaaaa gctgctaga                            99

<210> SEQ ID NO 5
<211> LENGTH: 6
<212> TYPE: PRT
<213> ORGANISM: Artificial Sequence
<220> FEATURE:
<223> OTHER INFORMATION: Organelle targeting sequence

<400> SEQUENCE: 5

Arg Arg Lys Arg Gln Lys
1               5

<210> SEQ ID NO 6
<211> LENGTH: 18
<212> TYPE: DNA
<213> ORGANISM: Artificial Sequence
<220> FEATURE:
<223> OTHER INFORMATION: Sequence encoding organelle targeting sequence

<400> SEQUENCE: 6
agaaggaaac gacaaaag                                                   18

<210> SEQ ID NO 7
<211> LENGTH: 30
<212> TYPE: PRT
<213> ORGANISM: Artificial Sequence
<220> FEATURE:
<223> OTHER INFORMATION: Organelle targeting sequence

<400> SEQUENCE: 7

Arg Lys Arg Ile Arg Thr Tyr Leu Lys Ser Cys Arg Arg Met Lys Arg
1               5                   10                  15

Ser Gly Phe Glu Met Ser Arg Pro Ile Pro Ser His Leu Thr
            20                  25                  30

<210> SEQ ID NO 8
<211> LENGTH: 90
<212> TYPE: DNA
<213> ORGANISM: Artificial sequence
<220> FEATURE:
<223> OTHER INFORMATION: Sequence encoding organelle targeting sequence

<400> SEQUENCE: 8
agaaaacgta tacgtactta cctcaagtcc tgcaggcgga tgaaaagaag tggttttgag      60
atgtctcgac ctattccttc ccaccttact                                      90

<210> SEQ ID NO 9
<211> LENGTH: 29
<212> TYPE: PRT
<213> ORGANISM: Artificial Sequence
<220> FEATURE:

-continued

<223> OTHER INFORMATION: Organelle targeting sequence

<400> SEQUENCE: 9

Met Ser Val Leu Thr Pro Leu Leu Arg Gly Leu Thr Gly Ser Ala
1               5                   10                  15

Arg Arg Leu Pro Val Pro Arg Ala Leu Ile His Ser Leu
            20                  25

<210> SEQ ID NO 10
<211> LENGTH: 87
<212> TYPE: DNA
<213> ORGANISM: Artificial Sequence
<220> FEATURE:
<223> OTHER INFORMATION: Sequence encoding organelle targeting sequence

<400> SEQUENCE: 10
atgtccgtcc tgacgccgct gctgctgcgg ggcttgacag gctcggcccg gcggctccca    60
gtgccgcgcg ccaagatcca ttcgttg                                        87

<210> SEQ ID NO 11
<211> LENGTH: 33
<212> TYPE: PRT
<213> ORGANISM: Artificial Sequence
<220> FEATURE:
<223> OTHER INFORMATION: Organelle targeting sequence

<400> SEQUENCE: 11

Met Ser Ile Val Leu Ile Ile Val Ile Val Val Ile Phe Leu Ile Cys
1               5                   10                  15

Phe Leu Tyr Leu Ser Asn Ser Lys Asp Pro Arg Val Pro Val Glu Leu
            20                  25                  30

Met

<210> SEQ ID NO 12
<211> LENGTH: 96
<212> TYPE: DNA
<213> ORGANISM: Artificial sequence
<220> FEATURE:
<223> OTHER INFORMATION: Sequence encoding organelle targeting sequence

<400> SEQUENCE: 12
atgagcattg ttttaataat tgttatttgg attttttttaa tatgtttttt atatttaagc    60
aacagcaaag atcccagagt accagttgaa ttaatg                              96

<210> SEQ ID NO 13
<211> LENGTH: 82
<212> TYPE: PRT
<213> ORGANISM: Artificial Sequence
<220> FEATURE:
<223> OTHER INFORMATION: Organelle targeting sequence

<400> SEQUENCE: 13

Met Arg Leu Arg Glu Pro Leu Leu Ser Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Ser
        35                  40                  45

Arg Leu Pro Gln Leu Val Gly Val Ser Thr Pro Leu Gln Gly Gly Ser
    50                  55                  60

Asn Ser Ala Ala Ala Ile Gly Gln Ser Ser Gly Glu Leu Arg Thr Gly 65        70        75        80

Gly Ala

<210> SEQ ID NO 14
<211> LENGTH: 246
<212> TYPE: DNA
<213> ORGANISM: Artificial sequence
<220> FEATURE:
<223> OTHER INFORMATION: Sequence encoding organelle targeting sequence

<400> SEQUENCE: 14
atgaggcttc gggagccgct cctgagcggc agcgccgcga tgccaggcgc gtccctacag      60
cgggcctgcc gcctgctcgt ggccgtctgc gctctgcacc ttggcgtcac cctcgtttac     120
tacctggctg gccgcgacct gagccgcctg ccccaactgg tcggagtctc cacaccgctg     180
cagggcggct cgaacagtgc cgccgccatc gggcagtcct ccggggagct ccggaccgga     240
ggggcc                                                                246

<210> SEQ ID NO 15
<211> LENGTH: 50
<212> TYPE: PRT
<213> ORGANISM: Artificial sequence
<220> FEATURE:
<223> OTHER INFORMATION: Organelle targeting sequence

<400> SEQUENCE: 15

Glu Thr Ile Arg Pro Ile Arg Ile Arg Arg Cys Ser Tyr Phe Thr Ser
1               5                   10                  15

Thr Asp Ser Lys Met Ala Ile Gln Leu Arg Ser Pro Phe Pro Leu Ala
            20                  25                  30

Leu Pro Gly Met Leu Ala Leu Leu Gly Trp Trp Trp Phe Phe Ser Arg
        35                  40                  45

Lys Lys
    50

<210> SEQ ID NO 16
<211> LENGTH: 144
<212> TYPE: DNA
<213> ORGANISM: Artificial sequence
<220> FEATURE:
<223> OTHER INFORMATION: Sequence encoding organelle targeting sequence

<400> SEQUENCE: 16
gaaacaataa gacctataag aagatgtagt acatttacat ctacagacag caaaatggca      60
attcaattaa gatctcccct tccattagca ttaccaggaa tgttagcttt attaggatgg     120
tggtggtttt tcagtagaaa aaaa                                             144

<210> SEQ ID NO 17
<211> LENGTH: 13
<212> TYPE: PRT
<213> ORGANISM: Artificial sequence
<220> FEATURE:
<223> OTHER INFORMATION: Organelle targeting sequence

<400> SEQUENCE: 17

Ala Leu Gln Lys Lys Leu Glu Glu Leu Glu Leu Asp Glu
1               5                   10

<210> SEQ ID NO 18
<211> LENGTH: 39
<212> TYPE: DNA

<213> ORGANISM: Artificial sequence
<220> FEATURE:
<223> OTHER INFORMATION: Sequence encoding organelle targeting sequence

<400> SEQUENCE: 18
gccttgcaga agaagctgga ggagctagag cttgatgag                              39

<210> SEQ ID NO 19
<211> LENGTH: 566
<212> TYPE: PRT
<213> ORGANISM: Artificial sequence
<220> FEATURE:
<223> OTHER INFORMATION: Organelle targeting sequence

<400> SEQUENCE: 19

```
Ala Asp Leu Ser Leu Val Asp Ala Leu Thr Glu Pro Pro Glu Ile
1               5                   10                  15

Glu Gly Glu Ile Lys Arg Asp Phe Met Ala Ala Leu Glu Ala Glu Pro
            20                  25                  30

Tyr Asp Asp Ile Val Gly Glu Thr Val Glu Lys Thr Glu Phe Ile Pro
        35                  40                  45

Leu Leu Asp Gly Asp Glu Lys Thr Gly Asn Ser Glu Ser Lys Lys Lys
    50                  55                  60

Pro Cys Leu Asp Thr Ser Gln Val Gly Ile Pro Ser Ser Lys Pro
65                  70                  75                  80

Thr Leu Leu Ala Asn Gly Asp His Gly Met Glu Gly Asn Asn Thr Ala
                85                  90                  95

Gly Ser Pro Thr Asp Phe Leu Glu Glu Arg Val Asp Tyr Pro Asp Tyr
            100                 105                 110

Gln Ser Ser Gln Asn Trp Pro Glu Asp Ala Ser Phe Cys Phe Gln Pro
        115                 120                 125

Gln Gln Val Leu Asp Thr Asp Gln Ala Glu Pro Phe Asn Glu His Arg
    130                 135                 140

Asp Asp Gly Leu Ala Asp Leu Leu Phe Val Ser Ser Gly Pro Thr Asn
145                 150                 155                 160

Ala Ser Ala Phe Thr Glu Arg Asp Asn Pro Ser Glu Asp Ser Tyr Gly
                165                 170                 175

Met Leu Pro Cys Asp Ser Phe Ala Ser Thr Ala Val Val Ser Gln Glu
            180                 185                 190

Trp Ser Val Gly Ala Pro Asn Ser Pro Cys Ser Glu Ser Cys Val Ser
        195                 200                 205

Pro Glu Val Thr Ile Glu Thr Leu Gln Pro Ala Thr Glu Leu Ser Lys
    210                 215                 220

Ala Ala Glu Val Glu Ser Val Lys Glu Gln Leu Pro Ala Lys Ala Leu
225                 230                 235                 240

Glu Thr Met Ala Glu Gln Thr Thr Asp Val Val His Ser Pro Ser Thr
                245                 250                 255

Asp Thr Thr Pro Gly Pro Asp Thr Glu Ala Ala Leu Ala Lys Asp Ile
            260                 265                 270

Glu Glu Ile Thr Lys Pro Asp Val Ile Leu Ala Asn Val Thr Gln Pro
        275                 280                 285

Ser Thr Glu Ser Asp Met Phe Leu Ala Gln Asp Met Glu Leu Leu Thr
    290                 295                 300

Gly Thr Glu Ala Ala His Ala Asn Asn Ile Ile Leu Pro Thr Glu Pro
305                 310                 315                 320

Asp Glu Ser Ser Thr Lys Asp Val Ala Pro Pro Met Glu Glu Glu Ile
```

```
                    325                 330                 335
Val Pro Gly Asn Asp Thr Thr Ser Pro Lys Glu Thr Glu Thr Leu
                340                 345                 350
Pro Ile Lys Met Asp Leu Ala Pro Pro Glu Asp Val Leu Leu Thr Lys
            355                 360                 365
Glu Thr Glu Leu Ala Pro Ala Lys Gly Met Val Ser Leu Ser Glu Ile
        370                 375                 380
Glu Glu Ala Leu Ala Lys Asn Asp Val Arg Ser Ala Glu Ile Pro Val
385                 390                 395                 400
Ala Gln Glu Thr Val Ser Glu Thr Glu Val Val Leu Ala Thr Glu
                405                 410                 415
Val Val Leu Pro Ser Asp Pro Ile Thr Thr Leu Thr Lys Asp Val Thr
                420                 425                 430
Leu Pro Leu Glu Ala Glu Arg Pro Leu Val Thr Asp Met Thr Pro Ser
            435                 440                 445
Leu Glu Thr Glu Met Thr Leu Gly Lys Glu Thr Ala Pro Pro Thr Glu
    450                 455                 460
Thr Asn Leu Gly Met Ala Lys Asp Met Ser Pro Leu Pro Glu Ser Glu
465                 470                 475                 480
Val Thr Leu Gly Lys Asp Val Val Ile Leu Pro Glu Thr Lys Val Ala
                485                 490                 495
Glu Phe Asn Asn Val Thr Pro Leu Ser Glu Glu Val Thr Ser Val
                500                 505                 510
Lys Asp Met Ser Pro Ser Ala Glu Thr Glu Ala Pro Leu Ala Lys Asn
            515                 520                 525
Ala Asp Leu His Ser Gly Thr Glu Leu Ile Val Asp Asn Ser Met Ala
        530                 535                 540
Pro Ala Ser Asp Leu Ala Leu Pro Leu Glu Thr Lys Val Ala Thr Val
545                 550                 555                 560
Pro Ile Lys Asp Lys Gly
            565
```

<210> SEQ ID NO 20
<211> LENGTH: 1698
<212> TYPE: DNA
<213> ORGANISM: Artificial sequence
<220> FEATURE:
<223> OTHER INFORMATION: Sequence encoding organelle targeting sequence

<400> SEQUENCE: 20

```
gccgacctca gtcttgtgga tgcgttgaca gaaccacctc cagaaattga gggagaaata      60
aagcgagact tcatggctgc gctggaggca gagccctatg atgacatcgt gggagaaact     120
gtggagaaaa ctgagtttat tcctctcctg gatggtgatg agaaaaccgg gaactcagag     180
tccaaaaaga aaccctgctt agacactagc caggttgaag gtatcccatc ttctaaacca     240
acactcctag ccaatggtga tcatggaatg gaggggaata cactgcagg tctccaact      300
gacttccttg aagagagagt ggactatccg gattatcaga gcagccagaa ctggccagaa     360
gatgcaagct tttgtttcca gcctcagcaa gtgttagata ctgaccaggc tgagcccttt     420
aacgagcacc gtgatgatgg tttggcagat ctgctctttg tctccagtgg acccacgaac     480
gcttctgcat ttacagagcg agacaatcct tcagaagaca gttacggtat gcttccctgt     540
gactcatttg cttccacggc tgttgtatct caggagtggt ctgtgggagc cccaaactct     600
ccatgttcag agtcctgtgt ctccccagag gttactatag aaaccctaca gccagcaaca     660
```

-continued

```
gagctctcca aggcagcaga agtggaatca gtgaaagagc agctgccagc taaagcattg    720
gaaacgatgg cagagcagac cactgatgtg gtgcactctc catccacaga cacaacacca    780
ggcccagaca cagaggcagc actggctaaa gacatagaag agatcaccaa gccagatgtg    840
atattggcaa atgtcacgca gccatctact gaatcggata tgttcctggc ccaggacatg    900
gaactactca caggaacaga ggcagcccac gctaacaata tcatattgcc tacagaacca    960
gacgaatctt caaccaagga tgtagcacca cctatggaag aagaaattgt cccaggcaat   1020
gatacgacat cccccaaaga aacagagaca cacttccaa taaaaatgga cttggcacca    1080
cctgaggatg tgttacttac caaagaaaca gaactagccc cagccaaggg catggtttca   1140
ctctcagaaa tagaagaggc tctggcaaag aatgatgttc gctctgcaga ataccctgtg   1200
gctcaggaga cagtggtctc agaaacagag gtggtcctgg caacagaagt ggtactgccc   1260
tcagatccca taacaacatt gacaaaggat gtgacactcc ccttagaagc agagagaccg   1320
ttggtgacgg acatgactcc atctctggaa acagaaatga ccctaggcaa agagacagct   1380
ccacccacag aaacaaattt gggcatggcc aaagacatgt ctccactccc agaatcagaa   1440
gtgactctgg gcaaggacgt ggttatactt ccagaaacaa aggtggctga gtttaacaat   1500
gtgactccac tttcagaaga gaggtaacc tcagtcaagg acatgtctcc gtctgcagaa    1560
acagaggctc ccctggctaa gaatgctgat ctgcactcag gaacagagct gattgtggac   1620
aacagcatgg ctccagcctc cgatcttgca ctgcccttgg aaacaaaagt agcaacagtt   1680
ccaattaaag acaaagga                                                  1698
```

<210> SEQ ID NO 21
<211> LENGTH: 21
<212> TYPE: PRT
<213> ORGANISM: Artificial sequence
<220> FEATURE:
<223> OTHER INFORMATION: Organelle targeting domain

<400> SEQUENCE: 21

Met Trp Ala Ile Gly Ile Thr Val Leu Val Ile Phe Ile Ile Ile
1               5                   10                  15

Ile Val Trp Val Val
            20

<210> SEQ ID NO 22
<211> LENGTH: 63
<212> TYPE: DNA
<213> ORGANISM: Artificial Sequence
<220> FEATURE:
<223> OTHER INFORMATION: Sequence encoding organelle targeting sequence

<400> SEQUENCE: 22

```
atgtgggcaa tcgggattac tgttctggtt atcttcatca tcatcatcat cgtgtgggtt    60
gtc                                                                  63
```

<210> SEQ ID NO 23
<211> LENGTH: 20
<212> TYPE: PRT
<213> ORGANISM: Artificial sequence
<220> FEATURE:
<223> OTHER INFORMATION: Organelle targeting sequence

<400> SEQUENCE: 23

Met Trp Ala Ile Gly Ile Ser Val Leu Val Ile Ile Val Ile Ile Ile
1               5                   10                  15

Ile Val Trp Cys
            20

<210> SEQ ID NO 24
<211> LENGTH: 61
<212> TYPE: DNA
<213> ORGANISM: Artificial sequence
<220> FEATURE:
<223> OTHER INFORMATION: Sequence encoding organelle targeting sequence

<400> SEQUENCE: 24
atgtgggcga tagggatcag tgtcctggtg atcattgtca tcatcatcat cgtgtggtgt    60
g                                                                    61

<210> SEQ ID NO 25
<211> LENGTH: 15
<212> TYPE: PRT
<213> ORGANISM: Artificial sequence
<220> FEATURE:
<223> OTHER INFORMATION: Binding domain

<400> SEQUENCE: 25

Met Pro Lys Lys Lys Pro Thr Pro Ile Gln Leu Asn Pro Ala Pro
1               5                   10                  15

<210> SEQ ID NO 26
<211> LENGTH: 45
<212> TYPE: DNA
<213> ORGANISM: Artificial sequence
<220> FEATURE:
<223> OTHER INFORMATION: Sequence encoding binding domain

<400> SEQUENCE: 26
atgcccaaga agaagccgac gcccatccag ctgaacccgg ccccc                    45

<210> SEQ ID NO 27
<211> LENGTH: 16
<212> TYPE: PRT
<213> ORGANISM: Artificial sequence
<220> FEATURE:
<223> OTHER INFORMATION: Binding domain

<400> SEQUENCE: 27

Met Leu Ala Arg Arg Lys Pro Val Leu Pro Ala Leu Thr Ile Asn Pro
1               5                   10                  15

<210> SEQ ID NO 28
<211> LENGTH: 48
<212> TYPE: DNA
<213> ORGANISM: Artificial sequence
<220> FEATURE:
<223> OTHER INFORMATION: Sequence encoding binding domain

<400> SEQUENCE: 28
atgctggccc ggaggaagcc ggtgctgccg gcgctcacca tcaaccct                 48

<210> SEQ ID NO 29
<211> LENGTH: 17
<212> TYPE: PRT
<213> ORGANISM: Artificial sequence
<220> FEATURE:
<223> OTHER INFORMATION: Binding domain

<400> SEQUENCE: 29

Ser Ser Ile Leu Ala Gln Arg Arg Val Arg Lys Leu Pro Ser Thr Thr
1               5                   10                  15

Leu

<210> SEQ ID NO 30
<211> LENGTH: 51
<212> TYPE: DNA
<213> ORGANISM: Artificial sequence
<220> FEATURE:
<223> OTHER INFORMATION: Sequence encoding binding domain

<400> SEQUENCE: 30
tcatccatcc tggcccagcg gcgagtgagg aagttgccat ccaccaccct g        51

<210> SEQ ID NO 31
<211> LENGTH: 18
<212> TYPE: PRT
<213> ORGANISM: Artificial sequence
<220> FEATURE:
<223> OTHER INFORMATION: Binding domain

<400> SEQUENCE: 31

Arg Ser Thr Leu Ala Gln Arg Arg Gly Ile Lys Lys Ile Thr Ser Thr
1               5                   10                  15

Ala Leu

<210> SEQ ID NO 32
<211> LENGTH: 54
<212> TYPE: DNA
<213> ORGANISM: Artificial sequence
<220> FEATURE:
<223> OTHER INFORMATION: Sequence encoding binding domain

<400> SEQUENCE: 32
cgctctactc ttgctcagcg gagaggtatt aaaaaaatca cctcaacagc cctg        54

<210> SEQ ID NO 33
<211> LENGTH: 18
<212> TYPE: PRT
<213> ORGANISM: Artificial sequence
<220> FEATURE:
<223> OTHER INFORMATION: Binding domain

<400> SEQUENCE: 33

Ser Ser Asn Leu Ala Gln Arg Arg Gly Met Lys Arg Leu Thr Ser Thr
1               5                   10                  15

Arg Leu

<210> SEQ ID NO 34
<211> LENGTH: 54
<212> TYPE: DNA
<213> ORGANISM: Artificial sequence
<220> FEATURE:
<223> OTHER INFORMATION: Sequence encoding binding domain

<400> SEQUENCE: 34
tcatccaacc tggctcagcg cagaggcatg aagagactca cgtccacgcg gctg        54

<210> SEQ ID NO 35
<211> LENGTH: 18
<212> TYPE: PRT
<213> ORGANISM: Artificial sequence
<220> FEATURE:
<223> OTHER INFORMATION: Binding domain

<400> SEQUENCE: 35

```
Gln Ser Lys Leu Ala Gln Arg Arg Gln Arg Ala Ser Leu Ser Ala Ala
1               5                   10                  15
Pro Val
```

<210> SEQ ID NO 36
<211> LENGTH: 54
<212> TYPE: DNA
<213> ORGANISM: Artificial sequence
<220> FEATURE:
<223> OTHER INFORMATION: Sequence encoding binding domain

<400> SEQUENCE: 36

```
cagtccaagc tggcgcagcg gcggcaaagg gccagtctgt cctcggcccc agtg        54
```

<210> SEQ ID NO 37
<211> LENGTH: 16
<212> TYPE: PRT
<213> ORGANISM: Artificial sequence
<220> FEATURE:
<223> OTHER INFORMATION: Binding domain

<400> SEQUENCE: 37

```
Gly Met Lys Pro Asn Pro Leu Asn Leu Thr Ala Thr Ser Asn Phe Ser
1               5                   10                  15
```

<210> SEQ ID NO 38
<211> LENGTH: 48
<212> TYPE: DNA
<213> ORGANISM: Artificial sequence
<220> FEATURE:
<223> OTHER INFORMATION: Sequence encoding binding domain

<400> SEQUENCE: 38

```
ggaatgaagc cgaacccgct gaacctgaca gcaacctcga atttctcc              48
```

<210> SEQ ID NO 39
<211> LENGTH: 4
<212> TYPE: PRT
<213> ORGANISM: Artificial sequence
<220> FEATURE:
<223> OTHER INFORMATION: Binding domain

<400> SEQUENCE: 39

```
Phe Gln Phe Pro
1
```

<210> SEQ ID NO 40
<211> LENGTH: 12
<212> TYPE: DNA
<213> ORGANISM: Artificial sequence
<220> FEATURE:
<223> OTHER INFORMATION: Sequence encoding binding domain

<400> SEQUENCE: 40

```
ttccagtttc ca                                                     12
```

<210> SEQ ID NO 41
<211> LENGTH: 16
<212> TYPE: PRT
<213> ORGANISM: Artificial sequence
<220> FEATURE:
<223> OTHER INFORMATION: Binding domain

<400> SEQUENCE: 41

```
Pro Gly Ile Met Leu Arg Arg Leu Gln Lys Gly Asn Leu Pro Val Arg
1               5                   10                  15
```

```
<210> SEQ ID NO 42
<211> LENGTH: 48
<212> TYPE: DNA
<213> ORGANISM: Artificial sequence
<220> FEATURE:
<223> OTHER INFORMATION: Sequence encoding binding domain

<400> SEQUENCE: 42
ccgggcatca tgctgcggcg cctgcagaag ggtaacctgc cggtgcgc                    48

<210> SEQ ID NO 43
<211> LENGTH: 16
<212> TYPE: PRT
<213> ORGANISM: Artificial sequence
<220> FEATURE:
<223> OTHER INFORMATION: Binding domain

<400> SEQUENCE: 43

Pro Gly Leu Met Leu Arg Arg Leu Arg Lys Gly Asn Leu Pro Ile Arg
1               5                   10                  15

<210> SEQ ID NO 44
<211> LENGTH: 48
<212> TYPE: DNA
<213> ORGANISM: Artificial sequence
<220> FEATURE:
<223> OTHER INFORMATION: Sequence encoding binding domain

<400> SEQUENCE: 44
ccgggcctca tgttgcgccg cctgcgcaag ggcaacctgc ccatccgc                    48

<210> SEQ ID NO 45
<211> LENGTH: 17
<212> TYPE: PRT
<213> ORGANISM: Artificial sequence
<220> FEATURE:
<223> OTHER INFORMATION: Binding domain

<400> SEQUENCE: 45

Leu Pro Ala Leu Leu Leu Arg Arg Leu Arg Arg Gly Ser Leu Ser Val
1               5                   10                  15
Arg

<210> SEQ ID NO 46
<211> LENGTH: 51
<212> TYPE: DNA
<213> ORGANISM: Artificial sequence
<220> FEATURE:
<223> OTHER INFORMATION: Sequence encoding binding domain

<400> SEQUENCE: 46
ctgccggcgc tcctgctgcg ccgcctgcgg aggggcagcc tgtcggtgcg c                51

<210> SEQ ID NO 47
<211> LENGTH: 16
<212> TYPE: PRT
<213> ORGANISM: Artificial sequence
<220> FEATURE:
<223> OTHER INFORMATION: Binding domain

<400> SEQUENCE: 47

Leu Asn Ser Val Val Leu Arg Arg Ala Arg Gly Gly Ala Val Ser Ala
1               5                   10                  15
```

```
<210> SEQ ID NO 48
<211> LENGTH: 48
<212> TYPE: DNA
<213> ORGANISM: Artificial sequence
<220> FEATURE:
<223> OTHER INFORMATION: Sequence encoding binding domain

<400> SEQUENCE: 48
ctcaactcgg tggtgctgcg gcgggcccgg ggcggcgcgg tgtcggcg                    48

<210> SEQ ID NO 49
<211> LENGTH: 16
<212> TYPE: PRT
<213> ORGANISM: Artificial sequence
<220> FEATURE:
<223> OTHER INFORMATION: Binding domain

<400> SEQUENCE: 49

Gly Leu Gln Glu Arg Arg Gly Ser Asn Val Ser Leu Thr Leu Asp Met
1               5                   10                  15

<210> SEQ ID NO 50
<211> LENGTH: 49
<212> TYPE: DNA
<213> ORGANISM: Artificial sequence
<220> FEATURE:
<223> OTHER INFORMATION: Sequence encoding binding domain

<400> SEQUENCE: 50
gctctggcag cgggggtgt aggtgtgttg cactacactg aatggaata                    49

<210> SEQ ID NO 51
<211> LENGTH: 16
<212> TYPE: PRT
<213> ORGANISM: Artificial sequence
<220> FEATURE:
<223> OTHER INFORMATION: Binding domain

<400> SEQUENCE: 51

Arg Leu Gln Glu Arg Arg Gly Ser Asn Val Ala Leu Met Leu Asp Val
1               5                   10                  15

<210> SEQ ID NO 52
<211> LENGTH: 48
<212> TYPE: DNA
<213> ORGANISM: Artificial sequence
<220> FEATURE:
<223> OTHER INFORMATION: Sequence encoding binding domain

<400> SEQUENCE: 52
cgactgcagg agaggcgggg ctccaatgtg gctctgatgc tggacgtt                    48

<210> SEQ ID NO 53
<211> LENGTH: 16
<212> TYPE: PRT
<213> ORGANISM: Artificial sequence
<220> FEATURE:
<223> OTHER INFORMATION: Binding domain

<400> SEQUENCE: 53

Gly Leu Gln Glu Arg Arg Gly Ser Asn Val Ser Leu Thr Leu Asp Met
1               5                   10                  15

<210> SEQ ID NO 54
<211> LENGTH: 48
<212> TYPE: DNA
<213> ORGANISM: Artificial sequence
```

```
<220> FEATURE:
<223> OTHER INFORMATION: Sequence encoding binding domain

<400> SEQUENCE: 54
ggacttcaag agagaagagg gtccaacgta tctcttacat tggacatg          48

<210> SEQ ID NO 55
<211> LENGTH: 18
<212> TYPE: PRT
<213> ORGANISM: Artificial sequence
<220> FEATURE:
<223> OTHER INFORMATION: Binding domain

<400> SEQUENCE: 55

Asn Pro Leu Leu Leu Lys Arg Arg Lys Lys Ala Arg Ala Lys Glu Ala
1               5                   10                  15

Ala Ala

<210> SEQ ID NO 56
<211> LENGTH: 54
<212> TYPE: DNA
<213> ORGANISM: Artificial sequence
<220> FEATURE:
<223> OTHER INFORMATION: Sequence encoding binding domain

<400> SEQUENCE: 56
aaccctctgc tgctgaagag gcggaagaaa gctcgggccc tggaggctgc ggct        54

<210> SEQ ID NO 57
<211> LENGTH: 12
<212> TYPE: PRT
<213> ORGANISM: Artificial sequence
<220> FEATURE:
<223> OTHER INFORMATION: Binding domain

<400> SEQUENCE: 57

Lys Gly Lys Ser Lys Arg Lys Lys Asp Leu Arg Ile
1               5                   10

<210> SEQ ID NO 58
<211> LENGTH: 36
<212> TYPE: DNA
<213> ORGANISM: Artificial sequence
<220> FEATURE:
<223> OTHER INFORMATION: Sequence encoding binding domain

<400> SEQUENCE: 58
aaaggaaaat ccaagaggaa gaaggatcta cggata          36

<210> SEQ ID NO 59
<211> LENGTH: 13
<212> TYPE: PRT
<213> ORGANISM: Artificial sequence
<220> FEATURE:
<223> OTHER INFORMATION: Binding domain

<400> SEQUENCE: 59

Ser Lys Gly Lys Lys Arg Asn Pro Gly Leu Lys Ile Pro
1               5                   10

<210> SEQ ID NO 60
<211> LENGTH: 39
<212> TYPE: DNA
<213> ORGANISM: Artificial sequence
<220> FEATURE:
<223> OTHER INFORMATION: Sequence encoding binding domain
```

-continued

```
<400> SEQUENCE: 60
tcgaaaggca agaagcgaaa ccctggcctt aaaattcca                              39

<210> SEQ ID NO 61
<211> LENGTH: 18
<212> TYPE: PRT
<213> ORGANISM: Artificial sequence
<220> FEATURE:
<223> OTHER INFORMATION: Binding domain

<400> SEQUENCE: 61

Asn Arg Leu Leu Asn Lys Arg Arg Lys Lys Gln Ala Gly Ser Ser Ser
1               5                   10                  15

Ala Ser

<210> SEQ ID NO 62
<211> LENGTH: 54
<212> TYPE: DNA
<213> ORGANISM: Artificial sequence
<220> FEATURE:
<223> OTHER INFORMATION: Sequence encoding binding domain

<400> SEQUENCE: 62
aaccggctcc tcaacaagag gagaaaaaag caggcaggca gctcctctgc ctca            54

<210> SEQ ID NO 63
<211> LENGTH: 18
<212> TYPE: PRT
<213> ORGANISM: Artificial sequence
<220> FEATURE:
<223> OTHER INFORMATION: Binding domain

<400> SEQUENCE: 63

Asn Asn Pro Ile Leu Arg Lys Arg Lys Leu Leu Gly Thr Lys Pro Lys
1               5                   10                  15

Asp Ser

<210> SEQ ID NO 64
<211> LENGTH: 54
<212> TYPE: DNA
<213> ORGANISM: Artificial sequence
<220> FEATURE:
<223> OTHER INFORMATION: Sequence encoding binding domain

<400> SEQUENCE: 64
aacaacccca ttctgcggaa gaggaagtta cttggcacca agccaaagga cagt            54

<210> SEQ ID NO 65
<211> LENGTH: 18
<212> TYPE: PRT
<213> ORGANISM: Artificial sequence
<220> FEATURE:
<223> OTHER INFORMATION: Binding domain

<400> SEQUENCE: 65

Asn Ala Pro Leu Ala Lys Arg Arg Lys Gln Lys Leu Arg Ser Ala Thr
1               5                   10                  15

Ala Ser

<210> SEQ ID NO 66
<211> LENGTH: 54
<212> TYPE: DNA
<213> ORGANISM: Artificial sequence
```

```
<220> FEATURE:
<223> OTHER INFORMATION: Sequence encoding binding domain

<400> SEQUENCE: 66
aatgcacccc tggccaagcg gcggaagcag aagctgcgga gcgccaccgc ctcc       54

<210> SEQ ID NO 67
<211> LENGTH: 10
<212> TYPE: PRT
<213> ORGANISM: Artificial sequence
<220> FEATURE:
<223> OTHER INFORMATION: Binding domain

<400> SEQUENCE: 67

Asn Arg Lys Pro Asp Leu Arg Val Leu Ile
1               5                   10

<210> SEQ ID NO 68
<211> LENGTH: 30
<212> TYPE: DNA
<213> ORGANISM: Artificial sequence
<220> FEATURE:
<223> OTHER INFORMATION: Sequence encoding binding domain

<400> SEQUENCE: 68
aaccgtaaac cagatctccg agttcttatt                                  30

<210> SEQ ID NO 69
<211> LENGTH: 11
<212> TYPE: PRT
<213> ORGANISM: Artificial sequence
<220> FEATURE:
<223> OTHER INFORMATION: Binding domain

<400> SEQUENCE: 69

Asn Ser Arg Lys Pro Asp Leu Arg Val Val Ile
1               5                   10

<210> SEQ ID NO 70
<211> LENGTH: 33
<212> TYPE: DNA
<213> ORGANISM: Artificial sequence
<220> FEATURE:
<223> OTHER INFORMATION: Sequence encoding binding domain

<400> SEQUENCE: 70
aacagtagga aaccagatct tcgagttgtc atc                              33

<210> SEQ ID NO 71
<211> LENGTH: 14
<212> TYPE: PRT
<213> ORGANISM: Artificial sequence
<220> FEATURE:
<223> OTHER INFORMATION: Binding domain

<400> SEQUENCE: 71

Glu Ala Arg Arg Arg Ile Asp Leu Asn Leu Asp Ile Ser Pro
1               5                   10

<210> SEQ ID NO 72
<211> LENGTH: 42
<212> TYPE: DNA
<213> ORGANISM: Artificial sequence
<220> FEATURE:
<223> OTHER INFORMATION: Sequence encoding binding domain

<400> SEQUENCE: 72
```
gaggcccggc ggaggatcga cctcaacctg gatatcagcc cc    42

<210> SEQ ID NO 73
<211> LENGTH: 17
<212> TYPE: PRT
<213> ORGANISM: Artificial sequence
<220> FEATURE:
<223> OTHER INFORMATION: Binding domain

<400> SEQUENCE: 73

Ile Leu Lys Gln Ser Met Thr Leu Asn Leu Ala Asp Pro Val Gly Ser
1               5                   10                  15

Leu

<210> SEQ ID NO 74
<211> LENGTH: 51
<212> TYPE: DNA
<213> ORGANISM: Artificial sequence
<220> FEATURE:
<223> OTHER INFORMATION: Sequence encoding binding domain

<400> SEQUENCE: 74
atcctgaaac agagcatgac cctgaacctg gccgacccag tggggagcct g    51

<210> SEQ ID NO 75
<211> LENGTH: 17
<212> TYPE: PRT
<213> ORGANISM: Artificial sequence
<220> FEATURE:
<223> OTHER INFORMATION: Binding domain

<400> SEQUENCE: 75

Leu Leu Lys Pro Ser Leu Ala Val Asn Leu Ala Asp Pro Tyr Arg Ser
1               5                   10                  15

Leu

<210> SEQ ID NO 76
<211> LENGTH: 51
<212> TYPE: DNA
<213> ORGANISM: Artificial sequence
<220> FEATURE:
<223> OTHER INFORMATION: Sequence encoding binding domain

<400> SEQUENCE: 76
ctcctgaaac cgagcctggc ggtcaacctg gccgacccct accggagtct c    51

<210> SEQ ID NO 77
<211> LENGTH: 18
<212> TYPE: PRT
<213> ORGANISM: Artificial sequence
<220> FEATURE:
<223> OTHER INFORMATION: Binding domain

<400> SEQUENCE: 77

Leu Glu Arg Pro Ser Arg Asp His Leu Tyr Leu Pro Leu Glu Pro Ser
1               5                   10                  15

Tyr Arg

<210> SEQ ID NO 78
<211> LENGTH: 54
<212> TYPE: DNA
<213> ORGANISM: Artificial sequence
<220> FEATURE:
<223> OTHER INFORMATION: Sequence encoding binding domain

```
<400> SEQUENCE: 78
ttggaaaggc cttctagaga tcatctctat cttcctcttg agccatccta ccgg         54

<210> SEQ ID NO 79
<211> LENGTH: 17
<212> TYPE: PRT
<213> ORGANISM: Artificial sequence
<220> FEATURE:
<223> OTHER INFORMATION: Binding domain

<400> SEQUENCE: 79

Val His Lys His Lys His Glu Met Thr Leu Lys Phe Gly Pro Ala Arg
1               5                   10                  15
Thr

<210> SEQ ID NO 80
<211> LENGTH: 51
<212> TYPE: DNA
<213> ORGANISM: Artificial sequence
<220> FEATURE:
<223> OTHER INFORMATION: Sequence encoding binding domain

<400> SEQUENCE: 80
gttcataaac acaagcatga gatgacattg aaatttggcc cagcccgaac t           51

<210> SEQ ID NO 81
<211> LENGTH: 18
<212> TYPE: PRT
<213> ORGANISM: Artificial sequence
<220> FEATURE:
<223> OTHER INFORMATION: Binding domain

<400> SEQUENCE: 81

Lys Ser Arg Leu Ala Arg Arg Arg Ala Leu Ala Gln Ala Gly Arg Gly
1               5                   10                  15
Glu Asp

<210> SEQ ID NO 82
<211> LENGTH: 54
<212> TYPE: DNA
<213> ORGANISM: Artificial sequence
<220> FEATURE:
<223> OTHER INFORMATION: Sequence encoding binding domain

<400> SEQUENCE: 82
aagtcacgcc tggcccggag acgggccctg gcccaggcag gccgtggtga agac         54

<210> SEQ ID NO 83
<211> LENGTH: 18
<212> TYPE: PRT
<213> ORGANISM: Artificial sequence
<220> FEATURE:
<223> OTHER INFORMATION: Binding domain

<400> SEQUENCE: 83

Lys Ala Pro Leu Ala Lys Arg Arg Lys Met Lys Lys Thr Ser Thr Ser
1               5                   10                  15
Thr Glu

<210> SEQ ID NO 84
<211> LENGTH: 54
<212> TYPE: DNA
<213> ORGANISM: Artificial sequence
```

```
<220> FEATURE:
<223> OTHER INFORMATION: Sequence encoding binding domain

<400> SEQUENCE: 84
aaggcccctt tggctaagag aagaaaaatg aaaaagacta gcaccagtac cgag         54

<210> SEQ ID NO 85
<211> LENGTH: 16
<212> TYPE: PRT
<213> ORGANISM: Artificial sequence
<220> FEATURE:
<223> OTHER INFORMATION: Binding domain

<400> SEQUENCE: 85

Arg Ser Lys Lys Pro Lys Gly Leu Gly Leu Ala Pro Thr Leu Val Ile
1               5                   10                  15

<210> SEQ ID NO 86
<211> LENGTH: 48
<212> TYPE: DNA
<213> ORGANISM: Artificial sequence
<220> FEATURE:
<223> OTHER INFORMATION: Sequence encoding binding domain

<400> SEQUENCE: 86
agatccaaga aacccaaagg gttaggactg gcacccaccc ttgtgatc               48

<210> SEQ ID NO 87
<211> LENGTH: 17
<212> TYPE: PRT
<213> ORGANISM: Artificial sequence
<220> FEATURE:
<223> OTHER INFORMATION: Binding domain

<400> SEQUENCE: 87

Lys Ala Lys Lys Pro Lys Gly Leu Glu Ile Ser Ala Pro Pro Leu Val
1               5                   10                  15
Leu

<210> SEQ ID NO 88
<211> LENGTH: 51
<212> TYPE: DNA
<213> ORGANISM: Artificial sequence
<220> FEATURE:
<223> OTHER INFORMATION: Sequence encoding binding domain

<400> SEQUENCE: 88
aaggccaaaa aacccaaagg cttggaaatc tcagcgcccc cgctggtgct c           51

<210> SEQ ID NO 89
<211> LENGTH: 11
<212> TYPE: PRT
<213> ORGANISM: Artificial sequence
<220> FEATURE:
<223> OTHER INFORMATION: Binding domain

<400> SEQUENCE: 89

Gln Gly Lys Arg Lys Ala Leu Lys Leu Asn Phe
1               5                   10

<210> SEQ ID NO 90
<211> LENGTH: 33
<212> TYPE: DNA
<213> ORGANISM: Artificial sequence
<220> FEATURE:
<223> OTHER INFORMATION: Sequence encoding binding domain
```

```
<400> SEQUENCE: 90
cagggtaaac gcaaagcact gaagttgaat ttt                              33

<210> SEQ ID NO 91
<211> LENGTH: 17
<212> TYPE: PRT
<213> ORGANISM: Artificial sequence
<220> FEATURE:
<223> OTHER INFORMATION: Binding domain

<400> SEQUENCE: 91

Val His Lys His Lys His Glu Met Thr Leu Lys Phe Gly Pro Ala Arg
1               5                   10                  15

Asn

<210> SEQ ID NO 92
<211> LENGTH: 51
<212> TYPE: DNA
<213> ORGANISM: Artificial sequence
<220> FEATURE:
<223> OTHER INFORMATION: Sequence encoding binding domain

<400> SEQUENCE: 92
gtccataaac ataaacatga gatgacactg aaatttggtc cagcacgtaa t           51

<210> SEQ ID NO 93
<211> LENGTH: 15
<212> TYPE: PRT
<213> ORGANISM: Artificial sequence
<220> FEATURE:
<223> OTHER INFORMATION: Binding domain

<400> SEQUENCE: 93

Ser Lys Leu Val Lys Arg Arg Leu Gln Gln Gly Lys Val Thr Ile
1               5                   10                  15

<210> SEQ ID NO 94
<211> LENGTH: 45
<212> TYPE: DNA
<213> ORGANISM: Artificial sequence
<220> FEATURE:
<223> OTHER INFORMATION: Sequence encoding binding domain

<400> SEQUENCE: 94
agtaaattag ttaagagaag attacaacaa ggcaaagtta ctatt                 45

<210> SEQ ID NO 95
<211> LENGTH: 17
<212> TYPE: PRT
<213> ORGANISM: Artificial sequence
<220> FEATURE:
<223> OTHER INFORMATION: Binding domain

<400> SEQUENCE: 95

Cys Ala Asp Lys Ile Ser Arg Arg Arg Leu Gln Gln Gly Lys Ile Thr
1               5                   10                  15

Val

<210> SEQ ID NO 96
<211> LENGTH: 51
<212> TYPE: DNA
<213> ORGANISM: Artificial sequence
<220> FEATURE:
<223> OTHER INFORMATION: Sequence encoding binding domain
```

<400> SEQUENCE: 96
tgtgccgata agatcagccg gcggagactg cagcagggca agatcactgt c    51

<210> SEQ ID NO 97
<211> LENGTH: 17
<212> TYPE: PRT
<213> ORGANISM: Artificial sequence
<220> FEATURE:
<223> OTHER INFORMATION: Binding domain

<400> SEQUENCE: 97

Lys Gly Arg Lys Pro Arg Asp Leu Glu Leu Pro Leu Ser Pro Ser Leu
1               5                   10                  15
Leu

<210> SEQ ID NO 98
<211> LENGTH: 51
<212> TYPE: DNA
<213> ORGANISM: Artificial sequence
<220> FEATURE:
<223> OTHER INFORMATION: Sequence encoding binding domain

<400> SEQUENCE: 98
aagggccgga agccccggga cctagagctt ccactcagcc cgagcctgct a    51

<210> SEQ ID NO 99
<211> LENGTH: 14
<212> TYPE: PRT
<213> ORGANISM: Artificial sequence
<220> FEATURE:
<223> OTHER INFORMATION: Binding domain

<400> SEQUENCE: 99

Arg Phe Ser Thr Ile Val Arg Arg Arg Ala Lys Gly Ala Met
1               5                   10

<210> SEQ ID NO 100
<211> LENGTH: 42
<212> TYPE: DNA
<213> ORGANISM: Artificial sequence
<220> FEATURE:
<223> OTHER INFORMATION: Sequence encoding binding domain

<400> SEQUENCE: 100
cgcttcagca ccatcgtgcg gcgccgggcc aagggcgcca tg    42

<210> SEQ ID NO 101
<211> LENGTH: 17
<212> TYPE: PRT
<213> ORGANISM: Artificial sequence
<220> FEATURE:
<223> OTHER INFORMATION: Binding domain

<400> SEQUENCE: 101

Arg Cys Asn Thr Ile Val Arg Arg Arg Ala Lys Gly Ser Val Ser Leu
1               5                   10                  15
Glu

<210> SEQ ID NO 102
<211> LENGTH: 51
<212> TYPE: DNA
<213> ORGANISM: Artificial sequence
<220> FEATURE:
<223> OTHER INFORMATION: Sequence encoding binding domain

<400> SEQUENCE: 102
cgctgtaaca ccatcgtgcg gcggcgggct aagggctccg tgagcctgga g        51

<210> SEQ ID NO 103
<211> LENGTH: 14
<212> TYPE: PRT
<213> ORGANISM: Artificial sequence
<220> FEATURE:
<223> OTHER INFORMATION: Binding domain

<400> SEQUENCE: 103

Pro Trp Asn Ala Leu Leu Arg Arg Arg Ala Arg Gly Pro Pro
1               5                   10

<210> SEQ ID NO 104
<211> LENGTH: 42
<212> TYPE: DNA
<213> ORGANISM: Artificial sequence
<220> FEATURE:
<223> OTHER INFORMATION: Sequence encoding binding domain

<400> SEQUENCE: 104
ccttggaacg cgctgctgcg gcgccgcgcg cgcggccctc ct                  42

<210> SEQ ID NO 105
<211> LENGTH: 58
<212> TYPE: PRT
<213> ORGANISM: Artificial sequence
<220> FEATURE:
<223> OTHER INFORMATION: Binding domain

<400> SEQUENCE: 105

Ile Ala Glu Ser Glu Asp Ser Gln Glu Ser Val Asp Ser Val Thr Asp
1               5                   10                  15

Ser Gln Lys Arg Arg Glu Ile Leu Ser Arg Arg Pro Ser Tyr Arg Lys
                20                  25                  30

Ile Leu Asn Asp Leu Ser Ser Asp Ala Pro Gly Val Pro Arg Ile Glu
            35                  40                  45

Glu Glu Lys Ser Glu Glu Glu Thr Ser Ala
        50                  55

<210> SEQ ID NO 106
<211> LENGTH: 174
<212> TYPE: DNA
<213> ORGANISM: Artificial sequence
<220> FEATURE:
<223> OTHER INFORMATION: Sequence encoding binding domain

<400> SEQUENCE: 106
attgcagaaa gtgaagattc acaggagtca gtggatagtg taactgattc ccaaaagcga    60
agggaaattc tttcaaggag gccttcctac aggaaaattt tgaatgactt atcttctgat   120
gcaccaggag tgccaaggat tgaagaagag aagtctgaag aggagacttc agca         174

<210> SEQ ID NO 107
<211> LENGTH: 58
<212> TYPE: PRT
<213> ORGANISM: Artificial sequence
<220> FEATURE:
<223> OTHER INFORMATION: Binding domain

<400> SEQUENCE: 107

Leu Ser Glu Ser Glu Glu Ser Gln Asp Ser Ser Asp Ser Ile Gly Ser

```
                1               5              10              15
Ser Gln Gln Ala His Gly Ile Leu Ala Arg Arg Pro Ser Tyr Arg Lys
                        20              25              30

Ile Leu Lys Asp Leu Ser Ser Glu Asp Thr Arg Gly Arg Lys Gly Asp
            35              40              45

Gly Glu Asn Ser Gly Val Ser Ala Ala Val
        50              55

<210> SEQ ID NO 108
<211> LENGTH: 174
<212> TYPE: DNA
<213> ORGANISM: Artificial sequence
<220> FEATURE:
<223> OTHER INFORMATION: Sequence encoding binding domain

<400> SEQUENCE: 108
ttatcagaaa gtgaggagtc ccaggactca tccgacagca taggctcctc acagaaagcc      60
cacgggatcc tagcacggcg cccatcttac agaaaaattt tgaaagactt atcttctgaa     120
gatacacggg gcagaaaagg agacggagaa aattctggag tttctgctgc tgtc            174

<210> SEQ ID NO 109
<211> LENGTH: 57
<212> TYPE: PRT
<213> ORGANISM: Artificial sequence
<220> FEATURE:
<223> OTHER INFORMATION: Binding domain

<400> SEQUENCE: 109

Ile Ala Glu Thr Asp Asp Ser Ala Asp Ser Glu Val Ile Asp Ser His
1               5                   10                  15

Lys Arg Arg Glu Ile Leu Ser Ser Arg Arg Pro Ser Tyr Arg Lys Ile
                20                  25                  30

Leu Asn Glu Leu Ser Ser Asp Val Pro Gly Ile Pro Lys Ile Glu Glu
            35                  40                  45

Glu Lys Ser Glu Glu Glu Gly Thr Pro
        50                  55

<210> SEQ ID NO 110
<211> LENGTH: 171
<212> TYPE: DNA
<213> ORGANISM: Artificial sequence
<220> FEATURE:
<223> OTHER INFORMATION: Sequence encoding binding domain

<400> SEQUENCE: 110
attgcagaga cagatgaatc tgcagaatca gaaggtgtaa ttgattctca taaacgtaga      60
gaaatccttt cacgaagacc ctcttatagg aaaatactga atgaactgtc ctctgatgtg     120
cctggtgttc ccaagattga agaagagaga tcagaggaag aaggaacacc a               171

<210> SEQ ID NO 111
<211> LENGTH: 4
<212> TYPE: PRT
<213> ORGANISM: Artificial sequence
<220> FEATURE:
<223> OTHER INFORMATION: Binding domain

<400> SEQUENCE: 111

Phe Lys Thr Phe
1
```

```
<210> SEQ ID NO 112
<211> LENGTH: 12
<212> TYPE: DNA
<213> ORGANISM: Artificial sequence
<220> FEATURE:
<223> OTHER INFORMATION: Sequence encoding binding domain

<400> SEQUENCE: 112
tttaaaactt tc                                                              12

<210> SEQ ID NO 113
<211> LENGTH: 4
<212> TYPE: PRT
<213> ORGANISM: Artificial sequence
<220> FEATURE:
<223> OTHER INFORMATION: Binding domain

<400> SEQUENCE: 113

Cys Arg Pro Leu
1

<210> SEQ ID NO 114
<211> LENGTH: 12
<212> TYPE: DNA
<213> ORGANISM: Artificial sequence
<220> FEATURE:
<223> OTHER INFORMATION: Sequence encoding binding domain

<400> SEQUENCE: 114
tgtcgtcctt ta                                                              12

<210> SEQ ID NO 115
<211> LENGTH: 4
<212> TYPE: PRT
<213> ORGANISM: Artificial sequence
<220> FEATURE:
<223> OTHER INFORMATION: Binding domain

<400> SEQUENCE: 115

Pro Pro Arg Pro
1

<210> SEQ ID NO 116
<211> LENGTH: 12
<212> TYPE: DNA
<213> ORGANISM: Artificial sequence
<220> FEATURE:
<223> OTHER INFORMATION: Sequence endoding binding domain

<400> SEQUENCE: 116
cctccccgcc ct                                                              12

<210> SEQ ID NO 117
<211> LENGTH: 184
<212> TYPE: PRT
<213> ORGANISM: Artificial sequence
<220> FEATURE:
<223> OTHER INFORMATION: Binding domain

<400> SEQUENCE: 117

Gln Gln Ala Leu Asn Glu Ser Ser Ala Lys Asn Gly Ala Ala Ser Lys
1               5                   10                  15

Arg Ala Phe Lys Gln Ser Pro Pro Ala Val Pro Ala Leu Gly Ala Gly
            20                  25                  30

Val Lys Lys Arg Arg His Gly Asp Glu Asp Thr Tyr Tyr Leu Gln Val
        35                  40                  45
```

```
Arg Gly Arg Glu Asn Phe Glu Ile Leu Met Lys Leu Lys Glu Ser Leu
 50                  55                  60
Glu Leu Met Glu Leu Val Pro Gln Pro Leu Val Asp Ser Tyr Arg Gln
 65                  70                  75                  80
Gln Gln Gln Leu Leu Gln Arg Pro Ser His Leu Gln Pro Pro Ser Tyr
                 85                  90                  95
Gly Pro Val Leu Ser Pro Met Asn Lys Val His Gly Met Asn Lys
            100                 105                 110
Leu Pro Ser Val Asn Gln Leu Val Gly Gln Pro Pro His Ser Ser
        115                 120                 125
Ala Ala Thr Pro Asn Leu Gly Pro Val Gly Pro Gly Met Leu Asn Asn
130                 135                 140
His Gly His Ala Val Pro Ala Asn Gly Glu Met Ser Ser Ser His Ser
145                 150                 155                 160
Ala Gln Ser Met Val Ser Gly Ser His Cys Thr Pro Pro Pro Tyr
                165                 170                 175
His Ala Asp Pro Ser Leu Val Ser
            180
```

<210> SEQ ID NO 118
<211> LENGTH: 552
<212> TYPE: DNA
<213> ORGANISM: Artificial sequence
<220> FEATURE:
<223> OTHER INFORMATION: Sequence endoding binding domain

<400> SEQUENCE: 118

```
cagcaggccc tgaacgagag ctccgccaag aacggggccg ccagcaagcg tgccttcaag     60
cagagccccc ctgccgtccc cgcccttggt gccggtgtga agaagcggcg gcatggagac    120
gaggacacgt actaccttca ggtgcgaggc cgggagaact ttgagatcct gatgaagctg    180
aaagagagcc tggagctgat ggagttggtg ccgcagccac tggtggactc ctatcggcag    240
cagcagcagc tcctacagag gccgagtcac ctacagcccc cgtcctacgg gccggtcctc    300
tcgcccatga acaaggtgca cggggggcatg aacaagctgc cctccgtcaa ccagctggtg    360
ggccagcctc ccccgcacag ttcggcagct cacccaacc tggggcccgt gggccccggg    420
atgctcaaca accatggcca cgcagtgcca gccaacggcg agatgagcag cagccacagc    480
gcccagtcca tggtctcggg gtcccactgc actccgccac cccctacca cgccgacccc    540
agcctcgtca gt                                                       552
```

<210> SEQ ID NO 119
<211> LENGTH: 10
<212> TYPE: PRT
<213> ORGANISM: Artificial sequence
<220> FEATURE:
<223> OTHER INFORMATION: Binding domain
<220> FEATURE:
<221> NAME/KEY: MISC_FEATURE
<222> LOCATION: (4)..(4)
<223> OTHER INFORMATION: X is a hydrophobic residue
<220> FEATURE:
<221> NAME/KEY: MISC_FEATURE
<222> LOCATION: (9)..(9)
<223> OTHER INFORMATION: X is a hydrophobic residue

<400> SEQUENCE: 119

```
Pro Pro Pro Xaa Pro Pro Pro Pro Xaa Pro
1                5                  10
```

<210> SEQ ID NO 120
<211> LENGTH: 6
<212> TYPE: PRT
<213> ORGANISM: Artificial Sequence
<220> FEATURE:
<223> OTHER INFORMATION: Binding domain
<220> FEATURE:
<221> NAME/KEY: MISC_FEATURE
<222> LOCATION: (1)..(1)
<223> OTHER INFORMATION: X is either R or P
<220> FEATURE:
<221> NAME/KEY: MISC_FEATURE
<222> LOCATION: (2)..(2)
<223> OTHER INFORMATION: X is either L or V
<220> FEATURE:
<221> NAME/KEY: MISC_FEATURE
<222> LOCATION: (5)..(5)
<223> OTHER INFORMATION: X is either L or R

<400> SEQUENCE: 120

Xaa Xaa Pro Pro Xaa Pro
1               5

<210> SEQ ID NO 121
<211> LENGTH: 18
<212> TYPE: DNA
<213> ORGANISM: Artificial sequence
<220> FEATURE:
<223> OTHER INFORMATION: Sequence encoding binding domain
<220> FEATURE:
<221> NAME/KEY: misc_feature
<222> LOCATION: (1)..(3)
<223> OTHER INFORMATION: nnn is aga or cct
<220> FEATURE:
<221> NAME/KEY: misc_feature
<222> LOCATION: (4)..(6)
<223> OTHER INFORMATION: nnn is ctt or gtt
<220> FEATURE:
<221> NAME/KEY: misc_feature
<222> LOCATION: (13)..(15)
<223> OTHER INFORMATION: nnn is tta or aga

<400> SEQUENCE: 121
nnnnnncctc ccnnncca                                                 18

<210> SEQ ID NO 122
<211> LENGTH: 255
<212> TYPE: PRT
<213> ORGANISM: Artificial sequence
<220> FEATURE:
<223> OTHER INFORMATION: Binding domain

<400> SEQUENCE: 122

Ala Leu Gly Thr Pro Ala Ala Glu Pro Val Thr Pro Thr Ser Lys
1               5                   10                  15

Ala Gly Ser Gly Ala Pro Gly Gly Thr Ser Lys Gly Pro Ala Glu Glu
                20                  25                  30

Ser Arg Val Arg Arg His Lys His Ser Ser Glu Ser Pro Gly Arg Asp
            35                  40                  45

Lys Gly Lys Leu Ser Arg Leu Lys Pro Ala Pro Pro Pro Pro Pro Ala
        50                  55                  60

Ala Ser Ala Gly Lys Ala Gly Lys Pro Ser Gln Ser Pro Ser Gln
65                  70                  75                  80

Glu Ala Ala Gly Glu Ala Val Leu Gly Ala Lys Thr Lys Ala Thr Ser
                85                  90                  95

Leu Val Asp Ala Val Asn Ser Asp Ala Ala Lys Pro Ser Gln Pro Gly
                100                 105                 110

Glu Gly Leu Lys Lys Pro Val Leu Pro Ala Thr Pro Lys Pro Gln Ser
            115                 120                 125

Ala Lys Pro Ser Gly Thr Pro Ile Ser Pro Ala Pro Val Pro Ser Thr
130                 135                 140

Leu Pro Ser Ala Ser Ala Leu Ala Gly Asp Gln Pro Ser Ser Thr
145                 150                 155                 160

Ala Phe Ile Pro Leu Ile Ser Thr Arg Val Ser Leu Arg Lys Thr Arg
                165                 170                 175

Gln Pro Pro Glu Arg Ile Ala Ser Gly Ala Ile Thr Lys Gly Val Val
            180                 185                 190

Leu Asp Ser Thr Glu Ala Leu Cys Leu Ala Ile Ser Arg Asn Ser Glu
195                 200                 205

Gln Met Ala Ser His Ser Ala Val Leu Glu Ala Gly Lys Asn Leu Tyr
            210                 215                 220

Thr Phe Cys Val Ser Tyr Val Asp Ser Ile Gln Gln Met Arg Asn Lys
225                 230                 235                 240

Phe Ala Phe Arg Glu Ala Ile Asn Lys Leu Glu Asn Asn Leu Arg
                245                 250                 255

<210> SEQ ID NO 123
<211> LENGTH: 765
<212> TYPE: DNA
<213> ORGANISM: Artificial sequence
<220> FEATURE:
<223> OTHER INFORMATION: Sequence encoding binding domain

<400> SEQUENCE: 123
gccttaggga cccctgctgc agctgagcca gtgaccccca ccagcaaagc aggctcaggt    60
gcaccagggg gcaccagcaa gggccccgcc gaggagtcca gagtgaggag gcacaagcac   120
tcctctgagt cgccagggag ggacaagggg aaattgtcca ggctcaaacc tgccccgccg   180
cccccaccag cagcctctgc agggaaggct ggaggaaagc cctcgcagag cccgagccag   240
gaggcggccg gggaggcagt cctgggcgca agacaaaag ccacgagtct ggttgatgct   300
gtgaacagtg acgctgccaa gcccagccag ccgggagagg gcctcaaaaa gcccgtgctc   360
ccggccactc caaagccaca gtccgccaag ccgtcgggga ccccatcag cccagccccc   420 gttccctcca cgttgccatc agcatcctcg gccctggcag gggaccagcc gtcttccacc   480
gccttcatcc ctctcatatc aacccgagtg tctcttcgga aaacccgcca gcctccagag   540
cggatcgcca gcggcgccat caccaagggc gtggtcctgg acagcaccga ggcgctgtgc   600
ctcgccatct ctaggaactc cgagcagatg ccagccaca gcgcagtgct ggaggccggc   660
aaaaacctct acacgttctg cgtgagctat gtggattcca tccagcaaat gaggaacaag   720
tttgccttcc gagaggccat caacaaactg agaataatc tccgg                   765

<210> SEQ ID NO 124
<211> LENGTH: 46
<212> TYPE: PRT
<213> ORGANISM: Artificial sequence
<220> FEATURE:
<223> OTHER INFORMATION: Binding domain

<400> SEQUENCE: 124

Glu Ser Lys Tyr Val Ser Leu Ile Thr Ser Tyr Gln Pro Phe Ser Leu
1               5                   10                  15

Glu Lys Glu Val Val Cys Glu Glu Pro Leu Ser Pro Ala Thr Val Pro
            20                  25                  30

Gly Met His Thr Glu Asp Asn Pro Gly Lys Val Glu His Thr
         35                  40                  45

<210> SEQ ID NO 125
<211> LENGTH: 138
<212> TYPE: DNA
<213> ORGANISM: Artificial sequence
<220> FEATURE:
<223> OTHER INFORMATION: Sequence encoding binding domain

<400> SEQUENCE: 125
gaatcaaaat atgtatcact catcacgtca taccagccat tttccttaga aaaggaggtg    60
gtctgtgaag agccgttgtc tccagcaaca gttccaggca tgcataccga agacaatcca   120
ggaaaagtgg aacataca                                                 138

<210> SEQ ID NO 126
<211> LENGTH: 6
<212> TYPE: PRT
<213> ORGANISM: Artificial sequence
<220> FEATURE:
<223> OTHER INFORMATION: Binding domain

<400> SEQUENCE: 126

Pro Ala Thr Pro Glu Pro
1               5

<210> SEQ ID NO 127
<211> LENGTH: 18
<212> TYPE: DNA
<213> ORGANISM: Artificial sequence
<220> FEATURE:
<223> OTHER INFORMATION: Sequence encoding binding domain

<400> SEQUENCE: 127
cccgccactc ctgaaccc                                                  18

<210> SEQ ID NO 128
<211> LENGTH: 4
<212> TYPE: PRT
<213> ORGANISM: Artificial sequence
<220> FEATURE:
<223> OTHER INFORMATION: Binding domain

<400> SEQUENCE: 128

Tyr Ile Pro Pro
1

<210> SEQ ID NO 129
<211> LENGTH: 12
<212> TYPE: DNA
<213> ORGANISM: Artificial sequence
<220> FEATURE:
<223> OTHER INFORMATION: Sequence encoding binding domain

<400> SEQUENCE: 129
tatattcccc ca                                                        12

<210> SEQ ID NO 130
<211> LENGTH: 393
<212> TYPE: PRT
<213> ORGANISM: Artificial sequence
<220> FEATURE:
<223> OTHER INFORMATION: Binding domain

<400> SEQUENCE: 130

```
Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
            35                  40                  45

Lys Ser Glu Ala Asp Tyr Leu Thr Phe Pro Ser Gly Glu Tyr Val Ala
50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
            115                 120                 125

Asn Arg Ala Tyr Arg His Gly Ile Ser Arg Gly Ala Glu Ala Pro Leu
130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
            195                 200                 205

Phe Leu Pro Lys Cys Ile Arg Ala Lys Ile Gln Asp Tyr His Ile Leu
    210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
            245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
            275                 280                 285

Ile Ile Thr Gly Asn Gly Gly Ile Gln Trp Ser Arg Gly Lys His Lys
            290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
            355                 360                 365

Ile Asp Gly Tyr Tyr Arg Leu Thr Ala Asp Ala His His Tyr Leu Cys
            370                 375                 380

Lys Glu Val Ala Pro Pro Ala Val Leu
385                 390

<210> SEQ ID NO 131
<211> LENGTH: 1179
```

```
<212> TYPE: DNA
<213> ORGANISM: Artificial sequence
<220> FEATURE:
<223> OTHER INFORMATION: Sequence encoding binding domain

<400> SEQUENCE: 131
atgggaatgg cctgccttac gatgacagaa atggagggaa catccacctc ttctatatat      60
cagaatggtg atatttctgg aaatgccaat tctatgaagc aaatagatcc agttcttcag     120
gtgtatcttt accattccct tgggaaatct gaggcagatt atctgacctt ccatctgggg     180
gagtatgttg cagaagaaat ctgtattgct gcttctaaag cttgtggtat cacacctgtg     240
tatcataata tgtttgcttt aatgagtgaa acagaaagga tctggtatcc acccaaccat     300
gtcttccata tagatgagtc aaccaggcat aatgtactct acagaataag attttacttt     360
cctcgttggt attgcagtgg cagcaacaga gcctatcggc atggaatatc tcgaggtgct     420
gaagctcctc ttcttgatga ctttgtcatg tcttacctct ttgctcagtg gcggcatgat     480
tttgtgcacg gatggataaa agtacctgtg actcatgaaa cacaggaaga atgtcttggg     540
atggcagtgt tagatatgat gagaaatagcc aagaaaacg atcaaacccc actggccatc     600
tataactcta tcagctacaa gacattctta ccaaaatgta ttcgagcaaa gatccaagac     660
tatcatattt tgacaaggaa gcgaataagg tacagatttc gcagatttat tcagcaattc     720
agccaatgca aagccactgc cagaaacttg aaacttaagt atcttataaa tctggaaact     780
ctgcagtctg ccttctacac agagaaattt gaagtaaaag aacctggaag tggtccttca     840
ggtgaggaga tttttgcaac cattataata actggaaacg tggaattca gtggtcaaga     900
gggaaacata agaaagtga gacactgaca gaacaggatt tacagttata ttgcgatttt    960
cctaatatta ttgatgtcag tattaagcaa gcaaaccaag agggttcaaa tgaaagccga    1020
gttgtaacta ccataagca agatggtaaa aatctggaaa ttgaacttag ctcattaagg    1080
gaagctttgt ctttcgtgtc attaattgat ggatattata gattaactgc agatgcacat    1140
cattacctct gtaaagaagt agcacctcca gccgtgctt                           1179

<210> SEQ ID NO 132
<211> LENGTH: 8
<212> TYPE: PRT
<213> ORGANISM: Artificial sequence
<220> FEATURE:
<223> OTHER INFORMATION: Binding domain

<400> SEQUENCE: 132

Trp Trp Val Tyr Asp Leu Leu Phe
1               5

<210> SEQ ID NO 133
<211> LENGTH: 24
<212> TYPE: DNA
<213> ORGANISM: Artificial sequence
<220> FEATURE:
<223> OTHER INFORMATION: Sequence encoding binding domain

<400> SEQUENCE: 133
tgatgggttt atgatcttct cttt                                            24

<210> SEQ ID NO 134
<211> LENGTH: 7
<212> TYPE: PRT
<213> ORGANISM: Artificial sequence
<220> FEATURE:
<223> OTHER INFORMATION: Binding domain
```

```
<220> FEATURE:
<221> NAME/KEY: MISC_FEATURE
<222> LOCATION: (3)..(3)
<223> OTHER INFORMATION: X is E or D

<400> SEQUENCE: 134

Phe Phe Xaa Leu Asp Tyr Leu
1               5

<210> SEQ ID NO 135
<211> LENGTH: 21
<212> TYPE: DNA
<213> ORGANISM: Artificial sequence
<220> FEATURE:
<223> OTHER INFORMATION: Sequence encoding binding domain
<220> FEATURE:
<221> NAME/KEY: misc_feature
<222> LOCATION: (7)..(9)
<223> OTHER INFORMATION: nnn is gaa or gat

<400> SEQUENCE: 135
ttctttnnnc tcgactacct c                                              21

<210> SEQ ID NO 136
<211> LENGTH: 29
<212> TYPE: PRT
<213> ORGANISM: Artificial sequence
<220> FEATURE:
<223> OTHER INFORMATION: Binding domain

<400> SEQUENCE: 136

Leu Asp Tyr His Phe Gly Leu Glu Glu Gly Glu Gly Ile Arg Asp Leu
1               5                   10                  15

Phe Asp Cys Asp Phe Gly Asp Leu Thr Pro Leu Asp Phe
            20                  25

<210> SEQ ID NO 137
<211> LENGTH: 87
<212> TYPE: DNA
<213> ORGANISM: Artificial sequence
<220> FEATURE:
<223> OTHER INFORMATION: Sequence encoding binding domain

<400> SEQUENCE: 137
ctcgactacc acttcggcct cgaggagggc gagggcatca gagacctctt cgactgtgac    60
tttggggacc tcaccccct ggatttc                                         87

<210> SEQ ID NO 138
<211> LENGTH: 549
<212> TYPE: PRT
<213> ORGANISM: Artificial sequence
<220> FEATURE:
<223> OTHER INFORMATION: Binding domain

<400> SEQUENCE: 138

Asn Thr Ile Gln Gln Leu Met Met Ile Leu Asn Ser Ala Ser Asp Gln
1               5                   10                  15

Pro Ser Glu Asn Leu Ile Ser Tyr Phe Asn Asn Cys Thr Val Asn Pro
            20                  25                  30

Lys Glu Ser Ile Leu Lys Arg Val Lys Asp Ile Gly Tyr Ile Phe Lys
        35                  40                  45

Glu Lys Phe Ala Lys Ala Val Gly Gln Gly Cys Val Glu Ile Gly Ser
    50                  55                  60

Gln Arg Tyr Lys Leu Gly Val Arg Leu Tyr Tyr Arg Val Met Glu Ser
```

-continued

```
                65                  70                  75                  80
Met Leu Lys Ser Glu Glu Arg Leu Ser Ile Gln Asn Phe Ser Lys
                    85                  90                  95

Leu Leu Asn Asp Asn Ile Phe His Met Ser Leu Leu Ala Cys Ala Leu
                100                 105                 110

Glu Val Val Met Ala Thr Tyr Ser Arg Ser Thr Ser Gln Asn Leu Asp
                115                 120                 125

Ser Gly Thr Asp Leu Ser Phe Pro Trp Ile Leu Asn Val Leu Asn Leu
                130                 135                 140

Lys Ala Phe Asp Phe Tyr Lys Val Ile Glu Ser Phe Ile Lys Ala Glu
145                 150                 155                 160

Gly Asn Leu Thr Arg Glu Met Ile Lys His Leu Glu Arg Cys Glu His
                165                 170                 175

Arg Ile Met Glu Ser Leu Ala Trp Leu Ser Asp Ser Pro Leu Phe Asp
                180                 185                 190

Leu Ile Lys Gln Ser Lys Asp Arg Glu Gly Pro Thr Asp His Leu Glu
                195                 200                 205

Ser Ala Cys Pro Leu Asn Leu Pro Leu Gln Asn Asn His Thr Ala Ala
210                 215                 220

Asp Met Tyr Leu Ser Pro Val Arg Ser Pro Lys Lys Gly Ser Thr
225                 230                 235                 240

Thr Arg Val Asn Ser Thr Ala Asn Ala Glu Thr Gln Ala Thr Ser Ala
                245                 250                 255

Phe Gln Thr Gln Lys Pro Leu Lys Ser Thr Ser Leu Ser Leu Phe Tyr
                260                 265                 270

Lys Lys Val Tyr Arg Leu Ala Tyr Leu Arg Leu Asn Thr Leu Cys Glu
                275                 280                 285

Arg Leu Leu Ser Glu His Pro Glu Leu Glu His Ile Ile Trp Thr Leu
                290                 295                 300

Phe Gln His Thr Leu Gln Asn Glu Tyr Glu Leu Met Arg Asp Arg His
305                 310                 315                 320

Leu Asp Gln Ile Met Met Cys Ser Met Tyr Gly Ile Cys Lys Val Lys
                325                 330                 335

Asn Ile Asp Leu Lys Phe Lys Ile Ile Val Thr Ala Tyr Lys Asp Leu
                340                 345                 350

Pro His Ala Val Gln Glu Thr Phe Lys Arg Val Leu Ile Lys Glu Glu
                355                 360                 365

Glu Tyr Asp Ser Ile Ile Val Phe Tyr Asn Ser Val Phe Met Gln Arg
                370                 375                 380

Leu Lys Thr Asn Ile Leu Gln Tyr Ala Ser Thr Arg Pro Pro Thr Leu
385                 390                 395                 400

Ser Pro Ile Pro His Ile Pro Arg Ser Pro Tyr Lys Phe Pro Ser Ser
                405                 410                 415

Pro Leu Arg Ile Pro Gly Gly Asn Ile Tyr Ile Ser Pro Leu Lys Ser
                420                 425                 430

Pro Tyr Lys Ile Ser Glu Gly Leu Pro Thr Pro Thr Lys Met Thr Pro
                435                 440                 445

Arg Ser Arg Ile Leu Val Ser Ile Gly Glu Ser Phe Gly Thr Ser Glu
                450                 455                 460

Lys Phe Gln Lys Ile Asn Gln Met Val Cys Asn Ser Asp Arg Val Leu
465                 470                 475                 480

Lys Arg Ser Ala Glu Gly Ser Asn Pro Pro Lys Pro Leu Lys Lys Leu
                485                 490                 495
```

```
Arg Phe Asp Ile Glu Gly Ser Asp Glu Ala Asp Gly Ser Lys His Leu
            500                 505                 510
Pro Gly Glu Ser Lys Phe Gln Gln Lys Leu Ala Glu Met Thr Ser Thr
        515                 520                 525
Arg Thr Arg Met Gln Lys Gln Lys Met Asn Asp Ser Met Asp Thr Ser
    530                 535                 540
Asn Lys Glu Glu Lys
545

<210> SEQ ID NO 139
<211> LENGTH: 1647
<212> TYPE: DNA
<213> ORGANISM: Artificial sequence
<220> FEATURE:
<223> OTHER INFORMATION: Sequence encoding binding domain

<400> SEQUENCE: 139
```

| | | | | | |
|---|---|---|---|---|---|
| aacactatcc | aacaattaat | gatgatttta | aattcagcaa | gtgatcaacc | ttcagaaaat | 60 |
| ctgatttcct | attttaacaa | ctgcacagtg | aatccaaaag | aaagtatact | gaaaagagtg | 120 |
| aaggatatag | gatacatctt | taaagagaaa | tttgctaaag | ctgtgggaca | gggttgtgtc | 180 |
| gaaattggat | cacagcgata | caaacttgga | gttcgcttgt | attaccgagt | aatggaatcc | 240 |
| atgcttaaat | cagaagaaga | acgattatcc | attcaaaatt | ttagcaaact | tctgaatgac | 300 |
| aacattttc | atatgtcttt | attggcgtgc | gctcttgagg | ttgtaatggc | acacatatagc | 360 |
| agaagtacat | ctcagaatct | tgattctgga | acagatttgt | ctttcccatg | gattctgaat | 420 |
| gtgcttaatt | taaagccttt | tgatttttac | aaagtgatcg | aaagttttat | caaagcagaa | 480 |
| ggcaacttga | caagagaaat | gataaaacat | ttagaacgat | gtgaacatcg | aatcatggaa | 540 |
| tcccttgcat | ggctctcaga | ttcacctta | tttgatctta | ttaaacaatc | aaaggaccga | 600 |
| gaaggaccaa | ctgatcacct | tgaatctgct | tgtcctctta | atcttcctct | ccagaataat | 660 |
| cacactgcag | cagatatgta | tcttctcct | gtaagatctc | caaagaaaaa | aggttcaact | 720 |
| acgcgtgtaa | attctactgc | aaatgcagag | acacaagcaa | cctcagcctt | ccagacccag | 780 |
| aagccattga | aatctacctc | tctttcactg | ttttataaaa | aagtgtatcg | gctagcctat | 840 |
| ctccggctaa | atacactttg | tgaacgcctt | ctgtctgagc | acccagaatt | agaacatatc | 900 |
| atctggaccc | ttttccagca | caccctgcag | aatgagtatg | aactcatgag | agacaggcat | 960 |
| ttggaccaaa | ttatgatgtg | ttccatgtat | ggcatatgca | aagtgaagaa | tatagacctt | 1020 |
| aaattcaaaa | tcattgtaac | agcatacaag | gatcttcctc | atgctgttca | ggagacattc | 1080 |
| aaacgtgttt | tgatcaaaga | agaggagtat | gattctatta | tagtattcta | taactcggtc | 1140 |
| ttcatgcaga | gactgaaaac | aaatattttg | cagtatgctt | ccaccaggcc | ccctaccttg | 1200 |
| tcaccaatac | ctcacattcc | tcgaagccct | tacaagtttc | ctagttcacc | cttacggatt | 1260 |
| cctggagga | acatctatat | ttcaccctg | aagagtccat | ataaaatttc | agaaggtctg | 1320 |
| ccaacaccaa | caaaaatgac | tccaagatca | agaatcttag | tatcaattgg | tgaatcattc | 1380 |
| gggacttctg | agaagttcca | gaaaataaat | cagatggtat | gtaacagcga | ccgtgtgctc | 1440 |
| aaaagaagtg | ctgaaggaag | caaccctcct | aaaccactga | aaaaactacg | ctttgatatt | 1500 |
| gaaggatcag | atgaagcaga | tggaagtaaa | catctcccag | gagagtccaa | atttcagcag | 1560 |
| aaactggcag | aaatgacttc | tactcgaaca | cgaatgcaaa | agcagaaaat | gaatgatagc | 1620 |
| atggatacct | caaacaagga | agagaaa | | | | 1647 |

<210> SEQ ID NO 140
<211> LENGTH: 6
<212> TYPE: PRT
<213> ORGANISM: Artificial sequence
<220> FEATURE:
<223> OTHER INFORMATION: Binding domain
<220> FEATURE:
<221> NAME/KEY: misc_feature
<222> LOCATION: (4)..(4)
<223> OTHER INFORMATION: X is any hydrophobic amino acid
<220> FEATURE:
<221> NAME/KEY: misc_feature
<222> LOCATION: (5)..(5)
<223> OTHER INFORMATION: X is any amino acid

<400> SEQUENCE: 140

Asp Ser Gly Xaa Xaa Ser
1               5

<210> SEQ ID NO 141
<211> LENGTH: 15
<212> TYPE: PRT
<213> ORGANISM: Artificial sequence
<220> FEATURE:
<223> OTHER INFORMATION: Binding domain

<400> SEQUENCE: 141

Pro Pro Leu Ser Gln Glu Thr Phe Ser Asp Leu Trp Lys Leu Leu
1               5                   10                  15

<210> SEQ ID NO 142
<211> LENGTH: 45
<212> TYPE: DNA
<213> ORGANISM: Artificial Sequence
<220> FEATURE:
<223> OTHER INFORMATION: Sequence encoding binding domain

<400> SEQUENCE: 142 cccctctga gtcaggaaac attttcagac ctatggaaac tactt         45

<210> SEQ ID NO 143
<211> LENGTH: 59
<212> TYPE: PRT
<213> ORGANISM: Artificial Sequence
<220> FEATURE:
<223> OTHER INFORMATION: Binding domain

<400> SEQUENCE: 143

Gly Ala Gln Lys Asp Thr Tyr Thr Met Lys Glu Val Leu Phe Tyr Leu
1               5                   10                  15

Gly Gln Tyr Ile Met Thr Lys Arg Leu Tyr Asp Glu Lys Gln Gln His
            20                  25                  30

Ile Val Tyr Cys Ser Asn Asp Leu Leu Gly Asp Leu Phe Gly Val Pro
        35                  40                  45

Ser Phe Ser Val Lys Glu His Arg Lys Ile Tyr
    50                  55

<210> SEQ ID NO 144
<211> LENGTH: 176
<212> TYPE: DNA
<213> ORGANISM: Artificial Sequence
<220> FEATURE:
<223> OTHER INFORMATION: Sequence encoding binding domain

<400> SEQUENCE: 144
ggtgcacaaa aagacactta tactatgaaa gaggttcttt tttatcttgg ccagtatatt    60

```
atgactaaac gattatatga tgagaagcaa caacatattg tatattgttc aaatgatctt    120
ctaggagatt tgtttggcgt gccaagcttc tctgtgaaag agcacaggaa aatata        176
```

<210> SEQ ID NO 145
<211> LENGTH: 7
<212> TYPE: PRT
<213> ORGANISM: Artificial sequence
<220> FEATURE:
<223> OTHER INFORMATION: Nuclear Localization Sequence

<400> SEQUENCE: 145

Pro Lys Lys Lys Arg Lys Val
1               5

<210> SEQ ID NO 146
<211> LENGTH: 6
<212> TYPE: PRT
<213> ORGANISM: Artificial sequence
<220> FEATURE:
<223> OTHER INFORMATION: Nuclear localization signal

<400> SEQUENCE: 146

Gln Arg Lys Arg Gln Lys
1               5

<210> SEQ ID NO 147
<211> LENGTH: 18
<212> TYPE: PRT
<213> ORGANISM: Artificial sequence
<220> FEATURE:
<223> OTHER INFORMATION: Nuclear localization signal

<400> SEQUENCE: 147

His Arg Ile Glu Glu Lys Arg Lys Arg Thr Tyr Glu Thr Phe Asp Lys
1               5                   10                  15

Ser Ile

<210> SEQ ID NO 148
<211> LENGTH: 9
<212> TYPE: PRT
<213> ORGANISM: Artificial sequence
<220> FEATURE:
<223> OTHER INFORMATION: Nuclear localization signal

<400> SEQUENCE: 148

Lys Lys Lys Lys Arg Lys Arg Glu Lys
1               5

<210> SEQ ID NO 149
<211> LENGTH: 9
<212> TYPE: PRT
<213> ORGANISM: Artificial sequence
<220> FEATURE:
<223> OTHER INFORMATION: Nuclear localization signal

<400> SEQUENCE: 149

Pro Ala Ala Lys Arg Val Lys Leu Asp
1               5

<210> SEQ ID NO 150
<211> LENGTH: 6
<212> TYPE: PRT
<213> ORGANISM: Artificial sequence
<220> FEATURE:
<223> OTHER INFORMATION: Nuclear localization signal

```
<400> SEQUENCE: 150

Gly Lys Lys Lys Lys Pro
1               5

<210> SEQ ID NO 151
<211> LENGTH: 6
<212> TYPE: PRT
<213> ORGANISM: Artificial sequence
<220> FEATURE:
<223> OTHER INFORMATION: Nuclear localization signal

<400> SEQUENCE: 151

Pro Lys Lys Lys Lys Pro
1               5

<210> SEQ ID NO 152
<211> LENGTH: 17
<212> TYPE: PRT
<213> ORGANISM: Artificial sequence
<220> FEATURE:
<223> OTHER INFORMATION: Nuclear localization signal
<220> FEATURE:
<221> NAME/KEY: MISC_FEATURE
<222> LOCATION: (3)..(13)
<223> OTHER INFORMATION: X is any amino acid

<400> SEQUENCE: 152

Lys Arg Xaa Xaa Xaa Xaa Xaa Xaa Xaa Xaa Xaa Xaa Xaa Lys Lys Leu
1               5                   10                  15

Arg

<210> SEQ ID NO 153
<211> LENGTH: 21
<212> TYPE: PRT
<213> ORGANISM: Artificial sequence
<220> FEATURE:
<223> OTHER INFORMATION: Nuclear localization signal
<220> FEATURE:
<221> NAME/KEY: MISC_FEATURE
<222> LOCATION: (3)..(17)
<223> OTHER INFORMATION: X is any amino acid

<400> SEQUENCE: 153

Lys Lys Xaa Xaa Xaa Xaa Xaa Xaa Xaa Xaa Xaa Xaa Xaa Xaa Xaa Xaa
1               5                   10                  15

Xaa Lys Lys Arg Lys
            20

<210> SEQ ID NO 154
<211> LENGTH: 14
<212> TYPE: PRT
<213> ORGANISM: Artificial sequence
<220> FEATURE:
<223> OTHER INFORMATION: Nuclear export signal

<400> SEQUENCE: 154

Cys Ile Gln Gln Gln Leu Gly Gln Leu Thr Leu Glu Asn Leu
1               5                   10

<210> SEQ ID NO 155
<211> LENGTH: 11
<212> TYPE: PRT
<213> ORGANISM: Artificial sequence
<220> FEATURE:
<223> OTHER INFORMATION: Nuclear export signal
```

-continued

```
<400> SEQUENCE: 155

Glu Leu Ala Leu Lys Leu Ala Gly Leu Asp Ile
1               5                   10

<210> SEQ ID NO 156
<211> LENGTH: 11
<212> TYPE: PRT
<213> ORGANISM: Artificial sequence
<220> FEATURE:
<223> OTHER INFORMATION: Nuclear export signal

<400> SEQUENCE: 156

Leu Gln Leu Pro Pro Leu Glu Arg Leu Thr Leu
1               5                   10

<210> SEQ ID NO 157
<211> LENGTH: 12
<212> TYPE: PRT
<213> ORGANISM: Artificial sequence
<220> FEATURE:
<223> OTHER INFORMATION: Nuclear export signal

<400> SEQUENCE: 157

Ala Leu Gln Lys Lys Leu Glu Glu Leu Glu Leu Asp
1               5                   10

<210> SEQ ID NO 158
<211> LENGTH: 12
<212> TYPE: PRT
<213> ORGANISM: Artificial sequence
<220> FEATURE:
<223> OTHER INFORMATION: Nuclear export signal

<400> SEQUENCE: 158

Thr Leu Trp Gln Phe Leu Leu His Leu Leu Leu Asp
1               5                   10

<210> SEQ ID NO 159
<211> LENGTH: 24
<212> TYPE: PRT
<213> ORGANISM: Artificial sequence
<220> FEATURE:
<223> OTHER INFORMATION: Nuclear localization sequence

<400> SEQUENCE: 159

Lys Arg Pro Ala Cys Thr Leu Lys Pro Glu Cys Val Gln Gln Leu Leu
1               5                   10                  15

Val Cys Ser Gln Glu Ala Lys Lys
            20

<210> SEQ ID NO 160
<211> LENGTH: 72
<212> TYPE: DNA
<213> ORGANISM: Artificial sequence
<220> FEATURE:
<223> OTHER INFORMATION: Sequence encoding NLS

<400> SEQUENCE: 160
aagcgtcctg cctgcaccct gaagcctgag tgtgtccagc agctgctggt ttgctcccag      60
gaggccaaga ag                                                         72

<210> SEQ ID NO 161
<211> LENGTH: 20
<212> TYPE: PRT
<213> ORGANISM: Artificial sequence
```

<220> FEATURE:
<223> OTHER INFORMATION: Nuclear localization sequence

<400> SEQUENCE: 161

Lys Asp Cys Ile Ile Asn Lys His His Arg Asn Arg Cys Gln Tyr Cys
1               5                   10                  15

Arg Leu Gln Arg
            20

<210> SEQ ID NO 162
<211> LENGTH: 60
<212> TYPE: DNA
<213> ORGANISM: Artificial sequence
<220> FEATURE:
<223> OTHER INFORMATION: Sequence encoding NLS

<400> SEQUENCE: 162
aaggattgta ttattaataa gcaccaccga aaccgctgtc aatactgcag gttacagaga       60

<210> SEQ ID NO 163
<211> LENGTH: 18
<212> TYPE: PRT
<213> ORGANISM: Artificial sequence
<220> FEATURE:
<223> OTHER INFORMATION: Nuclear localization signal

<400> SEQUENCE: 163

Lys Val Thr Lys Arg Lys His Asp Asn Glu Gly Ser Gly Ser Lys Arg
1               5                   10                  15

Pro Lys

<210> SEQ ID NO 164
<211> LENGTH: 54
<212> TYPE: DNA
<213> ORGANISM: Artificial sequence
<220> FEATURE:
<223> OTHER INFORMATION: Sequence encoding NLS

<400> SEQUENCE: 164
aaagttacca agagaaaaca cgataatgaa ggttctggaa gcaaaaggcc caag            54

<210> SEQ ID NO 165
<211> LENGTH: 17
<212> TYPE: PRT
<213> ORGANISM: Artificial sequence
<220> FEATURE:
<223> OTHER INFORMATION: Nuclear localization signal

<400> SEQUENCE: 165

Arg Lys Cys Leu Gln Ala Gly Met Asn Leu Glu Ala Arg Lys Thr Lys
1               5                   10                  15

Lys

<210> SEQ ID NO 166
<211> LENGTH: 51
<212> TYPE: DNA
<213> ORGANISM: Artificial sequence
<220> FEATURE:
<223> OTHER INFORMATION: Sequence encoding NLS

<400> SEQUENCE: 166
cgaaaatgtc ttcaggctgg aatgaacctg gaagctcgaa aaacaaagaa a              51

<210> SEQ ID NO 167

```
<211> LENGTH: 17
<212> TYPE: PRT
<213> ORGANISM: Artificial sequence
<220> FEATURE:
<223> OTHER INFORMATION: Nuclear localization signal

<400> SEQUENCE: 167

Lys Arg Met Arg Asn Arg Ile Ala Ala Ser Lys Cys Arg Lys Arg Lys
1               5                   10                  15

Leu

<210> SEQ ID NO 168
<211> LENGTH: 51
<212> TYPE: DNA
<213> ORGANISM: Artificial sequence
<220> FEATURE:
<223> OTHER INFORMATION: Sequence encoding NLS

<400> SEQUENCE: 168
aagcgcatga ggaaccgcat cgctgcctcc aagtgccgaa aaggaagct g            51

<210> SEQ ID NO 169
<211> LENGTH: 17
<212> TYPE: PRT
<213> ORGANISM: Artificial sequence
<220> FEATURE:
<223> OTHER INFORMATION: Nuclear localization signal

<400> SEQUENCE: 169

Lys Lys Gln Thr Thr Leu Ala Phe Lys Pro Ile Lys Lys Gly Lys Lys
1               5                   10                  15

Arg

<210> SEQ ID NO 170
<211> LENGTH: 51
<212> TYPE: DNA
<213> ORGANISM: Artificial sequence
<220> FEATURE:
<223> OTHER INFORMATION: Sequence encoding NLS

<400> SEQUENCE: 170
aagaaacaaa ctacattggc atttaagcca atcaaaaaag gaaagaagag a           51

<210> SEQ ID NO 171
<211> LENGTH: 17
<212> TYPE: PRT
<213> ORGANISM: Artificial sequence
<220> FEATURE:
<223> OTHER INFORMATION: Nuclear localization signal

<400> SEQUENCE: 171

Arg Lys Glu Trp Leu Thr Asn Phe Met Glu Asp Arg Arg Gln Arg Arg
1               5                   10                  15

Leu

<210> SEQ ID NO 172
<211> LENGTH: 51
<212> TYPE: DNA
<213> ORGANISM: Artificial sequence
<220> FEATURE:
<223> OTHER INFORMATION: Sequence encoding NLS

<400> SEQUENCE: 172
agaaaagaat ggttaacaaa ttttatggaa gaccggagac agcgtaggct a           51
```

<210> SEQ ID NO 173
<211> LENGTH: 23
<212> TYPE: PRT
<213> ORGANISM: Artificial sequence
<220> FEATURE:
<223> OTHER INFORMATION: Nuclear localization signal

<400> SEQUENCE: 173

Arg Ala Ile Lys Arg Arg Pro Gly Leu Asp Phe Asp Asp Asp Gly Glu
1               5                   10                  15

Gly Asn Ser Lys Phe Leu Arg
            20

<210> SEQ ID NO 174
<211> LENGTH: 69
<212> TYPE: DNA
<213> ORGANISM: Artificial sequence
<220> FEATURE:
<223> OTHER INFORMATION: Sequence encoding NLS

<400> SEQUENCE: 174
agggctatta agcggcgacc agggctggat tttgatgatg atggagaagg gaacagtaaa      60
tttttgagg                                                              69

<210> SEQ ID NO 175
<211> LENGTH: 18
<212> TYPE: PRT
<213> ORGANISM: Artificial sequence
<220> FEATURE:
<223> OTHER INFORMATION: Nuclear localization signal

<400> SEQUENCE: 175

Arg Lys Arg Lys Lys Met Pro Ala Ser Gln Arg Ser Lys Arg Arg Lys
1               5                   10                  15

Thr Ala

<210> SEQ ID NO 176
<211> LENGTH: 54
<212> TYPE: DNA
<213> ORGANISM: Artificial sequence
<220> FEATURE:
<223> OTHER INFORMATION: Sequence encoding NLS

<400> SEQUENCE: 176
aggaagagga aaaagatgcc agcctcccaa aggtctaaga ggagaaaaac tgct            54

<210> SEQ ID NO 177
<211> LENGTH: 30
<212> TYPE: PRT
<213> ORGANISM: Artificial sequence
<220> FEATURE:
<223> OTHER INFORMATION: Nuclear localization signal

<400> SEQUENCE: 177

Met Pro Thr Glu Glu Arg Val Arg Lys Arg Lys Glu Ser Asn Arg Glu
1               5                   10                  15

Ser Ala Arg Arg Ser Arg Tyr Arg Lys Ala Ala His Leu Lys
            20                  25                  30

<210> SEQ ID NO 178
<211> LENGTH: 90
<212> TYPE: DNA
<213> ORGANISM: Artificial sequence
<220> FEATURE:

-continued

<223> OTHER INFORMATION: Sequence encoding NLS

<400> SEQUENCE: 178
atgcctaccg aggaaagagt gaggaaaaga aaggaatcca atagagaatc agccagacgc    60
tcgagataca ggaaagccgc tcacctgaaa                                    90

<210> SEQ ID NO 179
<211> LENGTH: 7
<212> TYPE: PRT
<213> ORGANISM: Artificial sequence
<220> FEATURE:
<223> OTHER INFORMATION: Nuclear localization signal

<400> SEQUENCE: 179

Arg Arg Met Lys Trp Lys Lys
1               5

<210> SEQ ID NO 180
<211> LENGTH: 7
<212> TYPE: PRT
<213> ORGANISM: Artificial sequence
<220> FEATURE:
<223> OTHER INFORMATION: Nuclear localization signal

<400> SEQUENCE: 180

Arg Val His Pro Tyr Gln Arg
1               5

<210> SEQ ID NO 181
<211> LENGTH: 24
<212> TYPE: PRT
<213> ORGANISM: Artificial sequence
<220> FEATURE:
<223> OTHER INFORMATION: Nuclear localization signal

<400> SEQUENCE: 181

Lys Arg Pro Ala Cys Thr Leu Lys Pro Glu Cys Val Gln Gln Leu Leu
1               5                   10                  15

Val Cys Ser Gln Glu Ala Lys Lys
            20

<210> SEQ ID NO 182
<211> LENGTH: 7
<212> TYPE: PRT
<213> ORGANISM: Artificial sequence
<220> FEATURE:
<223> OTHER INFORMATION: Nuclear localization signal

<400> SEQUENCE: 182

Pro Lys Lys Lys Arg Lys Val
1               5

<210> SEQ ID NO 183
<211> LENGTH: 7
<212> TYPE: PRT
<213> ORGANISM: Artificial sequence
<220> FEATURE:
<223> OTHER INFORMATION: Nuclear localization signal

<400> SEQUENCE: 183

Gly Lys Lys Arg Ser Lys Ala
1               5

<210> SEQ ID NO 184
<211> LENGTH: 6

```
<212> TYPE: PRT
<213> ORGANISM: Artificial sequence
<220> FEATURE:
<223> OTHER INFORMATION: Nuclear localization signal

<400> SEQUENCE: 184

Lys Ala Lys Arg Gln Arg
1               5

<210> SEQ ID NO 185
<211> LENGTH: 8
<212> TYPE: PRT
<213> ORGANISM: Artificial sequence
<220> FEATURE:
<223> OTHER INFORMATION: Nuclear localization signal

<400> SEQUENCE: 185

Arg Gly Arg Arg Arg Arg Gln Arg
1               5

<210> SEQ ID NO 186
<211> LENGTH: 5
<212> TYPE: PRT
<213> ORGANISM: Artificial sequence
<220> FEATURE:
<223> OTHER INFORMATION: Nuclear localization signal

<400> SEQUENCE: 186

Arg Lys Arg Arg Arg
1               5

<210> SEQ ID NO 187
<211> LENGTH: 9
<212> TYPE: PRT
<213> ORGANISM: Artificial sequence
<220> FEATURE:
<223> OTHER INFORMATION: Nuclear localization signal

<400> SEQUENCE: 187

Pro Pro Val Lys Arg Glu Arg Thr Ser
1               5

<210> SEQ ID NO 188
<211> LENGTH: 10
<212> TYPE: PRT
<213> ORGANISM: Artificial sequence
<220> FEATURE:
<223> OTHER INFORMATION: Nuclear localization signal

<400> SEQUENCE: 188

Pro Tyr Leu Asn Lys Arg Lys Gly Lys Pro
1               5                   10

<210> SEQ ID NO 189
<211> LENGTH: 17
<212> TYPE: PRT
<213> ORGANISM: Artificial sequence
<220> FEATURE:
<223> OTHER INFORMATION: Nuclear localization signal

<400> SEQUENCE: 189

Cys Tyr Gly Ser Lys Asn Thr Gly Ala Lys Lys Arg Lys Ile Asp Asp
1               5                   10                  15

Ala

<210> SEQ ID NO 190
```

```
<211> LENGTH: 9
<212> TYPE: PRT
<213> ORGANISM: Artificial sequence
<220> FEATURE:
<223> OTHER INFORMATION: Nuclear localization signal

<400> SEQUENCE: 190

Lys Lys Lys Lys Arg Lys Arg Glu Lys
1               5

<210> SEQ ID NO 191
<211> LENGTH: 9
<212> TYPE: PRT
<213> ORGANISM: Artificial sequence
<220> FEATURE:
<223> OTHER INFORMATION: Nuclear localization signal

<400> SEQUENCE: 191

Lys Lys Lys Arg Arg Ser Arg Glu Lys
1               5

<210> SEQ ID NO 192
<211> LENGTH: 10
<212> TYPE: PRT
<213> ORGANISM: Artificial sequence
<220> FEATURE:
<223> OTHER INFORMATION: Nuclear localization signal
<220> FEATURE:
<221> NAME/KEY: MISC_FEATURE
<222> LOCATION: (3)..(3)
<223> OTHER INFORMATION: X is 7 to 9 amino acids

<400> SEQUENCE: 192

Lys Arg Xaa Pro Gln Pro Lys Lys Lys Pro
1               5                   10

<210> SEQ ID NO 193
<211> LENGTH: 18
<212> TYPE: PRT
<213> ORGANISM: Artificial sequence
<220> FEATURE:
<223> OTHER INFORMATION: Nuclear localization signal

<400> SEQUENCE: 193

Lys Val Thr Lys Arg Lys His Asp Asn Glu Gly Ser Gly Ser Lys Arg
1               5                   10                  15

Pro Lys

<210> SEQ ID NO 194
<211> LENGTH: 32
<212> TYPE: PRT
<213> ORGANISM: Artificial sequence
<220> FEATURE:
<223> OTHER INFORMATION: Nuclear localization signal
<220> FEATURE:
<221> NAME/KEY: MISC_FEATURE
<222> LOCATION: (10)..(28)
<223> OTHER INFORMATION: X is any amino acid

<400> SEQUENCE: 194

Arg Leu Lys Lys Leu Lys Cys Ser Lys Xaa Xaa Xaa Xaa Xaa Xaa Xaa
1               5                   10                  15

Xaa Xaa Xaa Xaa Xaa Xaa Xaa Xaa Xaa Xaa Xaa Xaa Lys Thr Lys Arg
                20                  25                  30

<210> SEQ ID NO 195
<211> LENGTH: 32
```

-continued

```
<212> TYPE: PRT
<213> ORGANISM: Artificial sequence
<220> FEATURE:
<223> OTHER INFORMATION: Nuclear localization signal
<220> FEATURE:
<221> NAME/KEY: MISC_FEATURE
<222> LOCATION: (10)..(27)
<223> OTHER INFORMATION: X is any amino acid

<400> SEQUENCE: 195

Arg Lys Arg Ile Arg Glu Asp Arg Lys Xaa Xaa Xaa Xaa Xaa Xaa
1               5                   10                  15

Xaa Xaa Xaa Xaa Xaa Xaa Xaa Xaa Xaa Xaa Xaa Arg Lys Arg Lys Arg
            20                  25                  30

<210> SEQ ID NO 196
<211> LENGTH: 15
<212> TYPE: PRT
<213> ORGANISM: Artificial sequence
<220> FEATURE:
<223> OTHER INFORMATION: Nuclear localization signal
<220> FEATURE:
<221> NAME/KEY: MISC_FEATURE
<222> LOCATION: (5)..(8)
<223> OTHER INFORMATION: X is any amino acid

<400> SEQUENCE: 196

Arg Arg Glu Arg Xaa Xaa Xaa Xaa Arg Pro Arg Lys Ile Pro Arg
1               5                   10                  15

<210> SEQ ID NO 197
<211> LENGTH: 14
<212> TYPE: PRT
<213> ORGANISM: Artificial sequence
<220> FEATURE:
<223> OTHER INFORMATION: Nuclear localization signal

<400> SEQUENCE: 197

Lys Lys Lys Lys Lys Glu Glu Glu Gly Glu Gly Lys Lys Lys
1               5                   10

<210> SEQ ID NO 198
<211> LENGTH: 8
<212> TYPE: PRT
<213> ORGANISM: Artificial sequence
<220> FEATURE:
<223> OTHER INFORMATION: Nuclear localization signal

<400> SEQUENCE: 198

Pro Arg Pro Arg Lys Ile Pro Arg
1               5

<210> SEQ ID NO 199
<211> LENGTH: 13
<212> TYPE: PRT
<213> ORGANISM: Artificial sequence
<220> FEATURE:
<223> OTHER INFORMATION: Nuclear localization signal

<400> SEQUENCE: 199

Pro Pro Arg Ile Tyr Pro Gln Leu Pro Ser Ala Pro Thr
1               5                   10

<210> SEQ ID NO 200
<211> LENGTH: 20
<212> TYPE: PRT
<213> ORGANISM: Artificial sequence
<220> FEATURE:
```

<223> OTHER INFORMATION: Nuclear localization signal

<400> SEQUENCE: 200

Lys Asp Cys Val Ile Asn Lys His His Arg Asn Arg Cys Gln Tyr Cys
1               5                   10                  15

Arg Leu Gln Arg
            20

<210> SEQ ID NO 201
<211> LENGTH: 15
<212> TYPE: PRT
<213> ORGANISM: Artificial sequence
<220> FEATURE:
<223> OTHER INFORMATION: Nuclear localization signal
<220> FEATURE:
<221> NAME/KEY: MISC_FEATURE
<222> LOCATION: (3)..(10)
<223> OTHER INFORMATION: X is any amino acid
<220> FEATURE:
<221> NAME/KEY: MISC_FEATURE
<222> LOCATION: (3)..(11)
<223> OTHER INFORMATION: X is any amino acid

<400> SEQUENCE: 201

Lys Arg Xaa Xaa Xaa Xaa Xaa Xaa Xaa Xaa Xaa Lys Thr Lys Lys
1               5                   10                  15

<210> SEQ ID NO 202
<211> LENGTH: 11
<212> TYPE: PRT
<213> ORGANISM: Artificial sequence
<220> FEATURE:
<223> OTHER INFORMATION: Nuclear localization signal

<400> SEQUENCE: 202

Ala Pro Lys Arg Lys Ser Gly Val Ser Lys Cys
1               5                   10

<210> SEQ ID NO 203
<211> LENGTH: 9
<212> TYPE: PRT
<213> ORGANISM: Artificial sequence
<220> FEATURE:
<223> OTHER INFORMATION: Nuclear localization signal

<400> SEQUENCE: 203

Arg Lys Lys Arg Arg Gln Arg Arg Arg
1               5

<210> SEQ ID NO 204
<211> LENGTH: 12
<212> TYPE: PRT
<213> ORGANISM: Artificial sequence
<220> FEATURE:
<223> OTHER INFORMATION: Nuclear localization signal

<400> SEQUENCE: 204

Arg Gln Ala Arg Arg Asn Arg Arg Arg Arg Trp Arg
1               5                   10

<210> SEQ ID NO 205
<211> LENGTH: 18
<212> TYPE: PRT
<213> ORGANISM: Artificial sequence
<220> FEATURE:
<223> OTHER INFORMATION: Nuclear localization signal

<400> SEQUENCE: 205

```
Met Pro Lys Thr Arg Arg Arg Pro Arg Arg Ser Gln Arg Lys Arg Pro
1               5                   10                  15

Pro Thr

<210> SEQ ID NO 206
<211> LENGTH: 17
<212> TYPE: PRT
<213> ORGANISM: Artificial sequence
<220> FEATURE:
<223> OTHER INFORMATION: Nuclear localization signal

<400> SEQUENCE: 206

Lys Arg Pro Met Asn Ala Phe Ile Val Trp Ser Arg Asp Gln Arg Arg
1               5                   10                  15

Lys

<210> SEQ ID NO 207
<211> LENGTH: 5
<212> TYPE: PRT
<213> ORGANISM: Artificial sequence
<220> FEATURE:
<223> OTHER INFORMATION: Nuclear localization signal

<400> SEQUENCE: 207

Pro Arg Arg Arg Lys
1               5

<210> SEQ ID NO 208
<211> LENGTH: 17
<212> TYPE: PRT
<213> ORGANISM: Artificial sequence
<220> FEATURE:
<223> OTHER INFORMATION: Nuclear localization signal

<400> SEQUENCE: 208

Lys Arg Pro Met Asn Ala Phe Met Val Trp Ala Gln Ala Ala Arg Arg
1               5                   10                  15

Lys

<210> SEQ ID NO 209
<211> LENGTH: 5
<212> TYPE: PRT
<213> ORGANISM: Artificial sequence
<220> FEATURE:
<223> OTHER INFORMATION: Nuclear localization signal

<400> SEQUENCE: 209

Pro Arg Arg Arg Lys
1               5

<210> SEQ ID NO 210
<211> LENGTH: 30
<212> TYPE: PRT
<213> ORGANISM: Artificial sequence
<220> FEATURE:
<223> OTHER INFORMATION: Nuclear localization signal
<220> FEATURE:
<221> NAME/KEY: MISC_FEATURE
<222> LOCATION: (1)..(1)
<223> OTHER INFORMATION: X is K, A, or R
<220> FEATURE:
<221> NAME/KEY: MISC_FEATURE
<222> LOCATION: (30)..(30)
<223> OTHER INFORMATION: X is K or A

<400> SEQUENCE: 210
```

-continued

```
Xaa Thr Pro Ile Gln Lys His Trp Arg Pro Thr Val Leu Thr Glu Gly
1               5                  10                  15

Pro Pro Val Lys Ile Arg Ile Glu Thr Gly Glu Trp Glu Xaa
            20                  25                  30
```

<210> SEQ ID NO 211
<211> LENGTH: 9
<212> TYPE: PRT
<213> ORGANISM: Artificial sequence
<220> FEATURE:
<223> OTHER INFORMATION: Nuclear localization signal

<400> SEQUENCE: 211

```
Pro Pro Arg Lys Lys Arg Thr Val Val
1               5
```

<210> SEQ ID NO 212
<211> LENGTH: 13
<212> TYPE: PRT
<213> ORGANISM: Artificial sequence
<220> FEATURE:
<223> OTHER INFORMATION: Nuclear localization signal

<400> SEQUENCE: 212

```
Tyr Lys Arg Pro Cys Lys Arg Ser Phe Ile Arg Phe Ile
1               5                  10
```

<210> SEQ ID NO 213
<211> LENGTH: 13
<212> TYPE: PRT
<213> ORGANISM: Artificial sequence
<220> FEATURE:
<223> OTHER INFORMATION: Nuclear localization signal

<400> SEQUENCE: 213

```
Leu Lys Asp Val Arg Lys Arg Lys Leu Gly Pro Gly His
1               5                  10
```

<210> SEQ ID NO 214
<211> LENGTH: 5
<212> TYPE: PRT
<213> ORGANISM: Artificial sequence
<220> FEATURE:
<223> OTHER INFORMATION: Nuclear localization signal

<400> SEQUENCE: 214

```
Lys Arg Pro Arg Pro
1               5
```

<210> SEQ ID NO 215
<211> LENGTH: 5
<212> TYPE: PRT
<213> ORGANISM: Artificial sequence
<220> FEATURE:
<223> OTHER INFORMATION: Nuclear localization signal

<400> SEQUENCE: 215

```
Arg Lys Arg Lys Lys
1               5
```

<210> SEQ ID NO 216
<211> LENGTH: 7
<212> TYPE: PRT
<213> ORGANISM: Artificial sequence
<220> FEATURE:
<223> OTHER INFORMATION: Nuclear localization signal

```
<400> SEQUENCE: 216

Arg Arg Ser Met Lys Arg Lys
1               5

<210> SEQ ID NO 217
<211> LENGTH: 10
<212> TYPE: PRT
<213> ORGANISM: Artificial sequence
<220> FEATURE:
<223> OTHER INFORMATION: Nuclear localization signal

<400> SEQUENCE: 217

Pro Ala Lys Arg Ala Arg Arg Gly Tyr Lys
1               5                   10

<210> SEQ ID NO 218
<211> LENGTH: 17
<212> TYPE: PRT
<213> ORGANISM: Artificial sequence
<220> FEATURE:
<223> OTHER INFORMATION: Nuclear localization signal

<400> SEQUENCE: 218

Arg Lys Cys Leu Gln Ala Gly Met Asn Leu Glu Ala Arg Lys Thr Lys
1               5                   10                  15

Lys

<210> SEQ ID NO 219
<211> LENGTH: 17
<212> TYPE: PRT
<213> ORGANISM: Artificial sequence
<220> FEATURE:
<223> OTHER INFORMATION: Nuclear localization signal

<400> SEQUENCE: 219

Arg Arg Glu Arg Asn Lys Met Ala Ala Ala Lys Cys Arg Asn Arg Arg
1               5                   10                  15

Arg

<210> SEQ ID NO 220
<211> LENGTH: 17
<212> TYPE: PRT
<213> ORGANISM: Artificial sequence
<220> FEATURE:
<223> OTHER INFORMATION: Nuclear localization signal

<400> SEQUENCE: 220

Lys Arg Met Arg Asn Arg Ile Ala Ala Ser Lys Cys Arg Lys Arg Lys
1               5                   10                  15

Leu

<210> SEQ ID NO 221
<211> LENGTH: 17
<212> TYPE: PRT
<213> ORGANISM: Artificial sequence
<220> FEATURE:
<223> OTHER INFORMATION: Nuclear localization signal

<400> SEQUENCE: 221

Lys Lys Ser Lys Lys Gly Arg Gln Glu Ala Leu Glu Arg Leu Lys Lys
1               5                   10                  15

Ala
```

```
<210> SEQ ID NO 222
<211> LENGTH: 17
<212> TYPE: PRT
<213> ORGANISM: Artificial sequence
<220> FEATURE:
<223> OTHER INFORMATION: Nuclear localization signal

<400> SEQUENCE: 222

Arg Lys Glu Trp Leu Thr Asn Phe Met Glu Asp Arg Arg Gln Arg Lys
1               5                   10                  15

Leu

<210> SEQ ID NO 223
<211> LENGTH: 17
<212> TYPE: PRT
<213> ORGANISM: Artificial sequence
<220> FEATURE:
<223> OTHER INFORMATION: Nuclear localization signal

<400> SEQUENCE: 223

Lys Lys Gln Thr Thr Leu Ala Phe Lys Pro Ile Lys Lys Gly Lys Lys
1               5                   10                  15

Arg

<210> SEQ ID NO 224
<211> LENGTH: 17
<212> TYPE: PRT
<213> ORGANISM: Artificial sequence
<220> FEATURE:
<223> OTHER INFORMATION: Nuclear localization signal

<400> SEQUENCE: 224

Arg Lys Arg Lys Lys Met Pro Ala Ser Gln Arg Ser Lys Arg Arg Lys
1               5                   10                  15

Thr

<210> SEQ ID NO 225
<211> LENGTH: 23
<212> TYPE: PRT
<213> ORGANISM: Artificial sequence
<220> FEATURE:
<223> OTHER INFORMATION: Nuclear localization signal

<400> SEQUENCE: 225

Arg Ala Ile Lys Arg Arg Pro Gly Leu Asp Phe Asp Asp Asp Gly Glu
1               5                   10                  15

Gly Asn Ser Lys Phe Leu Arg
            20

<210> SEQ ID NO 226
<211> LENGTH: 11
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (2)..(2)
<223> OTHER INFORMATION: X is any amino acid
<220> FEATURE:
<221> NAME/KEY: misc_feature
<222> LOCATION: (9)..(10)
<223> OTHER INFORMATION: X is any amino acid

<400> SEQUENCE: 226
```

```
Ser Xaa Gly Thr Lys Arg Ser Tyr Xaa Xaa Met
1               5                   10

<210> SEQ ID NO 227
<211> LENGTH: 8
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (5)..(7)
<223> OTHER INFORMATION: X is any amino acid

<400> SEQUENCE: 227

Thr Lys Arg Ser Xaa Xaa Xaa Met
1               5

<210> SEQ ID NO 228
<211> LENGTH: 7
<212> TYPE: PRT
<213> ORGANISM: Artificial sequence
<220> FEATURE:
<223> OTHER INFORMATION: Nuclear localization signal

<400> SEQUENCE: 228

Arg Ile Arg Lys Lys Leu Arg
1               5

<210> SEQ ID NO 229
<211> LENGTH: 18
<212> TYPE: PRT
<213> ORGANISM: Artificial sequence
<220> FEATURE:
<223> OTHER INFORMATION: Nuclear localization signal

<400> SEQUENCE: 229

Lys Arg Ala Ala Glu Asp Asp Glu Asp Asp Val Asp Thr Lys Lys
1               5                   10                  15

Gln Lys

<210> SEQ ID NO 230
<211> LENGTH: 8
<212> TYPE: PRT
<213> ORGANISM: Artificial sequence
<220> FEATURE:
<223> OTHER INFORMATION: Nuclear localization signal

<400> SEQUENCE: 230

Gly Arg Lys Arg Lys Lys Arg Thr
1               5

<210> SEQ ID NO 231
<211> LENGTH: 6
<212> TYPE: PRT
<213> ORGANISM: Artificial sequence
<220> FEATURE:
<223> OTHER INFORMATION: Nuclear localization signal

<400> SEQUENCE: 231

Lys Lys Lys Gln Lys Lys
1               5

<210> SEQ ID NO 232
<211> LENGTH: 13
<212> TYPE: PRT
<213> ORGANISM: Artificial sequence
```

```
<220> FEATURE:
<223> OTHER INFORMATION: Nuclear localization signal

<400> SEQUENCE: 232

Arg Glu Lys Lys Glu Lys Glu Gln Lys Glu Lys Cys Ala
1               5                   10

<210> SEQ ID NO 233
<211> LENGTH: 13
<212> TYPE: PRT
<213> ORGANISM: Artificial sequence
<220> FEATURE:
<223> OTHER INFORMATION: Nuclear localization signal

<400> SEQUENCE: 233

Leu Glu Lys Lys Val Lys Lys Lys Phe Asp Trp Cys Ala
1               5                   10

<210> SEQ ID NO 234
<211> LENGTH: 13
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (5)..(5)
<223> OTHER INFORMATION: X is Q or G

<400> SEQUENCE: 234

Thr Glu Lys Lys Xaa Lys Ser Ile Leu Tyr Asp Cys Ala
1               5                   10

<210> SEQ ID NO 235
<211> LENGTH: 15
<212> TYPE: PRT
<213> ORGANISM: Artificial sequence
<220> FEATURE:
<223> OTHER INFORMATION: Nuclear localization signal

<400> SEQUENCE: 235

Ser Asp Lys Lys Val Arg Ser Arg Leu Ile Glu Cys Ala Thr Ala
1               5                   10                  15

<210> SEQ ID NO 236
<211> LENGTH: 7
<212> TYPE: PRT
<213> ORGANISM: Artificial sequence
<220> FEATURE:
<223> OTHER INFORMATION: Nuclear localization signal

<400> SEQUENCE: 236

Leu Lys Arg Lys Leu Gln Arg
1               5

<210> SEQ ID NO 237
<211> LENGTH: 7
<212> TYPE: PRT
<213> ORGANISM: Artificial sequence
<220> FEATURE:
<223> OTHER INFORMATION: Nuclear localization signal

<400> SEQUENCE: 237

Arg Arg Lys Gly Lys Glu Lys
1               5

<210> SEQ ID NO 238
```

```
<211> LENGTH: 13
<212> TYPE: PRT
<213> ORGANISM: Artificial sequence
<220> FEATURE:
<223> OTHER INFORMATION: Nuclear localization signal

<400> SEQUENCE: 238

Cys Lys Arg Lys Thr Thr Asn Ala Asp Arg Arg Lys Ala
1               5                   10

<210> SEQ ID NO 239
<211> LENGTH: 11
<212> TYPE: PRT
<213> ORGANISM: Artificial sequence
<220> FEATURE:
<223> OTHER INFORMATION: Nuclear localization signal

<400> SEQUENCE: 239

Val Asn Glu Ala Phe Glu Thr Leu Lys Arg Cys
1               5                   10

<210> SEQ ID NO 240
<211> LENGTH: 30
<212> TYPE: PRT
<213> ORGANISM: Artificial sequence
<220> FEATURE:
<223> OTHER INFORMATION: Nuclear localization signal

<400> SEQUENCE: 240

Met Pro Thr Glu Glu Arg Val Arg Lys Arg Lys Glu Ser Asn Arg Glu
1               5                   10                  15

Ser Ala Arg Arg Ser Arg Tyr Arg Lys Ala Ala His Leu Lys
            20                  25                  30

<210> SEQ ID NO 241
<211> LENGTH: 21
<212> TYPE: PRT
<213> ORGANISM: Artificial sequence
<220> FEATURE:
<223> OTHER INFORMATION: Nuclear localization signal

<400> SEQUENCE: 241

Lys Val Asn Ser Arg Lys Arg Arg Lys Glu Val Pro Gly Pro Asn Gly
1               5                   10                  15

Ala Thr Glu Glu Asp
            20

<210> SEQ ID NO 242
<211> LENGTH: 6
<212> TYPE: PRT
<213> ORGANISM: Artificial sequence
<220> FEATURE:
<223> OTHER INFORMATION: Nuclear localization signal

<400> SEQUENCE: 242

Pro Arg Arg Gly Pro Arg
1               5

<210> SEQ ID NO 243
<211> LENGTH: 14
<212> TYPE: PRT
<213> ORGANISM: Artificial sequence
<220> FEATURE:
<223> OTHER INFORMATION: Nuclear localization signal

<400> SEQUENCE: 243
```

```
Pro Arg Gly Arg Arg Gln Pro Ile Pro Lys Ala Arg Gln Pro
1               5                   10
```

<210> SEQ ID NO 244
<211> LENGTH: 17
<212> TYPE: PRT
<213> ORGANISM: Artificial sequence
<220> FEATURE:
<223> OTHER INFORMATION: Nuclear localization signal

<400> SEQUENCE: 244

```
Lys Arg Ser Ala Glu Gly Gly Asn Pro Pro Lys Pro Leu Lys Lys Leu
1               5                   10                  15

Arg
```

<210> SEQ ID NO 245
<211> LENGTH: 20
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (4)..(14)
<223> OTHER INFORMATION: X is any amino acid

<400> SEQUENCE: 245

```
Lys Arg Lys Xaa Xaa Xaa Xaa Xaa Xaa Xaa Xaa Xaa Xaa Xaa Lys Lys
1               5                   10                  15

Lys Ser Lys Lys
            20
```

<210> SEQ ID NO 246
<211> LENGTH: 11
<212> TYPE: PRT
<213> ORGANISM: Artificial sequence
<220> FEATURE:
<223> OTHER INFORMATION: Nuclear localization signal

<400> SEQUENCE: 246

```
Glu Tyr Leu Ser Arg Lys Gly Lys Leu Glu Leu
1               5                   10
```

<210> SEQ ID NO 247
<211> LENGTH: 20
<212> TYPE: PRT
<213> ORGANISM: Artificial sequence
<220> FEATURE:
<223> OTHER INFORMATION: Nuclear localization signal

<400> SEQUENCE: 247

```
Pro Lys Arg Pro Arg Asp Arg His Asp Gly Glu Leu Gly Gly Arg Lys
1               5                   10                  15

Arg Ala Arg Gly
            20
```

<210> SEQ ID NO 248
<211> LENGTH: 32
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (19)..(28)
<223> OTHER INFORMATION: X is any amino acid

```
<400> SEQUENCE: 248

Lys Arg Pro Ala Ala Thr Lys Lys Ala Gly Gln Ala Lys Lys Lys
1               5                   10                  15

Lys Arg Xaa Xaa Xaa Xaa Xaa Xaa Xaa Xaa Xaa Lys Lys Lys Leu
            20                  25                  30

<210> SEQ ID NO 249
<211> LENGTH: 18
<212> TYPE: PRT
<213> ORGANISM: Artificial sequence
<220> FEATURE:
<223> OTHER INFORMATION: Nuclear localization signal

<400> SEQUENCE: 249

Lys Arg Lys Lys Glu Met Ala Asn Lys Ser Ala Pro Glu Ala Lys Lys
1               5                   10                  15

Lys Lys

<210> SEQ ID NO 250
<211> LENGTH: 19
<212> TYPE: PRT
<213> ORGANISM: Artificial sequence
<220> FEATURE:
<223> OTHER INFORMATION: Nuclear localization signal

<400> SEQUENCE: 250

Arg Lys Arg Ala Phe His Gly Asp Asp Pro Phe Gly Glu Gly Pro Pro
1               5                   10                  15

Asp Lys Lys

<210> SEQ ID NO 251
<211> LENGTH: 21
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (4)..(6)
<223> OTHER INFORMATION: X is any amino acid
<220> FEATURE:
<221> NAME/KEY: misc_feature
<222> LOCATION: (11)..(16)
<223> OTHER INFORMATION: X is any amino acid

<400> SEQUENCE: 251

Gly Gly Gly Xaa Xaa Xaa Lys Asn Arg Arg Xaa Xaa Xaa Xaa Xaa
1               5                   10                  15

Arg Gly Gly Arg Asn
            20

<210> SEQ ID NO 252
<211> LENGTH: 15
<212> TYPE: PRT
<213> ORGANISM: Artificial sequence
<220> FEATURE:
<223> OTHER INFORMATION: Nuclear localization signal

<400> SEQUENCE: 252

Tyr Asn Asn Gln Ser Ser Asn Phe Gly Pro Met Lys Gly Gly Asn
1               5                   10                  15

<210> SEQ ID NO 253
<211> LENGTH: 9
<212> TYPE: PRT
```

<213> ORGANISM: Artificial sequence
<220> FEATURE:
<223> OTHER INFORMATION: Nuclear localization signal

<400> SEQUENCE: 253

Pro Ala Ala Lys Arg Val Lys Leu Asp
1               5

<210> SEQ ID NO 254
<211> LENGTH: 17
<212> TYPE: PRT
<213> ORGANISM: Artificial sequence
<220> FEATURE:
<223> OTHER INFORMATION: Nuclear localization signal

<400> SEQUENCE: 254

Lys Arg Pro Ala Glu Asp Met Glu Glu Glu Gln Ala Phe Lys Arg Ser
1               5                   10                  15

Arg

<210> SEQ ID NO 255
<211> LENGTH: 11
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (2)..(2)
<223> OTHER INFORMATION: X is any amino acid
<220> FEATURE:
<221> NAME/KEY: misc_feature
<222> LOCATION: (9)..(10)
<223> OTHER INFORMATION: X is any amino acid

<400> SEQUENCE: 255

Ser Xaa Gly Thr Lys Arg Ser Tyr Xaa Xaa Met
1               5                   10

<210> SEQ ID NO 256
<211> LENGTH: 13
<212> TYPE: PRT
<213> ORGANISM: Artificial sequence
<220> FEATURE:
<223> OTHER INFORMATION: Nuclear localization signal

<400> SEQUENCE: 256

Met Asn Lys Ile Pro Ile Lys Asp Leu Leu Asn Pro Gly
1               5                   10

<210> SEQ ID NO 257
<211> LENGTH: 7
<212> TYPE: PRT
<213> ORGANISM: Artificial sequence
<220> FEATURE:
<223> OTHER INFORMATION: Nuclear localization signal

<400> SEQUENCE: 257

Pro Lys Lys Ala Arg Glu Asp
1               5

<210> SEQ ID NO 258
<211> LENGTH: 7
<212> TYPE: PRT
<213> ORGANISM: Artificial sequence
<220> FEATURE:
<223> OTHER INFORMATION: Nuclear localization signal

```
<400> SEQUENCE: 258

Val Ser Arg Lys Arg Pro Arg
1               5

<210> SEQ ID NO 259
<211> LENGTH: 8
<212> TYPE: PRT
<213> ORGANISM: Artificial sequence
<220> FEATURE:
<223> OTHER INFORMATION: Nuclear localization signal

<400> SEQUENCE: 259

Ala Pro Thr Lys Arg Lys Gly Ser
1               5

<210> SEQ ID NO 260
<211> LENGTH: 7
<212> TYPE: PRT
<213> ORGANISM: Artificial sequence
<220> FEATURE:
<223> OTHER INFORMATION: Nuclear localization signal

<400> SEQUENCE: 260

Pro Asn Lys Lys Lys Arg Lys
1               5

<210> SEQ ID NO 261
<211> LENGTH: 12
<212> TYPE: PRT
<213> ORGANISM: Artificial sequence
<220> FEATURE:
<223> OTHER INFORMATION: Nuclear localization signal

<400> SEQUENCE: 261

Glu Glu Asp Gly Pro Gln Lys Lys Arg Arg Leu
1               5                   10

<210> SEQ ID NO 262
<211> LENGTH: 8
<212> TYPE: PRT
<213> ORGANISM: Artificial sequence
<220> FEATURE:
<223> OTHER INFORMATION: Nuclear localization signal

<400> SEQUENCE: 262

Pro Leu Leu Lys Lys Ile Lys Gln
1               5

<210> SEQ ID NO 263
<211> LENGTH: 8
<212> TYPE: PRT
<213> ORGANISM: Artificial sequence
<220> FEATURE:
<223> OTHER INFORMATION: Nuclear localization signal

<400> SEQUENCE: 263

Pro Pro Gln Lys Lys Ile Lys Ser
1               5

<210> SEQ ID NO 264
<211> LENGTH: 7
<212> TYPE: PRT
<213> ORGANISM: Artificial sequence
<220> FEATURE:
<223> OTHER INFORMATION: Nuclear localization signal

<400> SEQUENCE: 264
```

```
Pro Gln Pro Lys Lys Lys Pro
1               5

<210> SEQ ID NO 265
<211> LENGTH: 9
<212> TYPE: PRT
<213> ORGANISM: Artificial sequence
<220> FEATURE:
<223> OTHER INFORMATION: Nuclear localization signal

<400> SEQUENCE: 265

Ser Lys Arg Val Ala Lys Arg Lys Leu
1               5

<210> SEQ ID NO 266
<211> LENGTH: 10
<212> TYPE: PRT
<213> ORGANISM: Artificial sequence
<220> FEATURE:
<223> OTHER INFORMATION: Nuclear localization signal

<400> SEQUENCE: 266

Ile Lys Tyr Phe Lys Lys Phe Pro Lys Asp
1               5                   10

<210> SEQ ID NO 267
<211> LENGTH: 7
<212> TYPE: PRT
<213> ORGANISM: Artificial sequence
<220> FEATURE:
<223> OTHER INFORMATION: Nuclear localization signal

<400> SEQUENCE: 267

Lys Thr Arg Lys His Arg Gly
1               5

<210> SEQ ID NO 268
<211> LENGTH: 7
<212> TYPE: PRT
<213> ORGANISM: Artificial sequence
<220> FEATURE:
<223> OTHER INFORMATION: Nuclear localization signal

<400> SEQUENCE: 268

Lys His Arg Lys His Pro Gly
1               5

<210> SEQ ID NO 269
<211> LENGTH: 8
<212> TYPE: PRT
<213> ORGANISM: Artificial sequence
<220> FEATURE:
<223> OTHER INFORMATION: Nuclear localization signal

<400> SEQUENCE: 269

Pro Gln Ser Arg Lys Lys Leu Arg
1               5

<210> SEQ ID NO 270
<211> LENGTH: 19
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (10)..(15)
```

```
<223> OTHER INFORMATION: X is any amino acid

<400> SEQUENCE: 270

His Arg Lys Tyr Glu Ala Pro Arg His Xaa Xaa Xaa Xaa Xaa Xaa Pro
1               5                   10                  15

Arg Lys Arg

<210> SEQ ID NO 271
<211> LENGTH: 9
<212> TYPE: PRT
<213> ORGANISM: Artificial sequence
<220> FEATURE:
<223> OTHER INFORMATION: Nuclear localization signal

<400> SEQUENCE: 271

Lys Lys Glu Lys Lys Lys Ser Lys Lys
1               5

<210> SEQ ID NO 272
<211> LENGTH: 18
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (4)..(14)
<223> OTHER INFORMATION: X is any amino acid

<400> SEQUENCE: 272

Arg Arg Arg Xaa Xaa Xaa Xaa Xaa Xaa Xaa Xaa Xaa Xaa Xaa Lys Arg
1               5                   10                  15

Arg Lys

<210> SEQ ID NO 273
<211> LENGTH: 46
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (3)..(17)
<223> OTHER INFORMATION: X is any amino acid

<400> SEQUENCE: 273

Lys Lys Xaa Xaa Xaa Xaa Xaa Xaa Xaa Xaa Xaa Xaa Xaa Xaa Xaa Xaa
1               5                   10                  15

Xaa Lys Lys Arg Lys Cys Tyr Phe Gln Lys Lys Ala Ala Asn Met Leu
                20                  25                  30

Gln Gln Ser Gly Ser Lys Asn Thr Gly Ala Lys Lys Arg Lys
            35                  40                  45

<210> SEQ ID NO 274
<211> LENGTH: 6
<212> TYPE: PRT
<213> ORGANISM: Artificial sequence
<220> FEATURE:
<223> OTHER INFORMATION: Nuclear localization signal

<400> SEQUENCE: 274

Lys Arg Lys Arg Arg Pro
1               5

<210> SEQ ID NO 275
```

-continued

<211> LENGTH: 9
<212> TYPE: PRT
<213> ORGANISM: Artificial sequence
<220> FEATURE:
<223> OTHER INFORMATION: Nuclear localization signal

<400> SEQUENCE: 275

Pro Lys Lys Asn Arg Leu Arg Arg Lys
1               5

<210> SEQ ID NO 276
<211> LENGTH: 28
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (5)..(23)
<223> OTHER INFORMATION: X is any amino acid

<400> SEQUENCE: 276

Lys Arg Gln Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Lys Lys Ser Lys Lys
            20                  25

<210> SEQ ID NO 277
<211> LENGTH: 9
<212> TYPE: PRT
<213> ORGANISM: Artificial sequence
<220> FEATURE:
<223> OTHER INFORMATION: Nuclear localization signal

<400> SEQUENCE: 277

Pro Ala Ala Lys Arg Val Lys Leu Asp
1               5

<210> SEQ ID NO 278
<211> LENGTH: 6
<212> TYPE: PRT
<213> ORGANISM: Artificial sequence
<220> FEATURE:
<223> OTHER INFORMATION: Nuclear localization signal

<400> SEQUENCE: 278

Gln Arg Lys Arg Gln Lys
1               5

<210> SEQ ID NO 279
<211> LENGTH: 17
<212> TYPE: PRT
<213> ORGANISM: Artificial sequence
<220> FEATURE:
<223> OTHER INFORMATION: Nuclear localization signal

<400> SEQUENCE: 279

His Arg Ile Glu Glu Lys Arg Lys Arg Thr Tyr Glu Thr Phe Lys Ser
1               5                   10                  15

Ile

<210> SEQ ID NO 280
<211> LENGTH: 7
<212> TYPE: PRT
<213> ORGANISM: Artificial sequence
<220> FEATURE:
<223> OTHER INFORMATION: Nuclear localization signal

```
<400> SEQUENCE: 280

Lys Lys Lys Tyr Lys Leu Lys
1               5

<210> SEQ ID NO 281
<211> LENGTH: 7
<212> TYPE: PRT
<213> ORGANISM: Artificial sequence
<220> FEATURE:
<223> OTHER INFORMATION: Nuclear localization signal

<400> SEQUENCE: 281

Lys Ser Lys Lys Lys Ala Gln
1               5

<210> SEQ ID NO 282
<211> LENGTH: 9
<212> TYPE: PRT
<213> ORGANISM: Artificial sequence
<220> FEATURE:
<223> OTHER INFORMATION: Nuclear localization signal

<400> SEQUENCE: 282

Leu Lys Arg Pro Arg Ser Pro Ser Ser
1               5

<210> SEQ ID NO 283
<211> LENGTH: 34
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (4)..(25)
<223> OTHER INFORMATION: X is any amino acid

<400> SEQUENCE: 283

Lys Arg Lys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Lys Glu Leu Gln Lys Gln Ile
            20                  25                  30

Thr Lys

<210> SEQ ID NO 284
<211> LENGTH: 9
<212> TYPE: PRT
<213> ORGANISM: Artificial sequence
<220> FEATURE:
<223> OTHER INFORMATION: Nuclear localization signal

<400> SEQUENCE: 284

Gly Lys Lys Lys Tyr Lys Leu Lys His
1               5

<210> SEQ ID NO 285
<211> LENGTH: 20
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (6)..(14)
<223> OTHER INFORMATION: X is any amino acid
```

-continued

```
<400> SEQUENCE: 285

Arg Lys Lys Arg Lys Xaa Xaa Xaa Xaa Xaa Xaa Xaa Xaa Lys Ala
1               5                   10                  15

Lys Lys Ser Lys
            20

<210> SEQ ID NO 286
<211> LENGTH: 17
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (3)..(13)
<223> OTHER INFORMATION: X is any amino acid

<400> SEQUENCE: 286

Lys Arg Xaa Xaa Xaa Xaa Xaa Xaa Xaa Xaa Xaa Xaa Lys Lys Leu
1               5                   10                  15

Arg

<210> SEQ ID NO 287
<211> LENGTH: 32
<212> TYPE: PRT
<213> ORGANISM: Artificial sequence
<220> FEATURE:
<223> OTHER INFORMATION: Nuclear localization signal
<220> FEATURE:
<221> NAME/KEY: misc_feature
<222> LOCATION: (5)..(26)
<223> OTHER INFORMATION: X is any amino acid

<400> SEQUENCE: 287

Arg Arg Pro Ser Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Arg Arg Lys Arg Gln Lys
            20                  25                  30

<210> SEQ ID NO 288
<211> LENGTH: 8
<212> TYPE: PRT
<213> ORGANISM: Artificial sequence
<220> FEATURE:
<223> OTHER INFORMATION: Detection domain

<400> SEQUENCE: 288

Asp Tyr Lys Asp Asp Asp Asp Lys
1               5

<210> SEQ ID NO 289
<211> LENGTH: 24
<212> TYPE: DNA
<213> ORGANISM: Artificial sequence
<220> FEATURE:
<223> OTHER INFORMATION: Sequence encoding detection domain

<400> SEQUENCE: 289
gactacaaag acgacgacga caaa                                              24

<210> SEQ ID NO 290
<211> LENGTH: 9
<212> TYPE: PRT
<213> ORGANISM: Artificial sequence
<220> FEATURE:
<223> OTHER INFORMATION: Detection domain
```

```
<400> SEQUENCE: 290

Tyr Pro Tyr Asp Val Pro Asp Tyr Ala
1               5

<210> SEQ ID NO 291
<211> LENGTH: 27
<212> TYPE: DNA
<213> ORGANISM: Artificial sequence
<220> FEATURE:
<223> OTHER INFORMATION: Sequence encoding detection domain

<400> SEQUENCE: 291
tacccatacg acgtaccaga ctacgca                                          27

<210> SEQ ID NO 292
<211> LENGTH: 6
<212> TYPE: PRT
<213> ORGANISM: Artificial sequence
<220> FEATURE:
<223> OTHER INFORMATION: Detection domain

<400> SEQUENCE: 292

Pro Pro Glu Pro Glu Thr
1               5

<210> SEQ ID NO 293
<211> LENGTH: 18
<212> TYPE: DNA
<213> ORGANISM: Artificial sequence
<220> FEATURE:
<223> OTHER INFORMATION: Sequence encoding detection domain

<400> SEQUENCE: 293
ccaccagaac cagaaaca                                                    18

<210> SEQ ID NO 294
<211> LENGTH: 12
<212> TYPE: PRT
<213> ORGANISM: Artificial sequence
<220> FEATURE:
<223> OTHER INFORMATION: Detection domain

<400> SEQUENCE: 294

Ala Glu Glu Gln Lys Leu Ile Ser Glu Glu Asp Leu
1               5                   10

<210> SEQ ID NO 295
<211> LENGTH: 36
<212> TYPE: DNA
<213> ORGANISM: Artificial sequence
<220> FEATURE:
<223> OTHER INFORMATION: Sequence encoding detection domain

<400> SEQUENCE: 295
gcagaagaac aaaaattaat aagcgaagaa gactta                                36

<210> SEQ ID NO 296
<211> LENGTH: 13
<212> TYPE: PRT
<213> ORGANISM: Artificial sequence
<220> FEATURE:
<223> OTHER INFORMATION: Protein-derived transport peptide

<400> SEQUENCE: 296

Gly Arg Lys Lys Arg Arg Gln Arg Arg Arg Pro Pro Gln
```

<210> SEQ ID NO 297
<211> LENGTH: 11
<212> TYPE: PRT
<213> ORGANISM: Artificial sequence
<220> FEATURE:
<223> OTHER INFORMATION: Protein-derived transport peptide

<400> SEQUENCE: 297

Tyr Ala Arg Ala Ala Ala Arg Gln Ala Arg Ala
1               5                   10

<210> SEQ ID NO 298
<211> LENGTH: 9
<212> TYPE: PRT
<213> ORGANISM: Artificial sequence
<220> FEATURE:
<223> OTHER INFORMATION: Protein-derived transport peptide

<400> SEQUENCE: 298

Arg Arg Arg Arg Arg Arg Arg Arg Arg
1               5

<210> SEQ ID NO 299
<211> LENGTH: 9
<212> TYPE: PRT
<213> ORGANISM: Artificial sequence
<220> FEATURE:
<223> OTHER INFORMATION: Protein-derived transport peptide
<220> FEATURE:
<221> NAME/KEY: MISC_FEATURE
<222> LOCATION: (1)..(9)
<223> OTHER INFORMATION: All D-amino acids

<400> SEQUENCE: 299

Arg Arg Arg Arg Arg Arg Arg Arg Arg
1               5

<210> SEQ ID NO 300
<211> LENGTH: 34
<212> TYPE: PRT
<213> ORGANISM: Artificial sequence
<220> FEATURE:
<223> OTHER INFORMATION: Protein-derived transport peptide

<400> SEQUENCE: 300

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 301
<211> LENGTH: 27
<212> TYPE: PRT
<213> ORGANISM: Artificial sequence
<220> FEATURE:
<223> OTHER INFORMATION: Protein-derived transport peptide

<400> SEQUENCE: 301

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 302
<211> LENGTH: 12
<212> TYPE: PRT
<213> ORGANISM: Artificial sequence
<220> FEATURE:
<223> OTHER INFORMATION: Protein-derived transport peptide

<400> SEQUENCE: 302

Pro Leu Ser Ser Ile Phe Ser Arg Ile Gly Asp Pro
1               5                   10

<210> SEQ ID NO 303
<211> LENGTH: 16
<212> TYPE: PRT
<213> ORGANISM: Artificial sequence
<220> FEATURE:
<223> OTHER INFORMATION: Protein-derived transport peptide

<400> SEQUENCE: 303

Ala Ala Val Ala Leu Leu Pro Ala Val Leu Leu Ala Leu Leu Ala Pro
1               5                   10                  15

<210> SEQ ID NO 304
<211> LENGTH: 12
<212> TYPE: PRT
<213> ORGANISM: Artificial sequence
<220> FEATURE:
<223> OTHER INFORMATION: Protein-derived transport peptide

<400> SEQUENCE: 304

Ala Ala Val Leu Leu Pro Val Leu Leu Ala Ala Pro
1               5                   10

<210> SEQ ID NO 305
<211> LENGTH: 15
<212> TYPE: PRT
<213> ORGANISM: Artificial sequence
<220> FEATURE:
<223> OTHER INFORMATION: Protein-derived transport peptide

<400> SEQUENCE: 305

Val Thr Val Leu Ala Leu Gly Ala Leu Ala Gly Val Gly Val Gly
1               5                   10                  15

<210> SEQ ID NO 306
<211> LENGTH: 21
<212> TYPE: PRT
<213> ORGANISM: Artificial sequence
<220> FEATURE:
<223> OTHER INFORMATION: Protein-derived transport peptide

<400> SEQUENCE: 306

Gly Ala Leu Phe Leu Gly Trp Leu Gly Ala Ala Gly Ser Thr Met Gly
1               5                   10                  15

Ala Trp Ser Gln Pro
            20

<210> SEQ ID NO 307
<211> LENGTH: 27
<212> TYPE: PRT
<213> ORGANISM: Artificial sequence
<220> FEATURE:
<223> OTHER INFORMATION: Protein-derived transport peptide

<400> SEQUENCE: 307

Gly Trp Thr Leu Asn Ser Ala Gly Tyr Leu Leu Gly Leu Ile Asn Leu

```
1               5                   10                  15
Lys Ala Leu Ala Ala Leu Ala Lys Lys Ile Leu
            20                  25
```

<210> SEQ ID NO 308
<211> LENGTH: 18
<212> TYPE: PRT
<213> ORGANISM: Artificial sequence
<220> FEATURE:
<223> OTHER INFORMATION: Protein-derived transport peptide

<400> SEQUENCE: 308

```
Lys Leu Ala Leu Lys Leu Ala Leu Lys Ala Leu Lys Ala Ala Leu Lys
1               5                   10                  15
Leu Ala
```

<210> SEQ ID NO 309
<211> LENGTH: 21
<212> TYPE: PRT
<213> ORGANISM: Artificial sequence
<220> FEATURE:
<223> OTHER INFORMATION: Protein-derived transport peptide

<400> SEQUENCE: 309

```
Lys Glu Thr Trp Trp Glu Thr Trp Trp Thr Glu Trp Ser Gln Pro Lys
1               5                   10                  15
Lys Lys Arg Lys Val
            20
```

<210> SEQ ID NO 310
<211> LENGTH: 17
<212> TYPE: PRT
<213> ORGANISM: Artificial sequence
<220> FEATURE:
<223> OTHER INFORMATION: RNA binding domain

<400> SEQUENCE: 310

```
Thr Arg Gln Ala Arg Arg Asn Arg Arg Arg Arg Trp Arg Glu Arg Gln
1               5                   10                  15
Arg
```

<210> SEQ ID NO 311
<211> LENGTH: 19
<212> TYPE: PRT
<213> ORGANISM: Artificial sequence
<220> FEATURE:
<223> OTHER INFORMATION: RNA binding domain
<220> FEATURE:
<221> NAME/KEY: misc_feature
<222> LOCATION: (1)..(1)
<223> OTHER INFORMATION: X is M or L

<400> SEQUENCE: 311

```
Xaa Asp Ala Gln Thr Arg Arg Arg Glu Arg Arg Ala Glu Lys Gln Ala
1               5                   10                  15
Gln Trp Lys
```

<210> SEQ ID NO 312
<211> LENGTH: 17
<212> TYPE: PRT
<213> ORGANISM: Artificial sequence
<220> FEATURE:
<223> OTHER INFORMATION: RNA binding domain

<400> SEQUENCE: 312

-continued

Asn Ala Lys Thr Arg Arg His Glu Arg Arg Lys Leu Ala Ile Glu
1               5                   10                  15

Arg

<210> SEQ ID NO 313
<211> LENGTH: 16
<212> TYPE: PRT
<213> ORGANISM: Artificial sequence
<220> FEATURE:
<223> OTHER INFORMATION: RNA binding domain

<400> SEQUENCE: 313

Met Pro Lys Thr Arg Arg Pro Arg Ser Gln Arg Lys Arg Pro
1               5                   10                  15

<210> SEQ ID NO 314
<211> LENGTH: 13
<212> TYPE: PRT
<213> ORGANISM: Artificial sequence
<220> FEATURE:
<223> OTHER INFORMATION: RNA binding domain

<400> SEQUENCE: 314

Gly Arg Lys Lys Arg Arg Gln Arg Arg Arg Pro Pro Gln
1               5                   10

<210> SEQ ID NO 315
<211> LENGTH: 13
<212> TYPE: PRT
<213> ORGANISM: Artificial sequence
<220> FEATURE:
<223> OTHER INFORMATION: Nuclear export signal

<400> SEQUENCE: 315

Ala Leu Gln Lys Lys Leu Glu Glu Leu Glu Leu Asp Glu
1               5                   10

<210> SEQ ID NO 316
<211> LENGTH: 13
<212> TYPE: PRT
<213> ORGANISM: Artificial sequence
<220> FEATURE:
<223> OTHER INFORMATION: Nuclear export signal

<400> SEQUENCE: 316

Asp Leu Gln Lys Lys Leu Glu Glu Leu Glu Leu Asp Glu
1               5                   10

<210> SEQ ID NO 317
<211> LENGTH: 24
<212> TYPE: PRT
<213> ORGANISM: Artificial sequence
<220> FEATURE:
<223> OTHER INFORMATION: Nuclear export signal

<400> SEQUENCE: 317

Asp Lys Glu Arg Trp Glu Asp Val Lys Glu Glu Met Thr Ser Ala Leu
1               5                   10                  15

Ala Thr Met Arg Val Asp Tyr Glu
                20

<210> SEQ ID NO 318
<211> LENGTH: 19
<212> TYPE: PRT
<213> ORGANISM: Artificial sequence

```
<220> FEATURE:
<223> OTHER INFORMATION: Nuclear export signal

<400> SEQUENCE: 318

Trp Asp Arg Thr Phe Ser Leu Phe Gln Gln Leu Leu Gln Ser Ser Phe
1               5                   10                  15

Val Val Glu

<210> SEQ ID NO 319
<211> LENGTH: 9
<212> TYPE: PRT
<213> ORGANISM: Artificial sequence
<220> FEATURE:
<223> OTHER INFORMATION: Nuclear export signal

<400> SEQUENCE: 319

Leu Pro Pro Leu Glu Arg Leu Thr Leu
1               5

<210> SEQ ID NO 320
<211> LENGTH: 10
<212> TYPE: PRT
<213> ORGANISM: Artificial sequence
<220> FEATURE:
<223> OTHER INFORMATION: Nuclear export signal

<400> SEQUENCE: 320

Leu Ala Leu Lys Leu Ala Gly Leu Asp Ile
1               5                   10

<210> SEQ ID NO 321
<211> LENGTH: 10
<212> TYPE: PRT
<213> ORGANISM: Artificial sequence
<220> FEATURE:
<223> OTHER INFORMATION: Nuclear export signal

<400> SEQUENCE: 321

Leu Gln Gln Gln Leu Gly Gln Leu Thr Leu
1               5                   10

<210> SEQ ID NO 322
<211> LENGTH: 10
<212> TYPE: PRT
<213> ORGANISM: Artificial sequence
<220> FEATURE:
<223> OTHER INFORMATION: Nuclear export signal

<400> SEQUENCE: 322

Leu Glu Ser Asn Leu Arg Glu Leu Gln Ile
1               5                   10

<210> SEQ ID NO 323
<211> LENGTH: 10
<212> TYPE: PRT
<213> ORGANISM: Artificial sequence
<220> FEATURE:
<223> OTHER INFORMATION: Nuclear export signal

<400> SEQUENCE: 323

Leu Asp Lys Leu Ser Val Leu Thr Leu Ser
1               5                   10

<210> SEQ ID NO 324
<211> LENGTH: 11
<212> TYPE: PRT
```

```
<213> ORGANISM: Artificial sequence
<220> FEATURE:
<223> OTHER INFORMATION: Nuclear export signal

<400> SEQUENCE: 324

Leu Trp Gln Phe Leu Leu Gln Leu Leu Leu Asp
1               5                   10

<210> SEQ ID NO 325
<211> LENGTH: 11
<212> TYPE: PRT
<213> ORGANISM: Artificial sequence
<220> FEATURE:
<223> OTHER INFORMATION: Nuclear export signal

<400> SEQUENCE: 325

Leu Cys Gln Ala Phe Ser Lys Val Ile Leu Ala
1               5                   10

<210> SEQ ID NO 326
<211> LENGTH: 115
<212> TYPE: PRT
<213> ORGANISM: Artificial sequence
<220> FEATURE:
<223> OTHER INFORMATION: cAMP-dependent protein kinase interaction
      fusion protein

<400> SEQUENCE: 326

Pro Gln Thr Pro Leu His Thr Ser Arg Val Leu Lys Glu Asp Lys Glu
1               5                   10                  15

Arg Trp Glu Asp Val Lys Glu Glu Met Thr Ser Ala Leu Ala Thr Met
                20                  25                  30

Cys Val Asp Tyr Glu Gln Ile Lys Ile Lys Lys Ile Glu Asp Ala Ser
            35                  40                  45

Pro Lys Lys Lys Arg Lys Val Leu Glu Ile Ala Glu Ser Glu Asp Ser
        50                  55                  60

Gln Glu Ser Val Asp Ser Val Thr Asp Ser Gln Lys Arg Arg Glu Ile
65                  70                  75                  80

Leu Ser Arg Arg Pro Ser Tyr Arg Lys Ile Leu Asn Asp Leu Ser Ser
                85                  90                  95

Asp Ala Pro Gly Val Pro Arg Ile Glu Glu Glu Lys Ser Glu Glu Glu
            100                 105                 110

Thr Ser Ala
        115

<210> SEQ ID NO 327
<211> LENGTH: 345
<212> TYPE: DNA
<213> ORGANISM: Artificial sequence
<220> FEATURE:
<223> OTHER INFORMATION: Sequence encoding cAMP-dependent protein kinase
      interaction fusion protein

<400> SEQUENCE: 327
cctcagactc cactgcacac cagccgtgtc ctgaaggagg acaaggaacg atgggaggat      60
gtcaaggagg agatgaccag tgccttggcc acgatgtgtg ttgactatga gcagatcaag     120
ataaagaaga tagaagacgc atccccaaag aagaagcgaa aggtgctcga gattgcagaa     180
agtgaagatt cacaggagtc agtggatagt gtaactgatt cccaaaagcg aagggaaatt     240
ctttcaagga ggccttccta caggaaaatt ttgaatgact atcttctga tgcaccagga      300 gtgccaagga ttgaagaaga gaagtctgaa gaggagactt cagca                     345
```

<210> SEQ ID NO 328
<211> LENGTH: 71
<212> TYPE: PRT
<213> ORGANISM: Artificial sequence
<220> FEATURE:
<223> OTHER INFORMATION: MAPK binding fusion protein

<400> SEQUENCE: 328

Pro Gln Thr Pro Leu His Thr Ser Arg Val Leu Lys Glu Asp Lys Glu
1               5                   10                  15
Arg Trp Glu Asp Val Lys Glu Glu Met Thr Ser Ala Leu Ala Thr Met
            20                  25                  30
Arg Val Asp Tyr Glu Gln Ile Lys Ile Lys Lys Ile Glu Asp Ala Gln
        35                  40                  45
Lys Lys Arg Lys Ser Ser Ile Leu Ala Gln Arg Arg Val Arg Lys Leu
    50                  55                  60
Pro Ser Thr Thr Leu Ala His
65                  70

<210> SEQ ID NO 329
<211> LENGTH: 216
<212> TYPE: DNA
<213> ORGANISM: Artificial sequence
<220> FEATURE:
<223> OTHER INFORMATION: Sequence encoding MAPK binding fusion protein

<400> SEQUENCE: 329
cctcagactc cactgcacac cagccgtgtc ctgaaggagg acaaggagcg atgggaggat      60
gtcaaggagg agatgaccag tgccttggcc acgatgcgtg ttgactatga gcagatcaag     120
ataaagaaga tagaagacgc acagaagaag cgtaagagta gtatcttggc ccagcgtcga    180
gtccgaaagc tgccttccac tactttggcc cactga                               216

<210> SEQ ID NO 330
<211> LENGTH: 92
<212> TYPE: PRT
<213> ORGANISM: Artificial sequence
<220> FEATURE:
<223> OTHER INFORMATION: variant MAPK binding fusion protein

<400> SEQUENCE: 330

Glu Phe Gly Ala Gly Asp Glu Asp Lys Glu Arg Trp Glu Asp Val Lys
1               5                   10                  15
Glu Glu Met Thr Ser Ala Leu Ala Thr Met Arg Val Asp Tyr Glu Gln
            20                  25                  30
Ile Leu Ala Gly Gln Pro Lys Ala Asn Pro Gly Ala Gly Asp Gly Gln
        35                  40                  45
Pro Lys Ala Asn Pro Lys Arg Val Asp Pro Leu Glu Pro Lys Lys Lys
    50                  55                  60
Arg Lys Val Lys Asp Leu Ser Ser Ile Leu Ala Gln Arg Arg Val Arg
65                  70                  75                  80
Lys Leu Pro Ser Thr Thr Leu Val Asp Leu Ala His
                85                  90

<210> SEQ ID NO 331
<211> LENGTH: 288
<212> TYPE: DNA
<213> ORGANISM: Artificial sequence
<220> FEATURE:
<223> OTHER INFORMATION: Sequence encoding variant MAPK binding fusion -continued protein

<400> SEQUENCE: 331

```
gaattcggag ctggcgacga ggacaaggag cggtgggagg acgtgaagga ggagatgacc    60
agcgccctgg ccaccatgcg ggtggactac gagcagattc tagccggaca gccaaaggcc   120
aaccccggcg ccggagatgg tcaacctaaa gctaatccta aacgcgtgga tcctctcgag   180
ccaaagaaga agcggaaggt gaaagatcta tcatccatcc tggcccagcg gcgagtgagg   240
aagttgccat ccaccaccct ggtcgacctg gcccactaaa gcggccgc                288
```

<210> SEQ ID NO 332
<211> LENGTH: 89
<212> TYPE: PRT
<213> ORGANISM: Artificial sequence
<220> FEATURE:
<223> OTHER INFORMATION: c-Jun N-terminal protein kinase fusion protein

<400> SEQUENCE: 332

Pro Gln Thr Pro Leu His Thr Ser Arg Val Leu Lys Glu Asp Lys Glu
1               5                   10                  15

Arg Trp Glu Asp Val Lys Glu Glu Met Thr Ser Ala Leu Ala Thr Met
            20                  25                  30

Arg Val Asp Tyr Glu Gln Ile Lys Ile Lys Lys Ile Glu Asp Ala Ser
        35                  40                  45

Asn Pro Ser Arg Pro Lys Ile Leu Lys Gln Ser Met Thr Gln Asn Leu
    50                  55                  60

Ala Val Pro Val Gly Ser Leu Lys Pro His Leu Cys Ala Lys Asn Ser
65                  70                  75                  80

Asp Leu Lys Arg Arg Lys Lys Ala His
                85

<210> SEQ ID NO 333
<211> LENGTH: 270
<212> TYPE: DNA
<213> ORGANISM: Artificial sequence
<220> FEATURE:
<223> OTHER INFORMATION: Sequence encoding c-Jun N-terminal protein
      kinase fusion protein

<400> SEQUENCE: 333

```
cctcagactc cactgcacac cagccgtgtc ctgaaggagg acaaggaacg atgggaggat    60
gtcaaggagg agatgaccag tgccttggcc acgatgcgtg ttgactatga gcagatcaag   120
ataaagaaga tagaagacgc atccaaccct tctagaccca agatcctgaa acagagcatg   180
acccagaacc tggccgtccc agtggggagc ctgaagccgc acctctgcgc caagaactcg   240
gacctcaagc gtcgtaagaa ggcccactga                                    270
```

<210> SEQ ID NO 334
<211> LENGTH: 10
<212> TYPE: DNA
<213> ORGANISM: Artificial sequence
<220> FEATURE:
<223> OTHER INFORMATION: DNA binding sequence

<400> SEQUENCE: 334

```
ggggcggggc                                                           10
```

<210> SEQ ID NO 335
<211> LENGTH: 9
<212> TYPE: DNA

```
<213> ORGANISM: Artificial sequence
<220> FEATURE:
<223> OTHER INFORMATION: DNA binding sequence

<400> SEQUENCE: 335 gcgtgggcg                                                              9

<210> SEQ ID NO 336
<211> LENGTH: 6
<212> TYPE: PRT
<213> ORGANISM: Artificial sequence
<220> FEATURE:
<223> OTHER INFORMATION: Nuclear localization signal

<400> SEQUENCE: 336

Gln Arg Lys Arg Gln Lys
1               5

<210> SEQ ID NO 337
<211> LENGTH: 10
<212> TYPE: PRT
<213> ORGANISM: Artificial sequence
<220> FEATURE:
<223> OTHER INFORMATION: Nuclear export signal

<400> SEQUENCE: 337

Leu Gln Lys Lys Leu Glu Glu Leu Glu Leu
1               5                   10

<210> SEQ ID NO 338
<211> LENGTH: 91
<212> TYPE: PRT
<213> ORGANISM: Artificial sequence
<220> FEATURE:
<223> OTHER INFORMATION: DNA binding domain

<400> SEQUENCE: 338

Lys Lys Lys Gln His Ile Cys His Ile Gln Cys Gly Lys Val Tyr
1               5                   10                  15

Gly Lys Thr Ser His Leu Arg Ala His Leu Arg Trp His Thr Gly Glu
            20                  25                  30

Arg Pro Phe Met Cys Thr Trp Ser Tyr Cys Gly Lys Arg Phe Thr Arg
        35                  40                  45

Ser Asp Glu Leu Gln Arg His Lys Arg Thr His Thr Gly Glu Lys Lys
    50                  55                  60

Phe Ala Cys Pro Glu Cys Pro Lys Arg Phe Met Arg Ser Asp His Leu
65                  70                  75                  80

Ser Lys His Ile Lys Thr His Gln Asn Lys Lys
                85                  90

<210> SEQ ID NO 339
<211> LENGTH: 81
<212> TYPE: PRT
<213> ORGANISM: Artificial sequence
<220> FEATURE:
<223> OTHER INFORMATION: DNA binding domain

<400> SEQUENCE: 339

Tyr Ala Cys Pro Val Glu Ser Cys Asp Arg Arg Phe Ser Arg Ser Asp
1               5                   10                  15

Glu Leu Thr Arg His Ile Arg Ile His Thr Gly Gln Lys Pro Phe Gln
            20                  25                  30

Cys Arg Ile Cys Met Arg Asn Phe Ser Arg Ser Asp His Leu Thr Thr
```

```
                35                  40                  45
His Ile Arg Thr His Thr Gly Glu Lys Pro Phe Ala Cys Asp Ile Cys
    50                  55                  60

Gly Arg Lys Phe Ala Arg Ser Asp Glu Arg Lys Arg His Thr Lys Ile
65                  70                  75                  80

His

<210> SEQ ID NO 340
<211> LENGTH: 38
<212> TYPE: DNA
<213> ORGANISM: Artificial sequence
<220> FEATURE:
<223> OTHER INFORMATION: Sequence encoding post-translational
      modification site

<400> SEQUENCE: 340
accctgagtc ccattgcgcc ccgtagcccg gccaagct                              38

<210> SEQ ID NO 341
<211> LENGTH: 13
<212> TYPE: PRT
<213> ORGANISM: Artificial sequence
<220> FEATURE:
<223> OTHER INFORMATION: Post-translational modification site

<400> SEQUENCE: 341

Thr Leu Ser Pro Ile Ala Pro Arg Ser Pro Ala Lys Leu
1               5                   10

<210> SEQ ID NO 342
<211> LENGTH: 54
<212> TYPE: DNA
<213> ORGANISM: Artificial sequence
<220> FEATURE:
<223> OTHER INFORMATION: Sequence encoding post-translational
      modification site

<400> SEQUENCE: 342
ttgaagccac catctcccat ctcagaagct ccacgaactc tagcttctcc aaag           54

<210> SEQ ID NO 343
<211> LENGTH: 18
<212> TYPE: PRT
<213> ORGANISM: Artificial sequence
<220> FEATURE:
<223> OTHER INFORMATION: Post-translational modification site

<400> SEQUENCE: 343

Leu Lys Pro Pro Ser Pro Ile Ser Glu Ala Pro Arg Thr Leu Ala Ser
1               5                   10                  15

Pro Lys

<210> SEQ ID NO 344
<211> LENGTH: 15
<212> TYPE: DNA
<213> ORGANISM: Artificial sequence
<220> FEATURE:
<223> OTHER INFORMATION: Sequence encoding post-translational
      modification site

<400> SEQUENCE: 344
aggaggcctt cctac                                                      15

<210> SEQ ID NO 345
```

```
<211> LENGTH: 5
<212> TYPE: PRT
<213> ORGANISM: Artificial sequence
<220> FEATURE:
<223> OTHER INFORMATION: Post-translational modification site

<400> SEQUENCE: 345

Arg Arg Pro Ser Tyr
1               5

<210> SEQ ID NO 346
<211> LENGTH: 45
<212> TYPE: DNA
<213> ORGANISM: Artificial sequence
<220> FEATURE:
<223> OTHER INFORMATION: Sequence encoding post-translational
      modification site

<400> SEQUENCE: 346
tcattcgtgg gaacagcgca gtacgtttct ccagagctgc tcacg          45

<210> SEQ ID NO 347
<211> LENGTH: 15
<212> TYPE: PRT
<213> ORGANISM: Artificial sequence
<220> FEATURE:
<223> OTHER INFORMATION: Post-translational modification site

<400> SEQUENCE: 347

Ser Phe Val Gly Thr Ala Gln Tyr Val Ser Pro Glu Leu Leu Thr
1               5                   10                  15

<210> SEQ ID NO 348
<211> LENGTH: 27
<212> TYPE: DNA
<213> ORGANISM: Artificial sequence
<220> FEATURE:
<223> OTHER INFORMATION: Sequence encoding post-translational
      modification site

<400> SEQUENCE: 348
gagccgccgg tctacgcaaa cctcagc                              27

<210> SEQ ID NO 349
<211> LENGTH: 9
<212> TYPE: PRT
<213> ORGANISM: Artificial sequence
<220> FEATURE:
<223> OTHER INFORMATION: Post-translational modification site

<400> SEQUENCE: 349

Glu Pro Pro Val Tyr Ala Asn Leu Ser
1               5

<210> SEQ ID NO 350
<211> LENGTH: 5
<212> TYPE: PRT
<213> ORGANISM: Artificial sequence
<220> FEATURE:
<223> OTHER INFORMATION: Post-translational modification site
<220> FEATURE:
<221> NAME/KEY: misc_feature
<222> LOCATION: (4)..(4)
<223> OTHER INFORMATION: X is any amino acid

<400> SEQUENCE: 350

Ile Tyr Ala Xaa Pro
1               5
```

```
<210> SEQ ID NO 351
<211> LENGTH: 24
<212> TYPE: DNA
<213> ORGANISM: Artificial sequence
<220> FEATURE:
<223> OTHER INFORMATION: Sequence encoding post-translational
      modification site

<400> SEQUENCE: 351
ggaactggat atatcaagac tgag                                             24

<210> SEQ ID NO 352
<211> LENGTH: 8
<212> TYPE: PRT
<213> ORGANISM: Artificial sequence
<220> FEATURE:
<223> OTHER INFORMATION: Post-translational modification site

<400> SEQUENCE: 352

Gly Thr Gly Tyr Ile Lys Thr Glu
1               5

<210> SEQ ID NO 353
<211> LENGTH: 12
<212> TYPE: DNA
<213> ORGANISM: Artificial sequence
<220> FEATURE:
<223> OTHER INFORMATION: Sequence encoding post-translational
      modification site

<400> SEQUENCE: 353
cgccataaaa aa                                                          12

<210> SEQ ID NO 354
<211> LENGTH: 4
<212> TYPE: PRT
<213> ORGANISM: Artificial sequence
<220> FEATURE:
<223> OTHER INFORMATION: Post-translational modification site

<400> SEQUENCE: 354

Arg His Lys Lys
1

<210> SEQ ID NO 355
<211> LENGTH: 45
<212> TYPE: DNA
<213> ORGANISM: Artificial sequence
<220> FEATURE:
<223> OTHER INFORMATION: Sequence encoding post-translational
      modification site

<400> SEQUENCE: 355
cacccaggga aaggtgtgaa atctccgggg gagaagtcac gctat                      45

<210> SEQ ID NO 356
<211> LENGTH: 15
<212> TYPE: PRT
<213> ORGANISM: Artificial sequence
<220> FEATURE:
<223> OTHER INFORMATION: Post-translational modification site

<400> SEQUENCE: 356

His Pro Gly Lys Gly Val Lys Ser Pro Gly Glu Lys Ser Arg Tyr
1               5                   10                  15
```

```
<210> SEQ ID NO 357
<211> LENGTH: 27
<212> TYPE: DNA
<213> ORGANISM: Artificial sequence
<220> FEATURE:
<223> OTHER INFORMATION: Sequence encoding post-translational
      modification site

<400> SEQUENCE: 357
tgcatgtcct gcaaatgcgt tctgtct                                          27

<210> SEQ ID NO 358
<211> LENGTH: 9
<212> TYPE: PRT
<213> ORGANISM: Artificial sequence
<220> FEATURE:
<223> OTHER INFORMATION: Post-translational modification site

<400> SEQUENCE: 358

Cys Met Ser Cys Lys Cys Val Leu Ser
1               5

<210> SEQ ID NO 359
<211> LENGTH: 12
<212> TYPE: DNA
<213> ORGANISM: Artificial sequence
<220> FEATURE:
<223> OTHER INFORMATION: Sequence encoding post-translational
      modification site

<400> SEQUENCE: 359
tgcgttctgt ct                                                          12

<210> SEQ ID NO 360
<211> LENGTH: 4
<212> TYPE: PRT
<213> ORGANISM: Artificial sequence
<220> FEATURE:
<223> OTHER INFORMATION: Post-translational modification site

<400> SEQUENCE: 360

Cys Val Leu Ser
1

<210> SEQ ID NO 361
<211> LENGTH: 12
<212> TYPE: DNA
<213> ORGANISM: Artificial sequence
<220> FEATURE:
<223> OTHER INFORMATION: Sequence encoding post-translational
      modification site

<400> SEQUENCE: 361
tgtgtaatta tg                                                          12

<210> SEQ ID NO 362
<211> LENGTH: 4
<212> TYPE: PRT
<213> ORGANISM: Artificial sequence
<220> FEATURE:
<223> OTHER INFORMATION: Post-translational modification site

<400> SEQUENCE: 362

Cys Val Ile Met
1
```

<210> SEQ ID NO 363
<211> LENGTH: 144
<212> TYPE: DNA
<213> ORGANISM: Artificial sequence
<220> FEATURE:
<223> OTHER INFORMATION: Sequence encoding plekstrin homology domain

<400> SEQUENCE: 363
ctgcccccca aggtgaaggc ctatctgagc caaggggagc gcttcatcaa atgggatgat      60
gaaactacag ttgcctctcc agttatcctc cgtgtggatc ctaagggcta ctacttatac    120
tggacgtatc aaagtaagga gatg                                            144

<210> SEQ ID NO 364
<211> LENGTH: 48
<212> TYPE: PRT
<213> ORGANISM: Artificial sequence
<220> FEATURE:
<223> OTHER INFORMATION: Plekstrin homology domain

<400> SEQUENCE: 364

Leu Pro Pro Lys Val Lys Ala Tyr Leu Ser Gln Gly Glu Arg Phe Ile
1               5                   10                  15

Lys Trp Asp Asp Glu Thr Thr Val Ala Ser Pro Val Ile Leu Arg Val
            20                  25                  30

Asp Pro Lys Gly Tyr Tyr Leu Tyr Trp Thr Tyr Gln Ser Lys Glu Met
        35                  40                  45

<210> SEQ ID NO 365
<211> LENGTH: 150
<212> TYPE: DNA
<213> ORGANISM: Artificial sequence
<220> FEATURE:
<223> OTHER INFORMATION: Sequence encoding diacylglycerol binding domain
      from Protein Kinase C

<400> SEQUENCE: 365
cacaagttca ccgctcgttt cttcaagcag ccaaccttct gcagtcactg taccgacttc      60
atctggggca ttggaaagca gggcctgcaa tgtcaagtct gcagctttgt ggttcaccgc    120
cgatgccacg aatttgtgac cttcgagtgt                                      150

<210> SEQ ID NO 366
<211> LENGTH: 50
<212> TYPE: PRT
<213> ORGANISM: Artificial Sequence
<220> FEATURE:
<223> OTHER INFORMATION: Diacylglycerol binding domain from Protein
      Kinase C

<400> SEQUENCE: 366

His Lys Phe Thr Ala Arg Phe Phe Lys Gln Pro Thr Phe Cys Ser His
1               5                   10                  15

Cys Thr Asp Phe Ile Trp Gly Ile Gly Lys Gln Gly Leu Gln Cys Gln
            20                  25                  30

Val Cys Ser Phe Val Val His Arg Arg Cys His Glu Phe Val Thr Phe
        35                  40                  45

Glu Cys
    50